(12) United States Patent
Imamura et al.

(10) Patent No.: US 6,808,854 B2
(45) Date of Patent: Oct. 26, 2004

(54) POLYHYDROXYALKANOATES HAVING IN ITS SIDE CHAIN PHENYLSULFINYL STRUCTURE AND/OR PHENYL SULFONYL STRUCTURE AND PRODUCTION PROCESS THEREFOR; CHARGE CONTROL AGENT, TONER BINDER AND TONER CONTAINING SAME; AND IMAGE FORMING METHOD AND IMAGE FORMING APPARATUS USING THE TONER

(75) Inventors: Takeshi Imamura, Kanagawa (JP); Etsuko Sugawa, Kanagawa (JP); Tetsuya Yano, Kanagawa (JP); Takashi Kenmoku, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 128 days.

(21) Appl. No.: 10/133,671

(22) Filed: Apr. 29, 2002

(65) Prior Publication Data

US 2003/0100700 A1 May 29, 2003

(30) Foreign Application Priority Data

Apr. 27, 2001 (JP) ........................................ 2001-131831
Apr. 27, 2001 (JP) ........................................ 2001-133640

(51) Int. Cl.$^7$ ............................ G03G 9/00; C12P 11/00; C08G 63/06

(52) U.S. Cl. .................... 430/110; 528/361; 528/363; 528/364; 430/108; 430/127; 430/137; 430/311; 430/332; 435/130; 435/132; 435/136; 435/137; 435/155; 435/162; 435/253.3

(58) Field of Search ......................... 528/361, 363, 528/364; 430/108, 110, 127, 137, 311, 332; 435/130, 132, 136, 137, 155, 162, 253.3

(56) References Cited

U.S. PATENT DOCUMENTS

| | | | |
|---|---|---|---|
| 4,393,167 A | 7/1983 | Holmes et al. | 525/64 |
| 4,442,189 A | 4/1984 | Lu et al. | 430/45 |
| 4,480,021 A | 10/1984 | Lu et al. | 430/106.6 |
| 4,795,690 A | 1/1989 | Shindo et al. | 430/109 |
| 4,840,863 A | 6/1989 | Otsu et al. | 430/110 |
| 4,876,331 A | 10/1989 | Doi | 528/361 |
| 4,925,765 A | 5/1990 | Madeleine | 430/110 |
| 5,004,664 A | 4/1991 | Fuller et al. | 430/106.6 |
| 5,135,859 A | 8/1992 | Witholt et al. | 435/135 |
| 5,200,332 A | 4/1993 | Yamane et al. | 435/135 |
| 5,292,860 A | 3/1994 | Shiotani et al. | 528/361 |
| 5,667,927 A | 9/1997 | Kubota et al. | 430/109 |

FOREIGN PATENT DOCUMENTS

| | | |
|---|---|---|
| EP | 1067569 | 1/2001 |
| EP | 1 245 682 | 10/2002 |

(List continued on next page.)

OTHER PUBLICATIONS

Takagi, et al., "Biosynthesis of Polyhydroxyalkanoate with a Thiophenoxy Side Group Obtained from *Pseudomonas putida*", Macromolecules, vol. 32, pp. 8315–8318 (1999).

(List continued on next page.)

*Primary Examiner*—Samuel A. Acquah
(74) *Attorney, Agent, or Firm*—Fitzpatrick, Cella, Harper & Scinto

(57) ABSTRACT

The present invention provides a novel polyhydroxyalkanoate (PHA) containing a 3-hydroxyalkanoic unit which has at its side chain terminal a substituted phenylsulfinyl group and/or a substituted phenylsulfonyl group, and a production process thereof. The novel PHA can be produced by oxidizing with a peroxide a biosynthetic PHA containing a 3-hydroxyalkanoic unit which has at its side chain terminal a substituted phenylsufanyl group. The novel PHA has a superior function as a charge control agent, besides is biodegradable, hence is contributable to environmental conservation.

30 Claims, 13 Drawing Sheets

FOREIGN PATENT DOCUMENTS

| | | |
|---|---|---|
| JP | 60-108861 | 6/1985 |
| JP | 61-3149 | 1/1986 |
| JP | 62-210472 | 9/1987 |
| JP | 63-38958 | 2/1988 |
| JP | 63-88564 | 4/1988 |
| JP | 4-46424 | 7/1992 |
| JP | 5-74492 | 1/1993 |
| JP | 5-93049 | 4/1993 |
| JP | 6-15604 | 3/1994 |
| JP | 6-289644 | 10/1994 |
| JP | 7-14352 | 2/1995 |
| JP | 7-120975 | 5/1995 |
| JP | 7-265065 | 10/1995 |
| JP | 8-19227 | 2/1996 |
| JP | 8-220809 | 8/1996 |
| JP | 8-262796 | 10/1996 |
| JP | 2552133 B2 | 11/1996 |
| JP | 9-191893 | 7/1997 |
| JP | 2642937 | 8/1997 |
| JP | 9-274335 | 10/1997 |
| JP | 9-281746 | 10/1997 |
| JP | 2807796 B2 | 10/1998 |
| JP | 2989175 B1 | 2/1999 |
| JP | 2001-57145 | 2/2001 |
| JP | 2001-57142 | 12/2001 |

OTHER PUBLICATIONS

Steinbüchel, et al., "Diversity of bacterial polyhydroxyalkanoic acids", FEMS Microbiology Letters, vol. 128, pp. 219–228 (1995).

Gross, et al.; "Cyanophenoxy–Containing Microbial Polyesters . . . "; Polymer International, 39 (1996) 205–213.

Curley, et al.; "Production of Poly(3–hydroxyalkanoates . . . ") Macromolecules (1996) 29, 1762–1766.

Park, et al.; Epoxidation of Bacterial Polyesters . . . 10–Undecenoic Acid; Macromolecules (1998) 31 5, 1480–1486.

Park, et al.; "Epoxidation of Bacterial Polyesters . . . Polymer Properties"; J. Polym. Sci. Part A: Polymer Chemistry, 36, 2381–2387 (1998).

Takagi, et al.; "Biosynthesis . . . putida"; Macromolecules (1999) 32, 8315–8318.

Fitzsche, et al.; "An Unusual Bacterial Polyester . . . Group"; Makromol Chem., 191, 1952–1965 (1990).

Kim, et al.; "Preparation and Characterization of Poly (β–hydroxyalkanoates) and n–alkenoic Acids"; Macromolecules, 1991, 24, 5256–5260.

Lytle, et al.; "Filtration Sizes . . . Barrier Materials"; Appl. & Environm. Microbiol., 1992, 58, 2, 747–749.

Ritter, et al.; Bacterial Production of Polyesters . . . Chains, Macromol. Chem. Phys. 195, 1665–1672 (1994).

Kim, et al.; Bioengineering of poly(β–hydroxyalkanoates . . . Substituents) Can. J. Microbiol. 41, (Suppl. 1): 32–43 (1995).

Arostegui, et al.; "Bacterial Polyesters . . . Nitrophenyl groups"; Macromolecules, 32, 9, (1999) 2889–2895.

POLYHYDROXYALKANOATES HAVING IN ITS SIDE CHAIN PHENYLSULFINYL STRUCTURE AND/OR PHENYL SULFONYL STRUCTURE AND PRODUCTION PROCESS THEREFOR; CHARGE CONTROL AGENT, TONER BINDER AND TONER CONTAINING SAME; AND IMAGE FORMING METHOD AND IMAGE FORMING APPARATUS USING THE TONER

BACKGROUND OF THE INVENTION

1. Field of the Invention

The present invention relates to a polyhydroxyalkanoate (hereinafter simply "PHA") containing a novel structural unit and a production process thereof. More specifically, the present invention is directed to a process for producing a novel PHA containing a 3-hydroxyalkanoic unit which has a substituted phenylsulfinyl group and/or a substituted phenylsulfonyl group as a substituent at the end of its side chain, in which microorganisms capable of producing a PHA are cultured to produce and accumulate in the cell the PHA containing the 3-hydroxyalkanoic unit having the corresponding substituted phenylsulfanyl group as a substituent, and a sulfide-type sulfur in the PHA is selectively oxidized and converted into a sulfinyl or sulfonyl group, producing the desired PHA which is biodegradable.

This invention further relates to a charge control agent; a toner binder and a toner for developing electrostatic latent images, used in recording processes which utilize electrophotography, electrostatic recording, magnetic recording or the like, an image-forming method making use of the toner, and an image-forming apparatus therefor. More particularly, it relates to a charge control agent, a toner binder and a toner for developing electrostatic latent images, used in electrophotographic, electrostatic-recording and electrostatic-printing apparatus such as copying machines, printers and facsimile machines, an image-forming method making use of the toner, and an image-forming apparatus therefor. Still more particularly, it relates to a negatively charging charge control agent having higher safety for the human body and environment, a toner binder and a toner for developing electrostatic latent images, making use of such a charge control agent, an image-forming method making use of the toner, and an image-forming apparatus therefor.

2. Related Background Art

It has hitherto been reported that many microorganisms produce poly-3-hydroxybutyric acid (PHB) or other PHAs and accumulate it in the cell ("Handbook of Biodegradable Plastics", Biodegradable-Plastic Institute, K.K. N.T.S, pp.178–197, 1995). Like conventional plastics, these polymers can be utilized for the production of various products by melt processing or the like. Also, since they are biodegradable, they have an advantage of being completely broken down by microorganisms in the natural world, and by no means remain in natural environment to cause pollution unlike many conventional synthetic polymeric compounds. They also have superior adaptability to living bodies and are expected to be applicable as medical flexible members.

It is known that such PHAs produced by microorganisms may have various compositions and structures depending on types of microorganisms used for its production, the composition of culture medium, the conditions for culture and so forth. Researches on how to control such compositions and structures have hitherto chiefly been made from the viewpoint of the improvement in physical properties of PHAs.

(1) Biosyntheses of PHAs by the polymerization of a monomer unit having a relatively simple structure such as 3-hydroxybutyric acid (hereinafter simply "3HB"), include the following:

(a) Those which involve 3HB and 3-hydroxyvaleric acid (hereinafter "3HV"):
Japanese Patent Publications No. 6-15604, No. 7-14352, No. 8-19227, etc., and Japanese Patent Application Laid-Open No. 5-7492.

(b) Those which involve 3HB and 3-hydroxyhexanoic acid (hereinafter "3HHx"):
Japanese Patent Application Laid-Open No. 5-93049 and No. 7-265065.

(c) Those which involve 3HB and 4-hydroxybutyric acid (hereinafter "4HB"):
Japanese Patent Application Laid-Open No. 9-191893.

(d) Those which involve 3-hydroxyalkanoates having 6 to 12 carbon atoms:
Japanese Patent No. 2642937.

(e) Biosynthesis utilizing a single fatty acid as a carbon source. Products are substantially the same as those of (d); Appl. Environ. Microbiol., 58(2), 746, 1992.

All these are PHAs which are comprised of monomer units having an alkyl group in the side chain, i.e., "usual PHA", and produced through β-oxidation of hydrocarbons or synthesis of fatty acids from saccharides by the aid of microorganisms.

(2) When, however, broader application of such PHAs produced by microorganisms, e.g., application as functional polymers is taken into account, a PHA in which a substituent other than an alkyl group has been introduced in the side chain, i.e., "unusual PHA" is expected to be very useful. Examples of such a substituent may include those containing aromatic rings (such as a phenyl group and a phenoxy group), and unsaturated hydrocarbons, an ester group, an allyl group, a cyano group, halogenated hydrocarbons and epoxides. Of these, researches are enthusiastically made especially on PHAs having aromatic rings.

(a) Those which contain a phenyl group or a partially substituted phenyl group:
Macromol. Chem. Phys., 191, 1957–1965 (1990) and Macromolecules, 24, 5256–5260 (1991) report that *Pseudomonas oleovorans* produces a PHA containing 3-hydroxy-5-phenylvaleric acid as a unit, using 5-phenylvaleric acid as a substrate.

Macromolecules, 29, 1762–1766 (1996) reports that *Pseudomonas oleovorans* produces a PHA containing 3-hydroxy-5-(4'-tolyl)valeric acid as a unit, using 5-(4'-tolyl)valeric acid as a substrate.

Macromolecules, 32, 2889–2895 (1999) reports that *Pseudomonas oleovorans* produces a PHA containing 3-hydroxy-5-(2', 4'-dinitrophenyl)valeric acid and 3-hydroxy-5-(4'-nitrophenyl)valeric acid as units, using 5-(2', 4'-dinitrophenyl)valeric acid as a substrate.

(b) Those which contain a phenoxyl group or a partially substituted phenoxyl group:
Macromol. Chem. Phys., 195, 1665–1672 (1994) reports that *Pseudomonas oleovorans* produces a PHA copolymer of 3-hydroxy-5-phenoxyvaleric acid with 3-hydroxy-9-phenoxynonanoic acid, using 11-phenoxyundecanoic acid as a substrate.

Japanese Patent No. 2989175 discloses inventions which are concerned with a homopolymer comprised of 3-hydroxy-5-(monofluorophenoxy)pentanoate (3H5(MFP)

P) units or 3-hydroxy-5-(difluorophenoxy)pentanoate (3H5 (DFP)P) units, and a copolymer containing at least the (3H5(MFP)P) unit or the (3H5(DFP)P) unit; *Pseudomonas putida* capable of synthesizing such polymers; and processes for producing the above polymers by the use of the genus *Pseudomonas*. It is reported that, as the effect, a polymer having a phenoxyl group substituted at the side-chain terminal with 1 or 2 fluorine atom(s) can be synthesized by assimilating a long-chain fatty acid having a substituent and that stereo-regularity (isotacticity) and water repellency can be imparted while having a high melting point and retaining good processability.

In addition to such fluorine-substituted products, cyano-group- or nitro-group-substituted products are also being researched.

Can. J. Microbiol., 41, 32–43 (1995) and Polymer International, 39, 205–213 (1996) report that a PHA containing 3-hydroxy-p-cyanophenoxyhexanoic acid or 3-hydroxy-p-nitrophenoxyhexanoic acid as a monomer unit is produced using octanoic acid and p-cyanophenoxyhexanoic acid or p-nitrophenoxyhexanoic acid as a substrate by the use of *Pseudomonas oleovorans* strain ATCC 29347 and *Pseudomonas putida* strain KT 2442.

These reports are useful in order to obtain polymers which, differently from commonly available PHAs having an alkyl group in the side chain, all have an aromatic ring in the side chain, and have physical properties arising therefrom.

(3) Without being confined merely to changes in physical properties, research in a new category is being conducted to produce a PHA having a suitable functional group in the side chain.

For example, Macromolecules, 31, 1480–1486 (1996) and Journal of Polymer Science: Part A: Polymer Chemistry, 36, 2381–2387 (1998) report that a PHA containing at the side-chain terminal a unit having a vinyl group is synthesized, then the product synthesized is epoxidized with an oxidizing agent, thereby a PHA containing a highly reactive epoxy group at the side-chain terminal can be synthesized.

Besides the vinyl group, as an example of synthesizing a PHA containing a unit having a thioether (—S—; a sulfanyl linkage), which is expected to provide a high reactivity, *Pseudomonas putida* strain 27N01 produces a PHA copolymer of 3-hydroxy-5-thiophenoxyvaleric acid (3-hydroxy-5-(phenylsulfanyl)valeric acid) with 3-hydroxy-7-thiophenoxyheptanoic acid (3-hydroxy-7-(phenylsulfanyl) heptanoic acid), using 11-thiophenoxyundecanoic acid (11-(phenylsulfanyl)undecanoic acid) as a substrate.

A number of methods are conventionally known as methods for electrophotography. In general, copied images are obtained by forming an electrostatic latent image on an image-bearing member (photosensitive member) by utilizing a photoconductive material and by various means, subsequently developing the latent image by the use of a toner to form a visible image (toner image), transferring the toner image to a transfer medium as the occasion demands, then fixing the toner image to the transfer medium by heating and/or pressing. As methods by which the electrostatic latent image is formed into a visible image, cascade development, magnetic brush development, pressure development and so forth are known in the art. Another method is also known in which, using a magnetic toner and a rotary developing sleeve provided with magnetic poles at the core, the magnetic toner is caused to fly from the developing sleeve to the photosensitive member by the aid of an electric field.

As development methods used when electrostatic latent images are developed, available are a two-component development method making use of a two-component type developer comprised of a toner and a carrier and a one-component development method making use of a one-component developer using no carrier and comprised of only a toner.

Fine colored particles commonly called a toner are composed of a binder resin and a colorant as essential components and optionally a magnetic material and so forth. In order to impart electric charges to the toner, the charging properties of the binder resin itself may be utilized without the use of any charge control agent, but the binder resin has poor charging stability with time and poor moisture resistance, hence a charge control agent is usually added for the purpose of charge retention and charge control of the toner.

Charge control agents nowadays known in the present technical field include, e.g., as negative charge control agents, azo dye metal complexes, metal complexes of aromatic dicarboxylic acids and metal complexes of salicylic acid derivatives. Also, known as positive charge control agents are Nigrosine dyes, triphenylmethane dyes, organotin compounds such as quaternary ammonium salt dibutyltin oxides of various types, and so forth. Toners containing any of as charge control agents, however, do not necessarily satisfy quality characteristics requisite for toner such as charging performance and stability with time in some cases.

For example, toners containing the azo dye metal complexes known as negative charge control agents are on a reasonable level in respect of the highness of charge quantity. However, since the azo dye metal complexes are crystal compounds with a low molecular weight, they may have a poor dispersibility depending on types of binder resins to be incorporated. In such a case, the negative charge control agents are not uniformly distributed in the binder resins, and the resultant toners also have a charge quantity distribution greatly lacking for sharpness, so that the images to be obtained may have a low gradation, showing a poor image formation performance. Moreover, the azo dye metal complexes have color tone specific thereto, and hence, under the existing conditions, they are used only in toners with hues limited mainly to black. When such toners are used as color toners, a serious problem arises in that they do not have the clearness necessary for producing images with enhanced color definition.

As examples of nearly colorless negative charge control agents, metal complexes of aromatic dicarboxylic acids are named, but may have a problem of low dispersibility because they are not perfectly colorless and they are crystal compounds with a low molecular weight.

As for the Nigrosine dyes and the triphenylmethane dyes, known as positive charge control agents, they stand colored in themselves, hence under the existing conditions, they are used only in toners with hues limited mainly to black. The toners containing such dyes may have poor stability over time when used in continuous copying. Conventional toners containing quaternary ammonium salts may insufficient moisture resistance, and may be so poor in stability over time as not to afford good images during repeated use.

In recent years, a worldwide discussion has emerged from the environmental conservation viewpoint concerning how waste should be curtailed and how the safety of waste should be improved; which is also applicable to the field of electrophotography. With the wide spread use of image-forming apparatus, the disposal of printed paper, waste toner and the like is increasing year by year, and the safety of such waste is also an important subject from the standpoint of global environmental conservation.

Taking into account such a point, studies are being made on polymer type charge control agents. They include compounds disclosed in, e.g., U.S. Pat. Nos. 4,480,021, 4,442,189 and 4,925,765 and Japanese Patent Application Laid-Open No. 60-108861, No. 61-3149, No. 63-38958 and No. 63-88564. In general, as polymer charge control agents used for toners exhibiting negative chargeability, there are frequently employed polymer compounds having ammonium salt type functional groups, such as copolymers of styrene and/or α-methylstyrene with quaternary ammonium alkyl (meth)acrylates (Japanese Patent Application Laid-Open No. 8-220809, Japanese Patent Publication No. 8-3658, and Japanese Patent No. 2552133 and No. 2807796) and polyamide-modified polyester polymers using polyvalent amines as part of the structure of polyester resin composed of dicarboxylic units and glycol units (Japanese Patent Publication No. 4-46424). Such materials are advantageous in that they are colorless, but should be added in a large amount to ensure charge quantity, besides nitrogen atoms are thermally unstable and may be oxidized and heat-decomposed at the time of heat-kneading to cause a noxius odor or coloring.

In order to solve such problems, Japanese Patent Publication No. 7-120080 discloses positively chargeable polymer charge control agents composed of copolymers of phosphonium salts of vinylbenzyl halide. However, all these have a cationic functional group with a positive charge, hence apparently have moisture-absorption characteristics and thus is considered to have poor moisture resistance. In addition, a problem may arise in compatibility with binder resins which are basically nonionic.

Thus, these compounds do not have any sufficient performance as charge control agents, and have problems on charge quantity, charging-rise performance, stability with time, environmental stability and so forth. Considering not only the function but also influence on the human body, there is a strong desire to find a charge control agent which can be synthesized through safer and milder processes using safer compounds and smaller amounts of organic solvents.

From the viewpoint of environmental conservation, development is being made on resins degradable over time by the action of microorganisms, i.e., biodegradable resins. For example, as stated previously, it has been reported that many microorganisms are capable of producing the biodegradable resin PHA and accumulating it in the cell. It is known that such PHA can have various compositions and structures depending on types of microorganisms used for production, medium compositions, culture conditions and so forth. Researches have hitherto chiefly been made on how to control such compositions and structures from the viewpoint of the improvement in physical properties of PHA and have already gotten considerable achievement especially in the application to the field of materials for medical use. In the field of agriculture, too, the biodegradable resins are used in multifiles, gardening material and so forth, and also in sustained-release agricultural chemicals, fertilizers and so forth. Also in the field of leisure industry, the biodegradable resins are used in fishing lines, fishing articles, golf goods and so forth.

However, considering the wide spread application as plastics, under the existing conditions they can not still be said to be satisfactorily in respect of physical properties. In order to make a PHA utilizable in a much wider range, it is important to more extensively study the improvement of physical properties. For that end, it is essential to research and development PHAs containing monomer units of various structures. The PHA of the type having a substituent introduced in its side chain can be expected to be expanded as a "functional polymer" having very useful functions and properties attributable to the properties of the substituent introduced, by selecting the substituent to be introduced according to the desired properties and so forth. Namely, it is also an important subject to research and develop such a PHA as can achieve both of such functionality and the biodegradability.

In the field of electrophotography, too, the application of biodegradable resins to binder resins is proposed especially in the production of toners. For example, U.S. Pat. No. 5,004,664 discloses a toner having as its composition a biodegradable resin, in particular, polyhydroxybutyric acid, polyhydroxyvaleric acid, or a copolymer or blend of these. Japanese Patent Application Laid-Open No. 6-289644 disclose an electrophotographic toner particularly used for heat-roll fixing, which is characterized in that at least a binder resin contains a vegetable wax and a biodegradable resin (as exemplified by polyesters produced by microorganisms and natural polymeric materials derived from vegetables or animals), and the vegetable wax is added to the binder resin in an amount of from 5 to 50% by weight.

Japanese Patent Application Laid-Open No. 7-120975 discloses an electrophotographic toner binder resin. Japanese Patent Application Laid-Open No. 9-274355 discloses a toner for developing electrostatic latent images which is characterized by containing a polyester resin and a colorant; the polyester resin being obtained by dehydration polycondensation of a composition containing lactic acid and a tri- or more functional oxycarboxylic acid.

Japanese Patent Application Laid-Open No. 8-262796 discloses an electrophotographic toner containing a binder resin and a colorant, and is characterized in that the binder resin comprises a biodegradable resin (as exemplified by aliphatic polyester resins) and the colorant comprises a water-insoluble coloring matter. Japanese Patent Application Laid-Open No. 9-281746 still also discloses a toner for developing electrostatic latent images which is characterized by containing a urethanated polyester resin and a colorant; the urethanated polyester resin being obtained by cross-linking polylactic acid with a tri- or more functional polybasic isocyanate.

In all the electrophotographic toners stated above, biodegradable resins are used as their binder resins, and they are understood to have the effect of contributing to environmental conservation.

However, no examples in which biodegradable resins are used in charge control agents have been reported and there is plenty of room for further contribution to environmental conservation.

Among these PHAs having a functional group in the side chain, taking notice of a PHA containing a 3-hydroxy-ω-(phenylsulfanyl)alkanoic unit, its sulfide type sulfur (—S—) is highly reactive, hence it is forecasted in the development of functional PHAs that studies are increasingly made on various derivatives of PHAs having the sulfide type sulfur (—S—). However, so far there is only the aforementioned report on the biosynthesis of the PHA having an aromatic ring and a sulfide type sulfur (—S—). In addition, The production process of the above PHA containing a 3-hydroxy-ω-(phenylsulfanyl)alkanoic unit uses as a raw material ω-(phenylsulfanyl)alkanoic acid whose carbon chain length is longer than that of units of the objective PHA, utilizes a β oxidation system in which the carbon chain is shortened two carbons by two carbons, and allows 3-hydroxyalkanoic acid having a carbon chain shorter than the raw material to be incorporated in the polymer unit, hence has such a problem that the polymer structure is difficult to control.

To solve the problem, the present inventors have already developed processes for producing PHAs primarily containing 3-hydroxy-ω-(phenylsulfanyl)alkanoic units retaining the carbon chain length of ω-(phenylsulfanyl)alkanoic acid as a raw material, the processes having been filed as Japanese Patent Application No. 2001-57145 and No. 2001-57142. These two applications disclose novel polyhydroxyalkanoates containing units having a sulfide (—S—) structure in the side chain and efficient production process thereof. Specifically, the processes use microorganisms and produce PHA molecules which have a carbon chain corresponding to the raw material and a unit structure having in its terminal a phenylsulfanyl group or a substituted phenylsulfanyl group and in which a sulfide type sulfur with high reactivity (—S—) is present. There is a strong desire for suggestions concerning means for converting from a structure containing the sulfide type sulfur with high reactivity (—S—) to a useful PHA having different physicochemical properties by utilizing its reactivity and the novel PHA produced using the above noted means.

SUMMARY OF THE INVENTION

The present invention was made to solve the aforementioned problems and an object of the present invention is to provide, rather than the PHA containing a unit having a sulfide type sulfur (—S—) in its side chain, a new PHA applicable to further wide spread use, specifically, a PHA with a new structure capable of improving physicochemical properties and a production process thereof. In particular, the present invention provides a novel PHA produced by using as an intermediate raw material a PHA mainly containing a 3-hydroxy-ω-(phenylsulfanyl)alkanoic unit and/or a 3-hydroxy-ω-(substituted phenylsulfanyl)alkanoic unit, which is produced by microorganisms, and converting its sulfide type sulfur (—S—) to a group having another type of sulfur and a production process thereof.

Another object of the present invention is to provide a positively chargeable charge control agent which, as for its function, is more contributive to environmental conservation and has high performance (large charge quantity, quick rise of charging, superior stability over time, high environmental stability) and improved dispersibility, a toner binder containing the charge control agent, a static image developing toner containing the charge control agent, and an image forming method and an image forming apparatus using the static image developing toner.

As a result of enthusiastic research on the solution of the above problems, the present inventors found that when using as a raw material a PHA mainly containing a 3-hydroxy-ω-(phenylsulfanyl)alkanoic unit and/or a 3-hydroxy-ω-(substituted phenylsulfanyl)alkanoic unit, which is produced by microorganisms, and selectively oxidizing its sulfide type sulfur (—S—) with a peroxide, the sulfide type sulfur is converted to a sulfonyl group (—SO$_2$—) or a sulfinyl group (—SO—), and the resulting PHA has a novel structure and enhanced physicochemical properties. In addition, they found that instead of conducting the above oxidation treatment after allowing microorganisms to produce a PHA mainly containing a 3-hydroxy-ω-(phenylsulfanyl)alkanoic unit and/or a 3-hydroxy-ω-(substituted phenylsulfanyl) alkanoic unit as an intermediate material from ω-(phenylsulfanyl)alkanoic acid and/or ω-(substituted phenylsulfanyl)alkanoic acid as a raw material and once recovering the produced PHA through processes of separation and purification by solvent extraction, the oxidation also can be carried out using a peroxide after disrupting the cells and separating the PHA accumulated therein, thereby producing the objective PHA containing the unit having a sulfonyl group (—SO$_2$—) and/or the unit having a sulfinyl group (—SO—). Based on the above findings, they brought the present invention to completion.

Therefore, the present invention provides a polyhydroxyalkanoate containing in its polymer molecule at least one unit of a 3-hydroxy-(substituted phenylsulfinyl)alkanoic acid unit of the general formula (1) below:

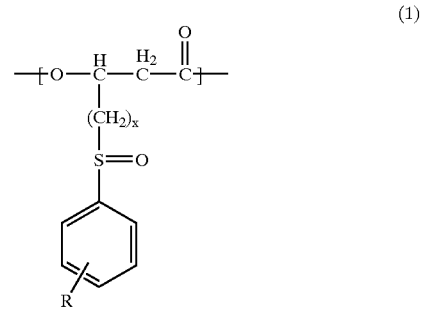

(1)

x = 1–7

(wherein R is H, halogen, CN, NO$_2$, COOR' or SO$_2$R" (where R' is H, Na, K, CH$_3$ or C$_2$H$_5$, and R" is OH, ONa, OK, halogen atom, OCH$_3$ or OC$_2$H$_5$) and x denotes any one of integers from 1 to 7 provided that it may take one or more different values in the polymer) and a 3-hydroxy-(substituted phenylsulfonyl)alkanoic acid unit of the general formula (2) below:

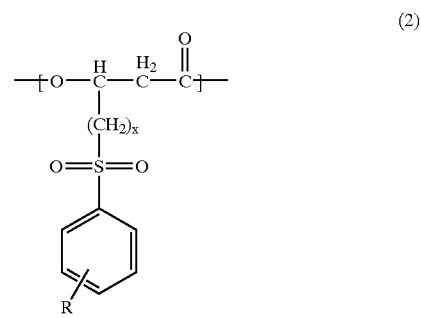

(2)

x = 1–7

(wherein R is H, halogen, CN, NO$_2$, COOR' or SO$_2$R" (where R' is H, Na, K, CH$_3$ or C$_2$H$_5$ and R" is OH, ONa, OK, halogen atom, OCH$_3$ or OC$_2$H$_5$) and x denotes any one of integers from 1 to 7 provided that it may take one or more different values in the polymer).

The polyhydroxyalkanoate according to the present invention may contain in the polymer molecule thereof not only at least one of the units of the general formulae (1) and (2), but also a 3-hydroxy-(substituted phenylsulfanyl) alkanoic unit of the general formula (3) below:

(3)

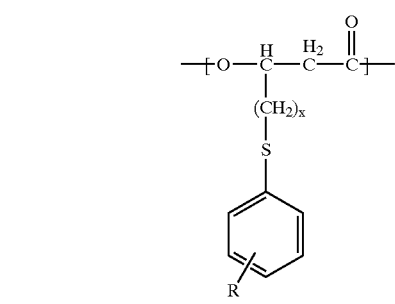

x = 1–7

(wherein R is H, halogen, CN, NO$_2$, COOR' or SO$_2$R" (where R' is H, Na, K, CH$_3$ or C$_2$H$_5$ and R" is OH, ONa, OK, halogen, OCH$_3$ or OC$_2$H$_5$) and x denotes any one of integers from 1 to 7 provided that it may take one or more different values in the polymer).

Further, the polyhydroxyalkanoate according to the present invention may contain in the polymer molecule thereof not only at least one of the units of the general formulae (1) and (2) and the unit of general formula (3), but also a 3-hydroxyalkanoic unit of the general formula (4) below:

(4)

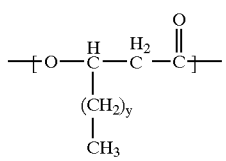

y = 0–8

(wherein y denotes any one of integers from 0 to 8, provided that plural (y)s may take one or more values in the polymer) and/or a 3-hydroxyalk-5-enoic unit of the general formula (5):

(5)

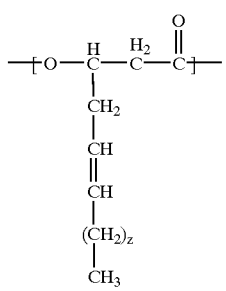

z = 3,5

(wherein z denotes any one of integers from 3 and 5 provided that it may take one or more values in the polymer).

In the PHA of the above-mentioned structure, the polyhydroxyalkanoate may be composed of polymer molecules having a number average molecular weight within the range of 1,000 to 500,000. In the PHA of the present invention, its 3-hydroxyalkanoic acid unit has an asymmetric carbon atom at the 3-position, so that optical isomers exist. That is, the PHA of the present invention may take an R-form, S-form or racemi-form depending on the absolute configuration of the carbon atom at the 3-position. However, the use of the production process according to the present invention as described later on results in the same absolute configuration, specifically, the R-form that exhibits biodegradability for all the units and therefore is more preferable.

The PHA of the present invention in one aspect is a polyhydroxyalkanoate containing in the polymer molecule thereof at least one unit selected from the group consisting of a 3-hydroxy-5-(phenylsulfinyl)valeric acid unit of the chemical formula (6) below:

(6)

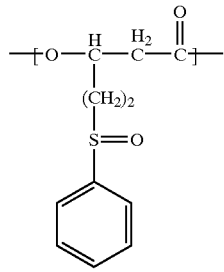

and a 3-hydroxy-5-(phenylsulfonyl)valeric acid unit of the chemical formula (7) below:

(7)

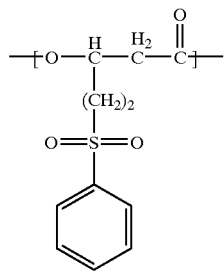

Here, the PHA may contain in the polymer molecule thereof a 3-hydroxy-5-(phenylsulfanyl)valeric acid unit of the chemical formula (8) below:

(8)

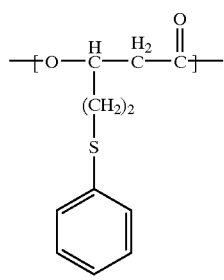

in addition to the unit(s) of the chemical formulae (6) and/or (7) above.

The PHA of the present invention in still another aspect is a polyhydroxyalkanoate containing in the polymer molecule thereof at least one unit selected from the group consisting of a 3-hydroxy-4-(phenylsulfinyl)butyric acid unit of the chemical formula (9) below:

(9)

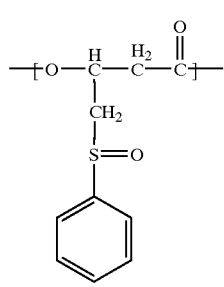

and a 3-hydroxy-4-(phenylsulfonyl)butyric acid unit of the chemical formula (10) below:

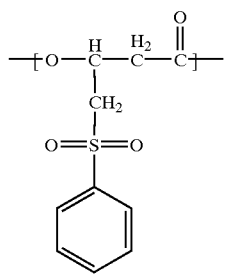

(10)

Here, the PHA may contain in the polymer molecule thereof a 3-hydroxy-4-(phenylsulfanyl)butyric acid unit of the chemical formula (11) below:

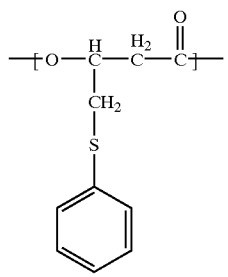

(11)

in addition to the unit(s) of the chemical formulas (9) and/or (10) above.

The PHA of the present invention in still another aspect is a polyhydroxyalkanoate comprising in the polymer molecule thereof at least one unit selected from the group consisting of a 3-hydroxy-5-[(4-fluorophenyl)sulfinyl]valeric acid unit of the chemical formula (12) below:

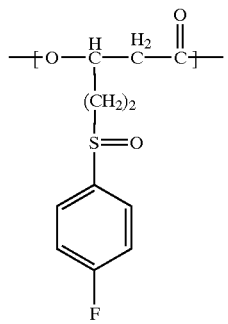

(12)

and a 3-hydroxy-5-[(4-fluorophenyl)sulfonyl]valeric acid unit of the chemical formula (13) below:

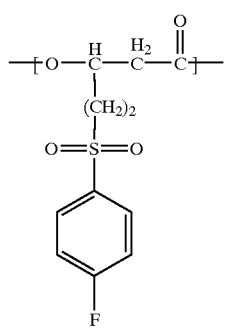

(13)

Here, the PHA may contain in the polymer molecule thereof a 3-hydroxy-5-[(4-fluorophenyl)sulfanyl]valeric acid unit of the chemical formula (14) below:

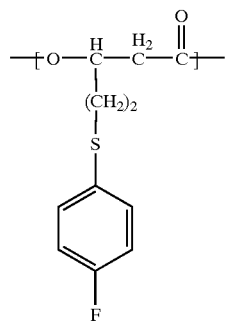

(14)

in addition to the unit(s) of the chemical formulas (12) and/or (13) above.

The PHA of the present invention in still another aspect is a polyhydroxyalkanoate containing the polymer molecule thereof at least one unit selected from the group consisting of a 3-hydroxy-5-[(3-fluorophenyl)sulfinyl]valeric acid unit of the chemical formula (15) below:

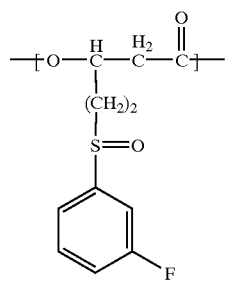

(15)

and a 3-hydroxy-5-[(3-fluorophenyl)sulfonyl]valeric acid unit of the chemical formula (16) below:

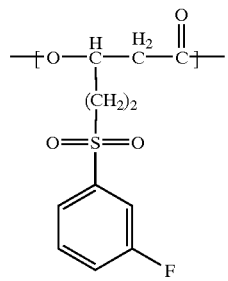

(16)

Here, the PHA may contain in the polymer molecule thereof a 3-hydroxy-5-[(3-fluorophenyl)sulfanyl]valeric acid unit of the chemical formula (17) below:

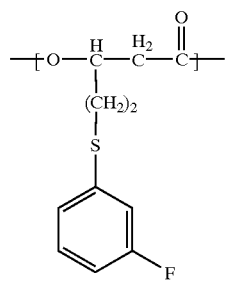

(17)

in addition to the unit(s) of the chemical formulas (15) and/or (16) above.

Further, according to the present invention, there is also provided a method for producing the above-mentioned PHA of the present invention, that is, the invention relates to a method for producing a polyhydroxyalkanoate which has any one of the above-mentioned structures, comprising:

(Step 1) culturing a microorganism in a medium containing at least one ω-(substituted phenylsulfanyl)alkanoic acid of a general formula (18) below:

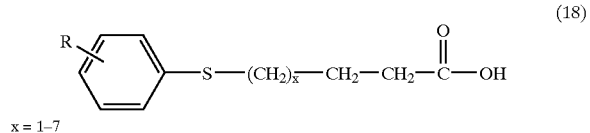

x = 1–7

(wherein R is H, halogen, CN, $NO_2$, COOR', or $SO_2R''$ (where R' is H, Na, K, $CH_3$ or $C_2H_5$ and R" is OH, ONa, OK, halogen, $OCH_3$ or $OC_2H_5$) and x denotes any one of integers from 1 to 7); and (Step 2) treating a polyhydroxyalkanoate produced by the microorganism cultured in Step 1 with a peroxide compound.

In the method as described above, each of the units of the general formulae (1), (2) and (3) contained in the PHA have the relationships with the starting compounds of the general formula (18) as described below. First, the substituent R on the benzene ring of the starting compound of the general formula (18) is substantially retained as the substituent group R on the benzene ring of each unit of the general formulae (1), (2) or (3). Secondly, the units of the general formulas (1) and (2) are converted from the unit of the general formula (3) contained in the PHA prepared in Step 1 and the carbon numbers x of the side chains of the three units are identical with each other. Thirdly, the unit of the general formula (3) contained in the PHA prepared in Step 1 is produced by the process of β-oxidation from the starting compound of the general formula (18) and the x in the unit of the general formula (3) is identical with the x in the unit of the general formula (18) or may in some cases be an integer smaller than the x in the general formula (18) by a multiple of 2 as β-oxidation proceeds. Also, the x's in the units of the general formulae (1) and (2), depending on the x in the unit of the general formula (3), are identical with the x in the unit of the general formula (18) or may in some cases be an integer smaller than the x in the unit of the general formula (18) by a multiple of 2.

In the method of producing PHA according to the present invention, it is preferable that the peroxide compound used in Step 2 is at least one peroxide compound selected from the group consisting of hydrogen peroxide, sodium percarbonate, metachloroperbenzoic acid, performic acid, and peracetic acid.

In the method of producing PHA, a step of separating the polyhydroxyalkanoate produced by the microorganism from the microbial cells cultured in Step 1 may be provided between Steps 1 and 2 above.

In addition, the production method of the present invention may comprise a step of disrupting microbial cells during the process of separating polyhydroxyalkanoate from the aforementioned microbial cells. In the step of disrupting the microbial cells, any method may be selected from a supersonic wave disrupting method, a homogenizer method, a bead impact method, a triturating method, a grinding method, and a freezing-thawing method as the means for disrupting the cells.

Alternatively, the method of the present invention may comprise a step of extracting polyhydroxyalkanoate from the microbial cells by using a solvent in which the polyhydroxyalkanoate is soluble during the process of separating polyhydroxyalkanoate from the microbial cells. Here, as the solvent in which polyhydroxyalkanoate is soluble, at least one solvent selected from chloroform, dichloromethane, dioxane, tetrahydrofuran, acetonitrile and acetone may be used.

On the other hand, in the method of producing PHA according to the present invention, it is preferable that the medium used in Step 1 contains polypeptone, and it is also preferable that the medium used in Step 1 contains yeast extract.

Alternatively, it is also preferable that the medium used in Step 1 contains a saccharide. In this case, it is more preferable that the saccharide contained in the medium is at least one compound selected from glyceraldehyde, erythrose, arabinose, xylose, glucose, galactose, mannose and fructose, alditols such as glycerol, erythritol and xylitol, aldonic acids such as gluconic acid, uronic acids such as glucuronic acid, galacturonic acid, disaccharides such as maltose, sucrose and lactose.

In addition, it is also preferable that the medium used in Step 1 contains an organic acid or its salt. In this case, it is preferable that the organic acid or its salt contained in the medium is at least one compound selected from pyruvic acid, malic acid, lactic acid, citric acid, succinic acid, and salts thereof.

Also, it is preferable the medium used in Step 1 contains an amino acid or its salt. In this case, it is desirable that the amino acid or its salt contained in the medium is at least one compound selected from glutamic acid, aspartic acid and salts thereof.

In addition, the medium used in Step 1 may contain a linear alkanoic acid having 4 to 12 carbon atoms or its salt.

In the method of producing PHA according to the present invention, the culture of the microorganism in Step 1 can be performed by a culture method having at least two stages comprising:

(Step 1-1) culturing the microorganism in a medium containing at least one ω-(substituted phenylsulfanyl) alkanoic acid of the general formula (18) above and polypeptone; and subsequently (Step 1-2) further culturing the microorganism cultured in Step 1-1 above in a medium containing at least one ω-(substituted phenylsulfanyl)alkanoic acid of the general formula (18) above and an organic acid or salt thereof. Also, in this case, it is preferable that the organic acid or its salt contained in the medium used in Step 1-2 above is at least one compound selected from pyruvic acid, malic acid, lactic acid, citric acid, succinic acid, and salts thereof.

In the method of producing PHA according to the present invention, it is possible that the culture of the microorganism in Step 1 is performed by a culture method having at least two stages comprising:

(Step 1-3) culturing the microorganism in a medium containing at least one ω-(substituted phenylsulfanyl) alkanoic acid of the general formula (18) above and a saccharide; and subsequently (Step 1-4) further culturing the microorganism cultured in Step 1-3 above in a medium containing at least one ω-(substituted phenylsulfanyl)alkanoic acids of the general formula (18) above and a saccharide. In this case, it is preferable that the saccharide contained in the medium used in Step 1-3 and Step 1-4 above is at least one compound selected from glyceraldehyde, erythrose, arabinose, xylose, glucose, galactose, mannose and fructose, alditols such as glycerol, erythritol and xylitol, aldonic acids such as gluconic acid, uronic acids such as glucuronic acid, galacturonic acid, disaccharides such as maltose, sucrose and lactose.

When employing the aforementioned two-stage culture step, the medium used in the second-stage culture step, specifically Steps 1-2 and 1-4 above, preferably contains no nitrogen source. That is, when a production method is used in which two or more culture steps are provided in Step 1, the productivity of PHA by the microorganism can be improved by controlling the nitrogen source in the medium used in a later-stage culture step, for example, a second stage culture step. The method for the production of PHA according to the present invention in one aspect may be a method of producing a polyhydroxyalkanoate containing in the polymer molecule thereof at least one unit selected from a 3-hydroxy-5-(phenylsulfinyl)valeric acid unit of the chemical formula (6) below:

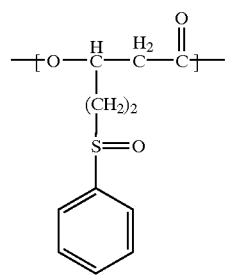

(6)

and a 3-hydroxy-5-(phenylsulfonyl)valeric acid unit of the chemical formula (7) below:

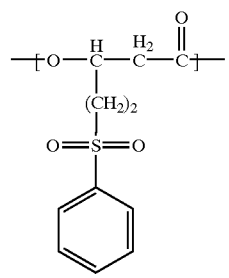

(7)

and optionally a 3-hydroxy-5-(phenylsulfanyl)valeric acid unit of the chemical formula (8) below:

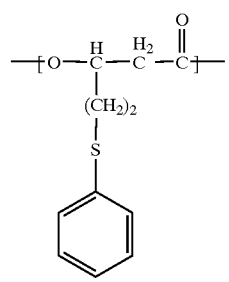

(8)

where the method comprises culturing a microorganism in a medium containing 5-(phenylsulfanyl)valeric acid of the chemical formula (19):

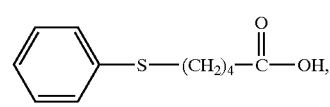

(19)

and treating the polyhydroxyalkanoate produced by the cultured microorganism with at least one peroxide compound selected from hydrogen peroxide, sodium percarbonate, metachloroperbenzoic acid, performic acid, and peracetic acid.

In addition, the method for the production of PHA according to the present invention in one aspect may be a method of producing a polyhydroxyalkanoate containing in the polymer molecule thereof at least one unit selected from a 3-hydroxy-4-(phenylsulfinyl)butyric acid unit of the chemical formula (9) below:

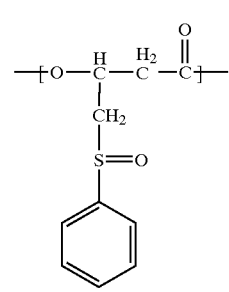

(9)

and a 3-hydroxy-4-(phenylsulfonyl)butyric acid unit of the chemical formula (10) below:

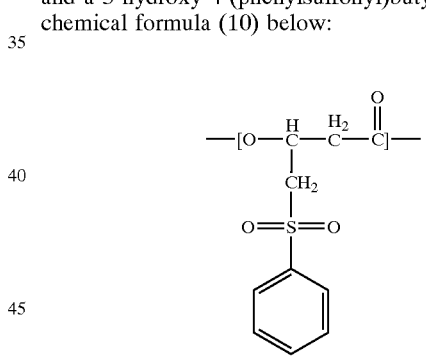

(10)

and optionally a 3-hydroxy-4-(phenylsulfanyl)butyric acid unit of the chemical formula (11) below:

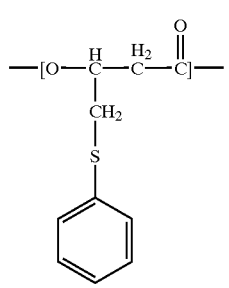

(11)

where the method comprises culturing a microorganism in a medium containing 4-(phenylsulfanyl)butyric acid of the chemical formula (20):

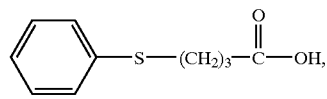

(20)

and treating the polyhydroxyalkanoate produced by the cultured microorganism with at least one peroxide compound selected from hydrogen peroxide, sodium percarbonate, metachloroperbenzoic acid, performic acid, and peracetic acid.

Further, the method for the production of PHA according to the present invention in one aspect may be a method of producing a polyhydroxyalkanoate containing in the polymer molecule thereof at least one unit selected from a 3-hydroxy-5-[(4-fluorophenyl)sulfinyl]valeric acid unit of the chemical formula (12) below:

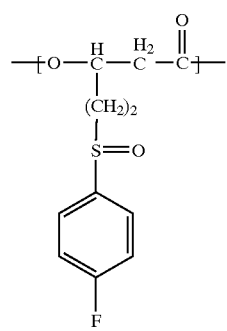

(12)

and a 3-hydroxy-5-[(4-fluorophenyl)sulfonyl]valeric acid unit of the chemical formula (13) below:

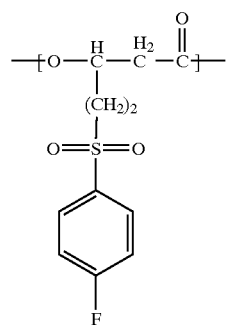

(13)

and optionally a 3-hydroxy-5-[(4-fluorophenyl)sulfanyl]valeric acid unit of the chemical formula (14) below:

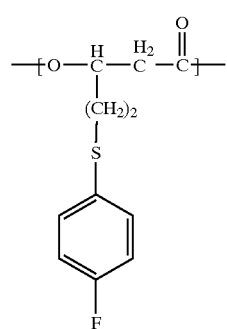

(14)

where the method comprises culturing a microorganism in a medium containing 5-[(4-fluorophenyl)sulfanyl]valeric acid of the chemical formula (21):

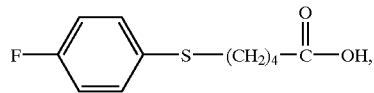

(21)

and treating the polyhydroxyalkanoate produced by the cultured microorganism with at least one peroxide compound selected from hydrogen peroxide, sodium percarbonate, metachloroperbenzoic acid, performic acid, and peracetic acid.

Still further, the method for the production of PHA according to the present invention in one aspect may be a method of producing a polyhydroxyalkanoate containing in the polymer molecule thereof at least one unit selected from the group consisting of a 3-hydroxy-5-[(3-fluorophenyl)sulfinyl]valeric acid unit of the chemical formula (15) below:

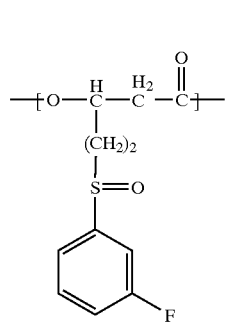

(15)

and a 3-hydroxy-5-[(3-fluorophenyl)sulfonyl]valeric acid unit of the chemical formula (16) below:

(16)

and optionally a 3-hydroxy-5-[(3-fluorophenyl)sulfanyl] valeric acid unit of the chemical formula (17) below:

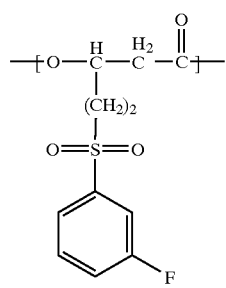

(17)

wherein the method comprises culturing a microorganism in a medium containing 5-[(3-fluorophenyl)sulfanyl]valeric acid of the chemical formula:

(22)

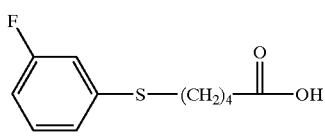

and treating the polyhydroxyalkanoate produced by the cultured microorganism with at least one peroxide compound selected from hydrogen peroxide, sodium percarbonate, metachloroperbenzoic acid, performic acid, and peracetic acid.

In the method of producing PHA according to the present invention, it is preferable that the microorganism producing a polyhydroxyalkanoate in Step 1 is a microorganism belonging to the genus *Pseudomonas*. Here, for example, it is more preferable that the microorganism belonging to the genus *Pseudomonas* is selected from *Pseudomonas cichorii* strain YN2 (FERM BP-7375), *Pseudomonas cichorii* strain H45 (FERM BP-7374), and *Pseudomonas jessenii* strain P161 (FERM BP-7376).

Further, the present inventors have made intensive studies to develop a charge control agent which exhibits high performance and is substantially colorless and finally reached the present invention.

Thus, according to the present invention, there is provided a charge control agent containing at least one unit of monomer units represented by the general formulae (1) and (2) below:

(1)

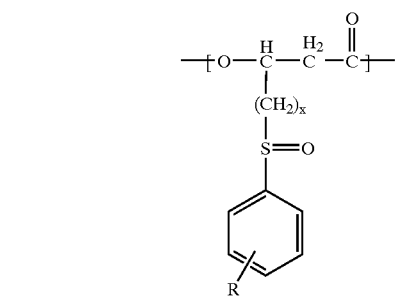

x = 1–7

(2)

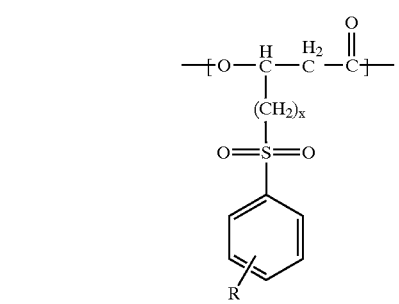

x = 1–7

(wherein R is H, halogen, CN, $NO_2$, COOR', or $SO_2R''$ (where R' represents any one of H, Na, K, $CH_3$ and $C_2H_5$ and R'' represents any one of OH, ONa, OK, halogen, $OCH_3$ and $OC_2H_5$) and x is an integer and may take one or more values within the range indicated in the chemical formula).

The PHA contained in the charge control agent according to the present invention, may contain, in addition to at least one of the units of chemical formulae (1) and (2), a unit of a chemical formula (3) below:

(3)

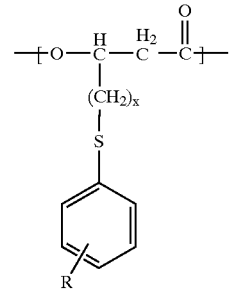

x = 1–7

(wherein R is H, halogen, CN, $NO_2$, COOR', or $SO_2R''$ (where R' represents any one of H, Na, K, $CH_3$ or $C_2H_5$ and R'' represents any one of OH, ONa, OK, halogen, $OCH_3$ or $OC_2H_5$) and x is any integer and may take one or more values within the range indicated in the chemical formula).

The PHA contained in the charge control agent according to the present invention may contain, in addition to at least one of the units of chemical formulae (1)and (2) and the unit of formula (3), at least one of units of chemical formulae (4) and (5) below:

(4)

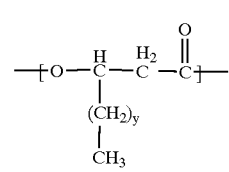

y = 0–8

(5)

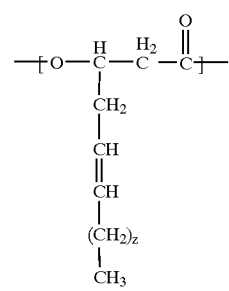

z = 3,5

(wherein y and z are each an integer and may take one or more values independently of the units of the formulae (1), (2) and (3) within the range indicated in the chemical formula):

The polyhydroxyalkanoate contained in the charge control agent according to the present invention has a number average molecular weight in the range from 1,000 to 500,000.

In addition, the present invention relates to a toner binder containing the charge control agent of the present invention.

Further, the present invention relates to an electrostatic charge image developing toner containing at least a binder resin, a colorant and the charge control agent.

Also, the present invention relates to an image forming method including at least the steps of externally applying a voltage to a charging member to charge an electrostatic latent image bearing member, developing the electrostatic charge image by using an electrostatic charge image developing toner to form a toner image on the electrostatic latent image bearing member, transferring the toner image on the electrostatic latent image bearing member to a recording medium, and thermally fixing the toner image on the recording medium, wherein the electrostatic charge image developing toner containing at least a binder resin, a colorant and the charge control agent, is used.

Further, the present invention relates to an image forming method including at least the steps of externally applying a voltage to a charging member to charge an electrostatic latent image bearing member, forming an electrostatic charge image on the charged electrostatic latent image bearing member, developing the electrostatic charge image by using an electrostatic charge image developing toner to form a toner image on the electrostatic latent image bearing member, transferring the toner image on the electrostatic latent image bearing member to an intermediate transfer member in a first stage, transferring the toner image on the intermediate transfer member to a recording medium in a second stage, and thermally fixing the toner image on the recording medium thereto, wherein the electrostatic charge image developing toner containing at least a binder resin, a colorant and the charge control agent, is used.

Also, the present invention relates to an image forming apparatus having at least a means for externally applying a voltage to a charging member to charge an electrostatic latent image bearing member, a means for forming an electrostatic charge image on the charged electrostatic latent image bearing member, a developing means for developing the electrostatic charge image by using an electrostatic charge image developing toner to form a toner image on the electrostatic latent image bearing member, a transfer means for transferring the toner image on the electrostatic latent image bearing member to a recording medium, and a fixing means for thermally fixing the toner image on the recording medium, wherein the electrostatic charge image developing toner containing at least a binder resin, a colorant and the charge control agent, is used.

Furthermore, the present invention relates to an image forming apparatus having at least a means for externally applying a voltage to a charging member to charge an electrostatic latent image bearing member, a means for forming an electrostatic charge image on the charged electrostatic latent image bearing member, a developing means for developing the electrostatic charge image by using an electrostatic charge image developing toner to form a toner image on the electrostatic latent image bearing member, a first transfer means for transferring the toner image on the electrostatic latent image bearing member to an intermediate transfer member, a second transfer means for transferring the toner image on the intermediate transfer member to a recording medium, and a fixing means for thermally fixing the toner image on the recording medium, wherein the electrostatic charge image developing toner containing at least a binder resin, a colorant and the charge control agent, is used.

The method for the production of PHA according to the present invention makes it possible to produce a novel, biodegradable polyhydroxyalkanoate containing at least one unit having a phenylsulfinyl group or phenylsulfonyl group on the side chain thereof by cultivating a microorganism in a medium containing a ω-(phenylsulfanyl)alkanoic acid or a ω-(substituted phenylsulfanyl)alkanoic acid and treating the PHA containing a 3-hydroxy-(phenylsulfanyl)alkanoic acid unit or a 3-hydroxy-(substituted phenylsulfanyl)alkanoic acid unit produced by the microorganism with a peroxide compound to convert the sulfanyl group (—S—) into a sulfinyl group (—SO—) or a sulfonyl group (—SO$_2$—). The obtained PHA can be so made as to be an intermediate raw material, i.e., a PHA in which a 3-hydroxy-(phenylsulfanyl) alkanoic acid unit or a 3-hydroxy-(substituted phenylsulfanyl)alkanoic acid unit derived from a PHA containing a 3-hydroxy-(phenylsulfanyl)alkanoic acid unit or a 3-hydroxy-(substituted phenylsulfanyl)alkanoic acid unit produced by the cultured microorganism partially remains, by controlling the conditions of treatment with the peroxide compound. In addition, the PHA production method according to the present invention can regulate the content ratio of the three units having respectively the phenylsulfinyl group, phenylsulfonyl group and phenylsulfanyl group on the side chains thereof with high reproducibility by controlling the conditions of treatment with peroxide compound and the resulting PHA can be utilized as a useful polyhydroxyalkanoate having new characteristics.

Further, according to the present invention, the addition of at least one compound shown above as charge control agents to an electrostatic charge image developing toner composition can provide an electrostatic charge image developing toner which has excellent charging properties, improved dispersibility of compounds in a toner resin and improved spent properties and which causes no fogging of images and is excellent in transferability at the time of output in an image forming apparatus and is highly suited for electrophotographic processes. Furthermore, the charge control agent used in the present invention is also characterized in that it is colorless or only slightly colored so that any desired coloring agent may be selected depending on the color tone required for color toners and it does not impair at all the color tone that the dye or pigment inherently has. In addition, the electrostatic charge image developing toner of the present invention does not require incineration treatment since it is biodegradable so that it is significantly advantageous to industry in light of prevention of air pollution and global warming.

The above and other objects, effects, features and advantages of the present invention will become more apparent from the following description of embodiments thereof taken in conjunction with the accompanying drawings.

DESCRIPTION OF THE PREFERRED EMBODIMENTS

Figure 1:
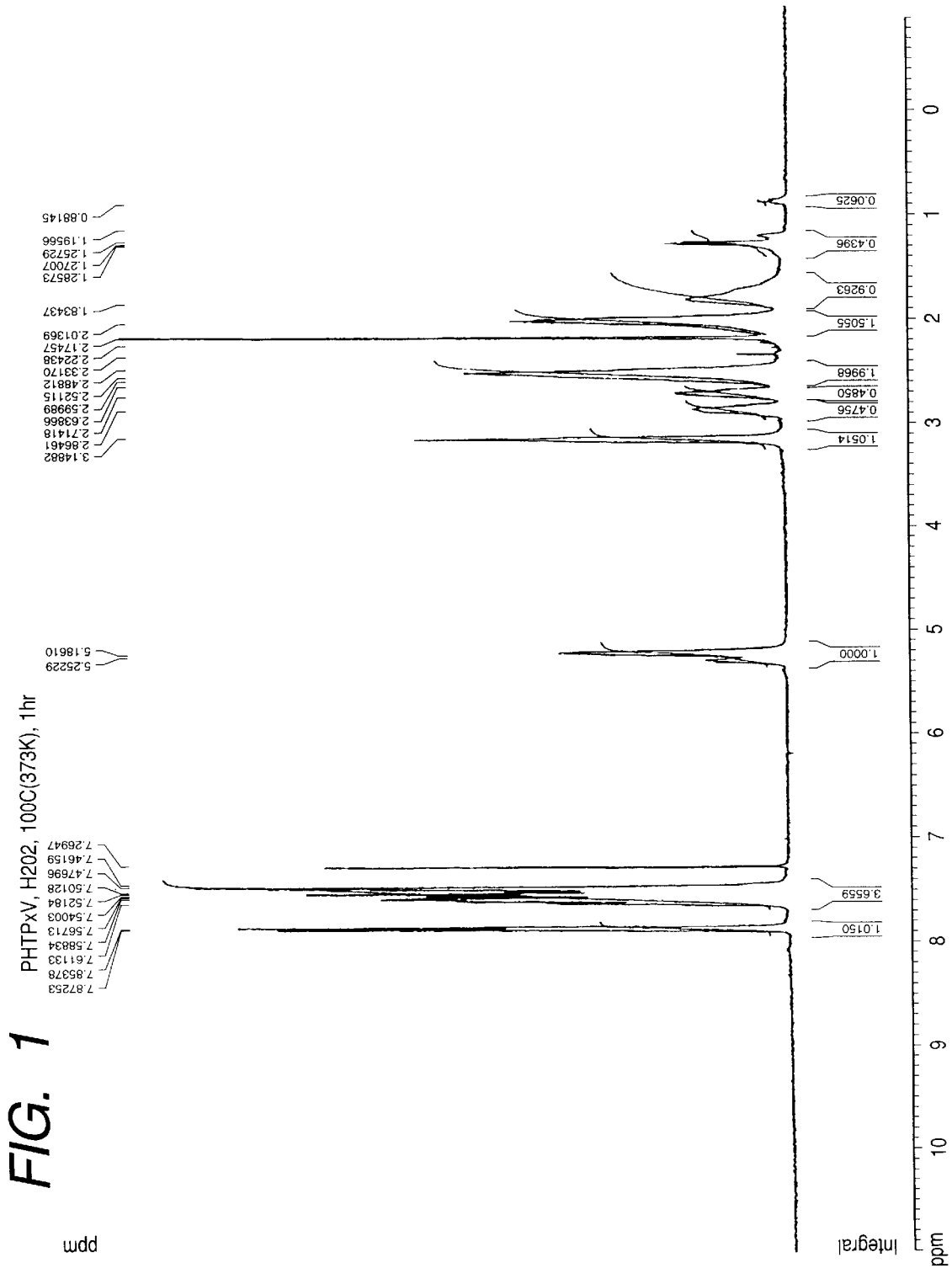
FIG. 1 is a $^1$H-NMR spectrum chart of a PHA containing a unit of the chemical formula (6) and a unit of the chemical formula (7) prepared in Example 1.

The novel polyhydroxyalkanoates of the present invention have at least one of a sulfoxide structure (—SO—) and a sulfone structure (—SO$_2$—) in the monomer unit of hydroxyalkanoate acid contained therein and have physicochemical properties significantly different from those of the known polyhydroxyalkanoate produced by microorganisms due to this structure. The polyhydroxyalkanoates of the present invention are produced through two-stages comprising a step of culturing a microorganism capable of producing PHA in a medium containing a carbon source for growth in addition to an ω-(substituted phenylsulfanyl)alkanoic acid as a raw material carboxylic acid derivative and a step of treating a polyhydroxyalkanoate containing a unit having a substituted phenylsulfanyl group on the terminal of the side chain produced by the microorganism and accumulated in the cells thereof with a peroxide compound. That is, the method for the production of PHA according to the present invention causes a microorganism to produce a PHA containing a unit having a substituted phenylsulfanyl group on the terminal of the side chain as an intermediate raw material and subject the sulfanyl group (—S—) of the unit to selective oxidation treatment with a peroxide compound to convert the PHA to a target PHA having at least one of a sulfoxide structure (—SO—) and a sulfone structure (—SO$_2$—).

Hereinafter, the present invention will be described in more detail.

Carboxylic Acid Derivatives

The ω-(substituted phenylsulfanyl)alkanoic acid used in the present invention are a compound of the general formula (18)

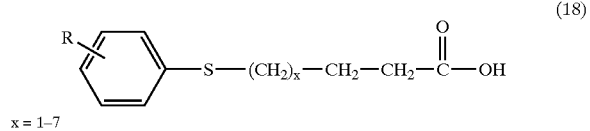

(18)

x = 1-7

(wherein R is H, halogen, CN, NO$_2$, COOR', or SO$_2$R" (where R' is H, Na, K, CH$_3$ or C$_2$H$_5$ and R" is OH, ONa, OK, Halogen, OCH$_3$, or OC$_2$H$_5$) and x is an integer selected from 1 to 7).

The compounds can be obtained, for example, by reacting the compound of the general formula (23)

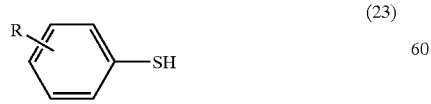

(23)

(wherein R has the same meaning as defined in the general formula (18)) with an ω-bromoalkanoic acid ester to synthesize an ω-(substituted phenylsulfanyl)alkanoic acid ester and then hydrolyzing the ester.

In the method for producing the PHA according to the present invention, the microorganism to be used in producing a precursor PHA used as an intermediate raw material may be any microorganism that produces a PHA containing a 3-hydroxyalkanoic acid unit having a substituted phenylsulfanyl group in the terminal of the side chain and accumulates it in the cell. For example, microorganisms belonging to the genus Pseudomonas having the ability to produce PHA may be exemplified. Examples of preferred microorganisms belonging to the genus Pseudomonas include three strains, i.e., Pseudomonas cichorii strain YN2 (FERM BP-7375), Pseudomonas cichorii strain H45 (FERM BP-7374), and Pseudomonas jessenii strain P161 (FERM BP-7376). The microorganisms of three kinds have been deposited nationally under the mane of the present applicant as the depositor. Thereafter, they have been transferred to a deposit based on the Budapest Agreement, and then deposited in International Patent Organism Depositary of Institute of Advanced Industrial Science and Technology (former National Institute of Bioscience and Human Technology, Agency of Industrial Science and Technology), acting as an international depositary institution under the deposit numbers "FERM BP-7375", "FERM BP-7374", and "FERM BP-7376", respectively. Further, strains having the ability to produce a novel PHA include a microorganism disclosed in Japanese Patent Application No. Hei 11-371863.

There will be given details concerning strains YN2, H45, P91, and P161.

Bacteriological Properties of Strain YN2

(1) Morphological Properties

Shape and size of cells: rod, 0.8 μm×1.5 to 2.0 μm
Polymorphism of cells: negative
Motility: motile
Sporulation: negative
Gram stainability: negative
Colony shape: circular; smooth with entire margin; low upward convex; smooth surface; glossy; translucent (2) Physiological Properties Catalase: positive
Oxidase: positive
O/F test: oxidative (non-fermentative)
Nitrate reduction: negative
Indole production: positive
Acid production from glucose: negative
Arginine dihydrolase: negative
Urease: negative
Esculin hydrolysis: negative
Gelatin hydrolysis: negative
β-Galactosidase: negative
Fluorescent pigment production on King's B agar: positive
Growth under 4% NaCl: positive (weak growth)
Poly-β-hydroxybutyrate accumulation: negative(*)
Tween 80 hydrolysis: positive
(*) Colonies cultured on nutrient agar were stained with Sudan Black for determination.

(3) Ability to Assimilate Substrates

Glucose: positive
L-Arabinose: positive
D-Mannose: negative
D-Mannitol: negative
N-acetyl-D-glucosamine: negative Maltose: negative
Potassium gluconate: positive
n-Caprate: positive
Adipate: negative
dl-Malate: positive
Sodium citrate: positive
Phenylacetate: positive Bacteriogical Properties of Strain H45
   (1) Morphological Properties Shape and size of cells: rod, 0.8 μm×1.0 to 1.2 μm
Polymorphism of cells: negative
Motility: motile
Sporulation: negative
Gram stainability: negative
Colony shape: circular; smooth with entire margin: low upward convex; smooth surface; glossy; cream-colored (2) Physiological Properties Catalase: positive
Oxidase: positive
O/F test: oxidative
Nitrate reduction: negative
Indole production: negative
Acid production from glucose: negative
Arginine dihydrolase: negative
Urease: negative
Esculin hydrolysis: negative
Gelatin hydrolysis: negative
β-Galactosidase: negative
Fluorescent pigment production on the King's B agar: positive
Growth under 4% NaCl: negative
Poly-β-hydroxybutyrate accumulation: negative (3) Ability to Assimilate Substrates Glucose: positive
L-Arabinose: negative
D-Mannose: positive
D-Mannitol: positive
Maltose: negative
N-acetyl-D-glucosamine: positive
Potassium gluconate: positive
n-Caprate: positive
Adipate: negative
dl-Malate: positive
Sodium citrate: positive
Phenyl acetate: positive Bacteriological Properties of Strain P91
   (1) Morpohological Properties Shape and size of cells: rod, 0.6 μm×1.5 μm
Plymorphism of cells: negative
Mobility: motile
Sporulation: negative
Gram staining: negative
Colony shape: circle; entire, smooth margin; low convex; smooth surface; glossy; cream-colored (2) Physiological Properties Catalase: positive
Oxidase: positive
O/F test: oxidative
Nitrate reduction: negative
Indole production: negative
Acid production from glucose: negative
Arginine dihydrolase: positive
Urease: negative
Esculin hydrolysis: negative
Gelatin hydrolysis: negative
β-Galactosidase: negative
Fluorescent pigment production on the King's B agar: positive (3) Substrate Assimilation Glucose: positive
L-Arabinose: negative
D-Mannose: negative
D-Mannitol: negative
N-Acetyl-D-glucosamine: negative
Maltose: negative
Potassium gluconate: positive
n-Caprate: positive
Adipate: negative
dl-Malate: positive
Sodium citrate: positive
Phenyl acetate: positive Bacteriological Properties of the Strain P161

(1) Morphological Properties
Shape and size of cells: spheres, 00.6 μm rods, 0.6 μm×1.5 to 2.0 μm
Polymorphism of cells: positive (elongated form)
Motility: motile
Sporulation: negative
Gram stainability: negative
Colony shape: circle; smooth with entire margin; low upward convex; smooth surface; pale yellow (2) Physiological Properties Catalase: positive
Oxidase: positive
O/F test: oxidative
Nitrate reduction: positive
Indole production: negative
Acid production from glucose: negative
Arginine dihydrolase: positive
Urease: negative
Esculin hydrolysis: negative
Gelatin hydrolysis: negative
β-Galactosidase: negative
Fluorescent pigment production on the King's B agar: positive (3) Ability to Assimilate Substrates Glucose: positive
L-Arabinose: positive
D-Mannose: positive
D-Mannitol: positive
N-acetyl-D-glucosamine: positive
maltose: negative
Potassium gluconate: positive
n-Caprate: positive
Adipate: negative
dl-Malate: positive
Sodium citrate: positive
Phenyl acetate: positive Moreover, it is possible to use, in addition to the microorganisms belonging to *Pseudomonas* sp., those microorganisms that belong to *Aeromonas* sp., *Comamonas* sp., *Burkholderia* sp., etc. and produce PHAs containing 3-hydroxyalkanoic acid units of the general formula (3) by using the substituted alkanoic acid of the general formula (18) as a raw material (substrate).

Culture Step

Step 1 of the method for the production of PHA according to the present invention uses the above-mentioned microorganisms capable of producing PHA to produce PHAs containing 3-hydroxyalkanoic acid units of the general formula (3) having substituted phenylsulfanyl groups on the terminal of the side chains from the corresponding ω-(substituted phenylsulfanyl)alkanoic acids of the general formula (18) as a raw material.

For usual culture of microorganisms to be employed in Step 1, for example, growth for preparation of stock strains, for maintaining the number and activities of the microbial cells required for the production of PHAs, those media that contain components necessary for the growth of the microorganism employed can be selected and used as appropriate. For example, any type of media such as common natural media (bouillon media, yeast extract, etc.) and synthetic media supplemented with a source of nutrients may be used unless they have adverse effects on the growth or viability of the microorganisms. Culture conditions such as temperature, aeration, agitation, and the like are selected as appropriate, depending on the microorganism employed.

On the other hand, in Step 1, when producing PHAs containing a 3-hydroxyalkanoic acid unit of the general formula (3) having a substituted phenylsulfanyl group on the terminal of the side chain thereof by using the above-mentioned PHA producing microorganisms, there may be used as a medium an inorganic medium containing as a raw material for the production of PHAs of interest at least a carbon source for the growth of microorganism in addition to one of the ω-(substituted phenylsulfanyl)alkanoic acid compounds of the general formula (18) that corresponds to the monomer unit of interest and the like. It is desirable that the initial content of the compound of the general formula (18) used as a raw material is selected to be within the range of from 0.01% to 1% (w/v), preferably from 0.02% to 0.2% (w/v), per medium. The ω-(substituted phenylsulfanyl) alkanoic acid of the general formula (18) as a raw material does not always have sufficiently good water solubility due to the structure having an aromatic ring on the terminal in the side chain. However, since the above-mentioned microorganisms are capable of utilizing that compound as a substrate, even if a portion of the ω-(substituted phenylsulfanyl)alkanoic acid in excess of its solubility at the initial stage of culture is partially suspended, it would cause no problem because according as the culture is continued, the microorganisms gradually incorporate that portion in the cell, so that the partially suspended portion is converted and dissolved in the medium.

The compound of the general formula (18) as a raw material may optionally dissolved or suspended as fine suspension in a solvent such as 1-hexadecene or n-hexadecane in order to increase dispersibility and added to the medium. On this occasion, the solvent to be used, such as 1-hexadecene or n-hexadecane, must be added in a concentration of 3% or less (v/v) based on the medium.

In the media, a growth substrate that the microorganisms utilize as the carbon source, etc. is added separately. For the growth substrate, nutrients such as yeast extract, polypeptone, and meat extract may be used. Further, the growth substrate may be appropriately selected from saccharides, organic acids produced as intermediates in the TCA cycle pathway and organic acids produced from the TCA cycle through one or two steps of biochemical reaction or salts thereof, amino acids or salts thereof, linear alkanoic acids having 4 to 12 carbon atoms or salts thereof and so forth, depending on the strain to be used in consideration of their usefulness as the carbon source.

As the saccharides out of a variety of substrates for growth, there may be preferably used one or more compounds selected from aldoses such as glyceroaldehyde, erythrose, arabinose, xylose, glucose, galactose, mannose and fructose, alditols such as glycerol, erythritol and xylitol, aldonic acids such as gluconic acid, uronic acids such as glucuronic acid and galacturonic acid, and disaccharides such as maltose, sucrose and lactose.

As the organic acids or salts thereof, there may be preferably used one or more compounds selected from pyruvic acid, malic acid, lactic acid, citric acid, succinic acid, and salts of these. On the other hand, as for the amino acids or salts thereof, one or more compounds selected from glutamic acid, aspartic acid and salts thereof may be preferably utilized.

Generally, it is more preferred to use polypeptone and saccharides among a variety of substrates for growth. Among the saccharides, it is more preferred to use at least one sugar selected from glucose, fructose and mannose. It is desirable that the content of these substrates for growth per medium is so selected as to be within the range of from 0.1% to 5% (w/v), more preferably from 0.2% to 2% (w/v).

The culture method for production and accumulation of PHA by a microorganism in Step 1 includes a method in which the microorganism is once fully grown and then the microbial cells are transferred to a medium containing a limited nitrogen source such as ammonium chloride and further cultured in a state that a compound that serves as a substrate for the target unit has been added, which method may in some cases increase productivity. For example, a multi-stage system consisting of some stages of steps with the different culture conditions as described above may be adopted.

More specifically, it is more preferred to utilize a two-stage culture method in which as (Step 1-1), a step of culturing a microorganism in a medium containing the compound of the general formula (18) and polypeptone serving as a carbon source is continued during a period of time from the late logarithmic growth phase to the stationary phase, the microbial cells being once recovered by centrifugation or the like, and subsequently as (Step 1-2), a step of further culturing the microbial cells cultured and grown in the preceding Step 1-1 in a medium containing the compound of the general formula (18) and an organic acid or salts thereof serving as a carbon source without containing any nitrogen source is performed, or a two-stage culture method in which as (Step 1-3), a step of culturing a microorganism in a medium containing the compound of the general formula (18) and glucose serving as a carbon source is continued during a period of time from the late logarithmic growth phase to the stationary phase, the microbial cells being once recovered by centrifugation or the like, and subsequently as (Step 1-4), a step of further culturing the microbial cells cultured and grown in the preceding Step 1-3 in a medium containing the compound of the general formula (18) and glucose serving as a carbon source without containing any nitrogen source is performed. In the two-stage culture method, a culture mode is used in which in the first stage, growth of microbial cells is performed in advance while allowing them to produce PHA of the general formula (3) containing 3-hydroxyalkanoic acid unit having a substituted phenylsulfanyl group in the terminal of the side chain from the corresponding ω-(substituted phenylsulfanyl) alkanoic acid of the general formula (18) as the raw material and in the latter stage, as a culture form, the already cultured cells are allowed to mainly produce PHA in a medium containing no nitrogen source, thereby further increasing the amount of PHA accumulated in the cells.

The culture temperature in Step 1 may be any temperature as far as the microorganism strain described above can grow well at that temperature. For example, it is suitable to select the culture temperature within the range of from 15 to 40° C., preferably from 20 to 35° C., more preferably from 20 to 30° C.

The culture may be performed by using any culture method as far as the microorganism utilized can grow therein and produce PHA containing the unit of the general formula (3) from the compound of the general formula (18) as a raw material contained in the medium; for example, liquid culture, solid culture and the like may be used. Further, as far as the raw material, carbon source and oxygen is properly supplied, any type of culture may be used; including, for example, batch, fed batch, semi-continuous, and continuous cultures. For example, the form of liquid batch culture includes a method in which oxygen is supplied by shaking with a shaking flask and an oxygen supply method of an agitation aeration type by using a jar fermenter.

For the inorganic media employed in the above-mentioned culture method, any media can be used, as long as they contain components necessary for microorganisms to grow, such as phosphorus sources (for example, phosphates), nitrogen sources (for example, ammonium salts, nitrates), and the like. Such inorganic media may include, for example, a MSB medium, a M9 medium, and others.

For example, the composition of the M9 medium as an inorganic salt medium employed in Examples described hereinbelow is as follows:

M9 Medium

| | |
|---|---|
| $Na_2HPO_4$: | 6.2 g |
| $KH_2PO_4$: | 3.0 g |
| NaCl: | 0.5 g |
| $NH_4Cl$: | 1.0 g |

(per liter of medium, pH 7.0)

Further, for good growth and concomitant PHA production, indispensable trace elements must be supplemented by adding, for example, the following solution of trace components in an amount of about 0.3% (v/v) to the above-mentioned inorganic salt medium.

Solution of Trace Components

| | |
|---|---|
| Nitrilotriacetic acid: | 1.5 g |
| $MgSO_4$: | 3.0 g |
| $MnSO_4$: | 0.5 g |
| NaCl: | 1.0 g |
| $FeSO_4$: | 0.1 g |
| $CaCl_2$: | 0.1 g |
| $CoCl_2$: | 0.1 g |
| $ZnSO_4$: | 0.1 g |
| $CuSO_4$: | 0.1 g |
| $AlK(SO_4)_2$: | 0.1 g |
| $H_3BO_3$: | 0.1 g |
| $Na_2MoO_4$: | 0.1 g |
| $NiCl_2$: | 0.1 g |

(per liter of medium, pH 7.0)

(Peroxide Compound Treatment Step)

As disclosed in, for example, Japanese Patent Application No. 2001-057145 and Japanese Patent Application No. 2001-057142, earlier filed by the present applicant, the microorganisms used in the present invention produce PHAs containing a unit of the general formula (3) having a sulfanyl group (—S—) as a phenylsulfanyl group or a substituted phenylsulfanyl group on the terminal of the side chain by using such a culture method. The PHAs of the present invention can be produced by selectively oxidizing the sulfur portion of the PHAs thus produced, i.e., a sulfanyl group (—S—). As a specific example, the PHAs of the present invention can be produced by subjecting the PHAs containing a unit of the general formula (3) to oxidation treatment with a peroxide compound.

As for the peroxide compound that can be used in the method for the production of PHAs according to the present invention, any types of peroxide compound may be used as far as it contributes to the object of the present invention, that is, oxidation of the sulfanyl group (—S—) present as a phenylsulfanyl group or substituted phenylsulfanyl group. On this occasion, it is preferred to use in particular a peroxide compound selected from the group consisting of hydrogen peroxide, sodium percarbonate, metachloroperbenzoic acid, performic acid, and peracetic acid when taking into consideration the efficiency of oxidation, influences on the main chain skeleton of PHA, simplicity of treatment and so forth.

First, of those, treatment with hydrogen peroxide, which is easy in its treating method, will be described. The simplest treating method with hydrogen peroxide is a method in which a microorganism is cultured under the above-mentioned culture conditions and the microbial cells having accumulated therein PHA containing the unit of the general formula (3), i.e., a precursor of the PHA of the present invention, are suspended in hydrogen peroxide solution as they are and optionally heated and agitated for a predetermined period of time to treat the cells, and then the target PHA is recovered as an insoluble component. When the concentration of hydrogen peroxide is relatively high or when the reaction temperature is relatively high, the insoluble component derived from the microbial cells, for example, cell membrane may be oxidized to be decomposed and solubilized while only the PHA of the present invention is recovered as insoluble component in a substantially pure form. On the other hand, under mild conditions, the decomposition and solubilization of the insoluble component are not performed sufficiently and the step of disrupting living cells derived from the microbial cells may partly remain.

Upon utilizing such mild conditions, it is possible to apply a method in which cultured microbial cells are disrupted in advance, the insoluble component derived from the microbial cells is removed, PHA containing the unit of the general formula (3), which is a precursor of PHA of the present invention, is recovered as a crude product, then treated with hydrogen peroxide solution. By adopting the method including the step of disrupting cultured microbial cells in advance and separating and recovering the intermediate raw material (precursor) PHA, PHA having sufficiently high purity can be recovered even when the treatment with hydrogen peroxide solution is performed under relatively mild conditions.

In the method of producing the PHA according to the present invention, it is preferred that the step of disrupting living cells as described above is performed by means using no chemicals for disrupting cell membranes, such as a supersonic wave disrupting method, a homogenizer method, a pressure disrupting method, a bead impact method, a triturating method, a grinding method (in which cells are ground in a mortar with addition of an auxiliary agent such as glass powder or alumina powder), and a freezing and thawing method. After the step of disrupting living cells, the separated insoluble component is resuspended and subjected to centrifugation or the like to separate a solid component and a soluble component from each other, and only the solid component, which contains the PHA component serving as an intermediate raw material is treated with hydrogen peroxide.

Further, another method for separating PHA includes a method in which after the culture step only PHA is extracted and isolated from PHA accumulating microbial cells by utilizing a means for extraction and isolation with a solvent in which the accumulated PHA is soluble, such as chloroform, dichloromethane or acetone, and after the extraction and isolation, only the obtained PHA is treated with hydrogen peroxide. In this method of utilizing solvent extraction, the precursor PHA extracted and recovered from microbial cells tends to become agglomerate in an aqueous medium in which treatment with hydrogen peroxide is performed. The agglomerated precursor PHA frequently involves concomitant difficulty and troubles in operation; for example, its contact with a peroxide compound such as hydrogen peroxide is prevented and in some cases the efficiency of the oxidation reaction may be significantly reduced. From this standpoint, the two methods as earlier described are convenient in operation because the precursor PHA originally exists in the form of fine particles in the microbial cell so that in such a state fine particulate precursor PHA can be subjected to the treatment with hydrogen peroxide as a suspension in water.

In the method of producing the PHA according to the present invention, the hydrogen peroxide utilized as an oxidizing agent may be used in any form as far as it can attain the object of the present invention, that is, oxidation of the sulfanyl group (—S—) present as a phenylsulfanyl group or substituted phenylsulfanyl group. From the standpoint of controlling production processes, it is desirable to use a hydrogen peroxide solution whose concentration is in a stable state, for example, hydrogen peroxide dissolved in an aqueous solvent. For example, a hydrogen peroxide solution according to JIS K-8230, which can be produced stably on an industrial scale in large amounts, may be recommended. For example, hydrogen peroxide solution prepared by Mitsubishi Gas Chemical Company, Inc. (containing 31% of hydrogen peroxide) is a preferred solution of hydrogen peroxide in the method of the present invention.

In the method for producing the PHA according to the present invention, the conditions of the oxidation treatment with the hydrogen peroxide may vary depending on the state of PHA to be treated (whether or not microbial cell components are present, whether or not it is agglomerated or in a state of fine particulates, etc.), but it is preferred to select the conditions approximately within the range described below. Generally, when the residual amount of microbial cell components is small, or when the form of the precursor PHA is particulate, oxidation and solubilization of unnecessary microbial cell components are performed readily or the particulate PHA itself is treated more quickly, and thus milder conditions may be used. When utilizing the above-mentioned JIS K-8230 standard preparation hydrogen peroxide solution (containing 31% of hydrogen peroxide), the dilution condition (concentration), use amount, treating temperature, treating time and so forth may be selected within the ranges described below. Concentration of hydrogen peroxide in the treating solution: depending on reaction temperature; from 8% (about 4 fold dilution) to 31% (stock solution), a more preferred concentration range being from 16% (about 2-fold dilution) to 31% (stock solution); Reaction amount: depending on the ratio of the units of the general formula (3) contained in the precursor PHA; from 30 mL to 500 mL in terms of the stock solution of hydrogen peroxide solution (containing 31% of hydrogen peroxide) per 1 g of PHA before the treatment, a more preferred reaction amount being within the range of from 100 mL to 300 mL; Reaction temperature: depending on the concentration of hydrogen peroxide in the treating solution; from 30° C. to 100° C., a more preferred temperature being selected to fall within the range of from 80° C. to 100° C.; and Reaction time: depending on the reaction temperature; from 10 minutes to 180 minutes, a more preferred reaction time being within the range of from 30 minutes to 120 minutes.

Treatment with hydrogen peroxide performed under the conditions within the ranges described above converts the precursor PHA containing the unit of the general formula (3) which is accumulated in the microbial cell into a PHA containing in the polymer molecule thereof at least one of the units of the general formulae (1) and (2), or a PHA that contains in addition to the units of the general formulae (1) and/or (2) the unit of the general formula (3) derived from the intermediate raw material PHA. On this occasion, by selecting the reaction conditions of the treatment with hydrogen peroxide to control a rate at which oxidation proceeds and a reaction amount, the existence ratio of the units of three types described above can be regulated.

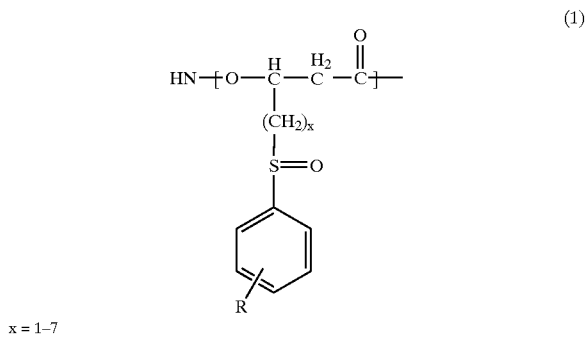

(1)

(wherein R represents H, halogen, CN, $NO_2$, COOR' or $SO_2R''$ (where R' represents H, Na, K, $CH_3$, or $C_2H_5$, and R'' represents OH, ONa, OK, halogen, $OCH_3$, or $OC_2H_5$), and x is an optional integer selected from 1 to 7).

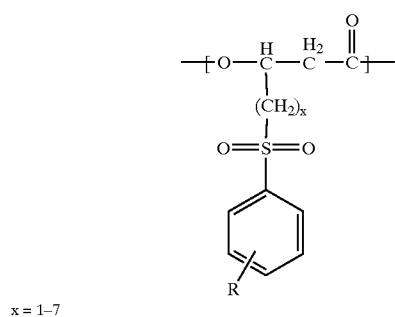

x = 1–7

(wherein R represents H, halogen, CN, $NO_2$, COOR' or $SO_2R"$ (where R' represents H, Na, K, $CH_3$, or $C_2H_5$, and R" represents OH, ONa, OK, halogen, $OCH_3$, or $OC_2H_5$), and x is an optional integer selected from 1 to 7).

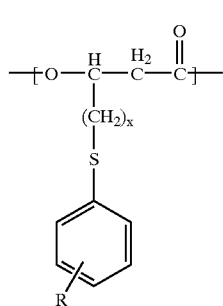

x = 1–7

(wherein R represents H, halogen, CN, $NO_2$, COOR' or $SO_2R"$ (where R' represents H, Na, K, $CH_3$, or $C_2H_5$, and R" represents OH, ONa, OK, halogen, $OCH_3$, or $OC_2H_5$), and x is an optional integer selected from 1 to 7).

Next, the method in which metachloroperbenzoic acid (MCPBA) is used as the peroxide compound will be described.

When MCPBA is used, the oxidation of sulfanyl group (—S—) that exists as a phenylsulfanyl group or substituted phenylsulfanyl group proceeds stoichiometrically, so that it is easy to control the content ratios of the units of the general formulae (1) and (2). Also, since the reaction conditions are mild, unnecessary side reactions such as cleavage of PHA main chain backbone, crosslinking reaction at the active site and the like are prevented from easily occurring. Therefore, in the method for the production of PHA according to the present invention, metachloroperbenzoic acid (MCPBA) is one of very suitable peroxide compounds for selectively producing the target PHA.

As for the general reaction conditions for selectively oxidizing a sulfanyl group (—S—) into a sulfinyl group (—SO—), the reaction is performed in chloroform with the amount of MCPBA being selected to be slightly in excess of 1 mole per mole of the unit containing a sulfanyl group (—S—) in the intermediate raw material PHA (precursor), specifically from the range of from 1.1 to 1.4 moles, at a temperature selected from the range of from 0° C. to 30° C. Under the oxidation conditions as described above, the reaction can proceed up to approximately 90% of the stoichiometric value when the reaction time is so set as to be about 10 hours and up to approximately 100% of stoichiometric value when the reaction time is so set as to be about 20 hours.

To oxidize all the sulfanyl groups (—S—) to sulfonyl groups ($—SO_2—$), the reaction may be performed with the amount of MCPBA being selected to be slightly in excess of 2 moles per mole of the unit containing a sulfanyl group (—S—) in the intermediate raw material PHA (precursor), specifically, in the range of from 2.1 to 2.4 moles, under the same solvent, temperature and time conditions as those described above.

The PHA polymers produced by the method of the present invention by using PHAs produced by microorganisms as intermediate raw materials contain in the polymer molecules thereof a unit having at least one of a sulfinyl structure (—SO—) and a sulfonyl structure ($—SO_2—$). These structures strongly favor the localization of electrons in the molecule at the terminal of the unit so that there is a possibility that the electric properties of the molecule significantly differ from the conventional PHAs. Such localization of electrons may cause the molecule to differ from the conventional PHAs in behavior toward solvent. For example, as described in Examples hereinbelow the molecule becomes soluble even in polar solvents such as dimethylformamide (DMF). In addition, there is a possibility that such properties attributable to the sulfinyl structure (—SO—) or sulfonyl structure ($—SO_2—$), allow the polymer to exhibit a function corresponding to that of an ion exhange resin. Also, since the polymer exhibits such a polarity, it is conceivable that it has increased in affinity with living organisms and hence its application as a biocompatible material is expected. As for the biodegradability of the polymer, the 3-hydroxyalkanoic acid unit contained therein is produced from the PHAs originally produced by microorganisms as an intermediate raw material so that naturally the resulting polymer is of the same optical isomer and retains its biodegradability.

Further, the inventors of the present invention have found that the PHA of the present invention has very excellent properties as a charge control agent and is highly safe for the human body and environment. Furthermore, they have found that when using an electrostatic charge image developing toner containing the charge control agent in an image forming method and in an image forming apparatus having a certain developing system, significant advantages are exhibited, thereby accomplishing the present invention.

That is, the present invention provides a charge control agent containing a polyhydroxyalkanoate having at least one of the monomer units of the general formulae (1) and (2) and optionally having the unit of the general formula (3), and further an electrostatic charge image developing toner containing the charge control agent. Furthermore, the present invention provides an image forming method comprising a charging step of applying a voltage to a charging member from the outside to uniformly charge an electrostatic latent image bearing member, a developing step of forming a toner image on the electrostatic latent image bearing member, a transferring step of transferring the toner image on the electrostatic latent image bearing member to a material to be transferred via or not via an intermediate transferring member, and a heat-fixing step of thermally fixing the toner image on the material to be transferred. The present invention also provides an image forming apparatus comprising the respective means corresponding to the steps of the above-mentioned method, that is, the charging means, the developing means, the transferring means, and the heat-fixing means.

Herein, the compounds described above have a basic skeleton as biodegradable resins and therefore, they can be utilized in production of various products by melt processing or the like in the same manner as conventional plastics, but unlike petroleum-derived synthetic polymers, they have peculiar characteristics that they are decomposed by organisms and incorporated in the material cycle in the natural world when discarded and would not remain in the natural environment. Accordingly, they are also effective from the viewpoint of prevention of air pollution and global warming since they requires no incineration treatment and can be utilized as plastics useful in environmental protection.

The compounds described above, which are suitable as a charge control agent to be used in the electrostatic charge image developing toner, will be described specifically. The compounds used in the present invention are polyester resins that comprise 3-hydroxyalkanoate as a monomer unit and contain at least one of a unit having a phenylsulfinyl structure in the side chain and a unit having a phenylsulfonyl structure in the side chain. Also, the compounds of the present invention may contain, in addition to the two kinds of units a unit having a phenylsulfanyl structure in the side chain. Further, the aromatic moieties of the side chains may be substituted with a functional group optionally selected from the group consisting of H, halogen, CN, $NO_2$, COOR', or $SO_2R''$ (where R' represents H, Na, K, $CH_3$, or $C_2H_5$ and R'' represents OH, ONa, OK, halogen, $OCH_3$, or $OC_2H_5$). Furthermore, the compounds of the present invention may contain, besides these three types of unit, a linear 3-hydroxyalkanoate and a 3-hydroxyalkenoate containing an unsaturated bond in the side chain together or separately.

Here, it should be noted that when such compounds as described above are produced by a method including a step of production by microorganisms, the above-noted compounds of the present invention are polymers that consist only of the R form and are isotactic. However, the compounds of the present invention are not particularly limited to isotactic polymers and atactic polymers can also be utilized as far as the objects of the present invention can be accomplished therewith in both aspects of physical properties and function. Furthermore, the compounds of the present invention can be obtained also by a chemical synthesis method utilizing ring-opening polymerization of lactone compounds.

The polyhydroxyalkanoates used in the charge control agent of the present invention are produced by the methods as described above in detail.

Important factors in the present invention are the unit having a phenylsulfinyl structure in the side chain (the general formula (1)) and the unit having a phenylsulfonyl structure in the side chain (the general formula (2)). These structures cause localization of electrons in the molecule and as a result the charge control agent of the present invention has excellent positive chargeability. The charge control agent of the present invention containing a unit having such a structure contains no ionic functional group unlike the conventional positively chargeable polymeric charge control agents so that it is excellent in weatherability including humidity resistance.

Changing the rate of the unit having a phenylsulfinyl structure in the side chain and the unit having a phenylsulfonyl structure in the side chain or ratios of these units to another unit or other units, the rise of charging may be regulated. Furthermore, regulation of the ratios of the units can reduce the dependence of charging on the environment.

Either one of the unit having a phenylsulfinyl structure in the side chain and the unit having a phenylsulfonyl structure in the side chain may be contained in the polymer in an amount of 1 mol % or more. Such a rate may be selected in consideration of ratios to another unit or other units and desired chargeability. To exhibit sufficient chargeability, it is preferred that either one of them is contained in an amount of 5 mol % or more. The upper limit of the content of the unit having a phenylsulfinyl structure in the side chain or the unit having a phenylsulfonyl structure in the side chain may be determined taking into account a kind of selected binder resin and the relative ratios to another unit or other units within a range in which the compatibility with the binder resin is not deteriorated.

The compounds of the present invention have good compatibility with binder resins; in particular, they have very good compatibility with polyester-based binder resins. The toners containing the compounds of the present invention have a high specific charge quantity and good stability over time, so that the toners can constantly give sharp images upon image formation in electrostatic recording even after storage for a long time. In addition, since the toners are colorless and have positively charging properties, they can be produced both as positively chargeable black toners or as color toners.

Further, by appropriately selecting kinds and ratios of monomer units constituting the compounds of the present invention, the compatibility can be regulated in a wide range. If the resin composition is selected so that the charge control agent can take a micro phase separation structure in the toner binder, no electric continuity is formed in the toner and the toner can stably retain charges. Since the compounds of the present invention contain no heavy metal, there is no polymerization inhibiting action by the heavy metal as observed in the case of metal-containing charge control agents when toners are produced by a suspension polymerization method or an emulsion polymerization method, with the result that toners can be produced stably.

Addition to Toners

In the present invention, the method of incorporating the above-mentioned compounds into toners include an internally adding method and an externally adding method. When they are internally added, it is more desirable that the compounds of the present invention are used in a use amount of usually in the range of from 0.1 to 50 mass %, preferably from 0.3 to 30 mass %, more preferably from 0.5 to 20 mass % in terms of mass ratio of the charge control agent to the toner binder. If the amount is less than 0.1 mass %, undesirably the degree of improvement in the chargeability of toner is not significant. On the other hand, the amount exceeding 50 mass % is not desirable from the economical standpoint. When the compounds of the present invention are externally added, it is preferred that the mass ratio of the charge control agent to the toner binder is 0.01 to 5 mass %. In particular, it is preferred that they are fixed to the surface of the toner mechanochemically. Further, the compounds of the present invention may be used in combination with known charge control agents.

The compounds of the present invention have a number average molecular weight of usually from 1,000 to 500,000, preferably from 1,000 to 300,000. If it is less than 1,000, they are completely compatible with the toner binder so that it is difficult to form discontinuous domains, resulting in insufficient charge and adverse influences on the flowability of the toner. If it exceeds 500,000, they are difficult to disperse in the toner.

The molecular weight of the compounds of the present invention was measured by GPC (gel permeation chromatography). As for the specific method of measuring GPC, the compounds of the present invention were dissolved in advance in 0.1 mass % LiBr-containing dimethylformamide (DMF) and the obtained samples were measured in similar mobile phases, followed by obtaining molecular weight distributions from the standard curve for polystyrene resin.

Furthermore, in the present invention, it is preferred to use the compounds of the present invention that has a ratio (Mw/Mn) of weight average molecular weight (Mw) to number average molecular weight (Mn) in the range of from 1 to 10.

In the present invention, it is preferred that the compounds have a melting point of from 20 to 150° C., in particular from 40 to 150° C., or do not have a melting point but have a glass transition point of from 20 to 150° C., in particular from 40 to 150° C. When the compounds have a melting point of less than 20° C. or do not have a melting point but have a glass transition point of less than 20° C., the flowability of toner or shelf stability tends to be adversely affected. If the compounds have a melting point exceeding 150° C. or do not have a melting point but have a glass transition point exceeding 150° C., the charge control agent is difficult to knead in the toner so that the charge distribution tends to be broad.

In this case, the measurement of a melting point Tm and a glass transition point Tg may be performed by using a high-precision differential scanning calorimeter in internal heat, input compensation type, for example, DSC-7 produced by Perkin-Elmer Corp.

In the toner binder and static charge image developing toner according to the present invention, the mass ratio of the charge control agent to the toner binder is usually from 0.1 to 50 mass %, preferably from 0.3 to 30 mass %, more preferably from 0.5 to 20 mass %. As for the component ratio, the electrostatic charge image developing toner of the present invention contains usually from 0.1 to 50 mass % of the charge control agent, from 20 to 95 mass % of the toner binder, and from 0 to 15 mass % of the coloring material. It may contain 60 mass % or less of magnetic powder (powder of ferromagnetic metal such as iron, cobalt and nickel or compounds such as magnetite, hematite and ferrite) intended to exhibit a function of a coloring material if necessary. Further, the electrostatic charge image developing toner of the present invention may contain various additives (lubricants (polytetrafluoroethylene, low molecular weight polyolefins, fatty acids, or metal salts or amides thereof and so forth) and other charge control agents (nigrosine derivatives, metal naphthenates, alkoxylated amines, quaternary ammonium salts and so forth). Further, hydrophobic colloidal silica fine particles and the like may be used in order to improve the flowability of the toner. The amount of the additives is usually 10 mass % or less based on the mass of the toner.

In the toners of the present invention, it is preferred that at least a portion of the toner binder forms a continuous phase and at least a portion of the charge control agent forms a discontinuous domains. As compared with the toner in which the charge control agent is completely compatible with the toner binder, forming no discontinuous domain therein, the added charge control agent in the present invention tends to be exposed on the surface of the toner, so that addition of a small amount of the charge control agent exhibits a sufficient effect.

The dispersion particle size of the domain is preferably from 0.01 to 4 μm, more preferably 0.05 to 2 μm. If it exceeds 4 μm, the dispersibility is insufficient so that the charge distribution is widened and a problem of decreased transparency of the toner arises. If the dispersion particle size is less than 0.01 μm, the situation is substantially the same as the case where the charge control agent is completely compatible with the toner binder, forming no discontinuous domain therein and in this case, the charge control agent is required to be added in a large amount.

The fact that at least a portion of the charge control agent forms discontinuous domains and the dimension of the dispersion particle size can be confirmed by observing a section of the toner with a transmission electron microscope. To clearly observe the interface, it is also effective to make an electron microscopic observation after staining the toner section with ruthenium tetroxide, or osmium tetroxide.

In order to reduce the particle size of the discontinuous domains formed by the compounds of the present invention, polymers compatible with the toner binder as well as with the compounds of the present invention may be added as a compatibilizing agent. The compatibilizing agent includes polymers that comprises a polymer chain containing 50 mol % or more of a monomer having substantially the same structure as the monomer unit in the compound of the present invention and a polymer chain containing 50 mol % or more of a monomer having substantially the same structure as the monomer in the toner binder, with the polymer chains being connected in a graft- or block-form, and the like. The amount of the compatibilizing agent is usually 30 mass % or less, preferably 1 to 10 mass % based on the mass of the compound of the present invention.

Other Constituent Materials

Hereinafter, other constituent materials contained in the electrostatic charge image developing toner of the present invention will be described.

Binder Resin

First, the binder resin that can be used in the present invention is not particularly limited and any binder resin that is usually used in producing toners may be employed. The charge control agent of the present invention may be mixed with a binder resin in advance before preparing a toner and the mixture may be used as a toner binder composition having a charge control capacity. Examples of the binder resin include styrene-based polymers, polyester-based polymers, epoxy-based polymers, polyolefin-based polymers, polyurethane-based polymers and the like. These may be used singly or as mixtures.

Examples of the styrene-based polymer include copolymers of styrene and (meth)acrylic acid ester, copolymers of these monomers and other monomer copolymerizable therewith, copolymers of styrene and a diene-based monomer (butadiene, isoprene or the like) and copolymers of these monomers and other monomers copolymerizable therewith, and the like. The polyester-based polymer includes polycondensation products between an aromatic dicarboxylic acid and an alkylene oxide adduct of an aromatic diol and the like. The epoxy-based polymer includes reaction products between an aromatic diol and epichlorohydrin and modified products thereof and the like. The polyolefin-based polymer includes polyethylene, polypropylene and copolymer chains of these and other monomers copolymerizable therewith, and the like. The polyurethane-based polymer includes polyaddition products between an aromatic diisocyanate and an alkylene oxide adduct of an aromatic diol and the like.

In the present invention, specific examples of the binder resin used include polymers of polymerizable monomers described below, mixtures of these or copolymerization products obtained by using two or more polymerizable monomers described below. Specifically, such polymers include, for example, styrene-based polymers such as styrene/acrylic acid copolymers, or styrene/methacrylic acid-based copolymers, polyester-based polymers, epoxy-based polymers, polyolefin-based polymers, polyurethane-based polymers and the like, which are suitably used.

Specific examples of the polymerizable monomer includes styrene and derivatives of styrene, for example, styrene; styrene derivatives, such as o-methylstyrene, m-methylstyrene, p-methylstyrene, p-methoxystyrene, p-phenylstyrene, p-chlorostyrene, 3,4-dichlorostyrene, p-ethylstyrene, 2,4-dimethylstyrene, p-n-butylstyrene, p-tert-butylstyrene, p-n-hexylstyrene, p-n-octylstyrene p-n-nonylstyrene, p-n-decylstyrene, and p-n-dodecylstyrene; ethylenically unsaturated monoolefins, such as ethylene, propylene, butylene, and isobutylene; unsaturated polyenes, such as butadiene; vinyl halides, such as vinyl chloride, vinylidene chloride, vinyl bromide, and vinyl fluoride; vinyl esters, such as vinyl acetate, vinyl propionate, and vinyl benzoate; α-methylene-aliphatic monocarboxylic acid esters, such as methyl methacrylate, ethyl methacrylate, propyl methacrylate, methacrylate, n-butyl methacrylate, isobutyl methacrylate, n-octyl methacrylate, dodecyl methacrylate, 2-ethylhexyl methacrylate, stearyl methacrylate, phenyl methacrylate, dimethylaminoethyl methacrylate, and diethylaminoethyl methacrylate; acrylic acid esters, such as methyl acrylate, ethyl acrylate, n-butyl acrylate, isobutyl acrylate, propyl acrylate, n-octyl acrylate, dodecyl acrylate, 2-ethylhexyl acrylate, stearyl acrylate, 2-chloroethyl acrylate, and phenyl acrylate; vinyl ethers, such as vinyl methyl ether, vinyl ethyl ether, and vinyl isobutyl ether; vinyl ketones, such as vinyl methyl ketone, vinyl hexyl ketone, and methyl isopropenyl ketone; N-vinyl compounds, such as N-vinylpyrrole, N-vinylcarbazole, N-vinylindole, and N-vinylpyrrolidone; vinylnaphthalenes; acrylic acid or methacrylic acid derivatives, such as acrylonitrile, methacrylonitrile, and acrylamide; dicarboxylic acids, such as maleic acid, phthalic acid, succinic acid, terephthalic acid; esters of the above-mentioned α,β-unsaturated esters and diesters of dibasic acids such as methyl maleate, butyl maleate, and dimethyl maleate; polyol compounds, such as ethylene glycol, diethylene glycol, triethylene glycol, 1,2-propylene glycol, 1,3-propylene glycol, 1,4-butanediol, 1,6-hexanediol, bisphenol A, hydrogenated bisphenol A, and polyoxyethylenated bisphenol A; isocyanates, such as p-phenylene diisocyanate, p-xylylene diisocyanate, and 1,4-tetramethylene diisocyanate; amines, such as ethylamine, butylamine, ethylenediamine, 1,4-diaminobenzene, 1,4-diaminobutane, and monoethanolamine; epoxy compounds, such as diglycidyl ether, ethylene glycol diglycidyl ether, bisphenol A glycidyl ether, and hydroquinone diglycidyl ether; and so forth.

Crosslinking Agent

In preparing a binder resin used in the present invention, crosslinking agents described below may be used as necessary. Examples of the bifunctional crosslinking agent include divinylbenzene, bis(4-acryloxypolyethoxyphenyl) propane, ethylene glycol diacrylate, 1,3-butylene glycol diacrylate, 1,4-butanediol diacrylate, 1,5-pentanediol diacrylate, 1,6-hexanediol diacrylate, neopentyl glycol diacrylate, diethylene glycol diacrylate, triethylene glycol diacrylate, tetraethylene glycol diacrylate, polyethylene glycol #200 diacrylate, polyethylene glycol #400 diacrylate, polyethylene glycol #600 diacrylate, dipropylene glycol diacrylate, polypropylene glycol diacrylate, polyester type diacrylates (MANDA, trade name; available from Nippon Kayaku Co., Ltd.), and the above diacrylates whose acrylate moiety has been replaced with dimethacrylate.

More than bifunctional, that is, polyfunctional crosslinking agents may include pentaerythritol triacrylate, trimethylolethane triacrylate, trimethylolpropane triacrylate, tetramethylolmethane tetraacrylate, oligoester acrylate, and the above compounds whose acrylate moiety has been replaced with methacrylate, and also 2,2-bis(4-methacryloxypolyethoxyphenyl)propane, diallyl phthalate, triallyl cyanurate, triallyl azo cyanurate, triallyl isocyanurate and triallyl trimellitate, diaryl chlorendate.

Polymerization Initiator

In preparing a binder resin used in the present invention, polymerization initiators described below may be used as necessary. The polymerization initiator includes, for example, t-butyl peroxy-2-ethylhexanoate, cumene perpivalate, t-butyl peroxylaurate, benzoyl peroxide, lauroyl peroxide, ocatanoyl peroxide, di-t-butyl peroxide, t-butylcumyl peroxide, dicumyl peroxide, 2,2'-azobisisobutyronitrile, 2,2'-azobis(2-methylbutyronitrile), 2,2'-azobis(2,4-dimethylvaleronitrile),2,2'-azobis(4-methoxy-2,4-dimethylvaleronitrile), 1,1-bis(t-butylperoxy)-3,3,5-trimethylcyclohexane, 1,1-bis(t-butylperoxy)cyclohexane, 1,4-bis(t-butylperoxycarbonyl)cyclohexane, 2,2-bis(t-butylperoxy)octane, n-butyl-4,4-bis(t-butylperoxy)valerate, 2,2-bis(t-butylperoxy)butane, 1,3-bis(t-butylperoxyisopropyl)benzene, 2,5-dimethyl-2,5-di(t-butylperoxy)hexane, 2,5-dimethyl-2,5-di(t-butylperoxy)hexane,2,5-dimethyl-2,5-di(benzoylperoxy)hexane, di-t-butyl diperoxyisophthalate, 2,2-bis(4,4-di-t-butylperoxycyclohexyl)propane, di-t-butyl peroxy-α-methylsuccinate, di-t-butyl peroxydimethylglutarate, di-t-butyl peroxyhexahydroterephthalate, di-t-butyl peroxyazelate, 2,5-dimethyl-2,5-di(t-butylperoxy)hexane, diethylene glycol bis(t-butylperoxycarbonate), di-t-butyl peoxytrimethyladipate, tris(t-butylperoxy)triazine, vinyl tris (t-butylperoxy)silane and the like. These may be used singly or in combination. As for the amount thereof, they may be used in a concentration of 0.05 mass parts or more, preferably from 0.1 to 15 mass parts per 100 mass parts of the monomer.

Other Biodegradable Plastics

Further, in the present invention, biodegradable plastics may be preferably used. The biodegradable plastic may include "Ecostar" and "Ecostar Plus" (tradenames, Hagiwara Kogyo Co., Ltd.), "Biopol" (tradename, ICI Japan, Co., Ltd.), "Ajicoat" (tradename, Ajinomoto Co., Inc.), "Placcel" and "Polycaprolactone" (tradenames, Daicel Chemical Industries, Ltd.), "Sholex" and "Bionolle" (tradenames, Showa Denko K.K.), "Lacty" (tradename, Shimadzu Corporation), "LACEA" (tradename, Mitsui Chemical Inc.), "Yupek" (tradename, Mitsubishi Gas Chemical Company, Inc.) and the like.

It is preferred that the binder resin and the charge control agent of the present invention are combined so that the polymer structure of the binder resin and that of the polymer chain of the charge control agent are as close as possible to each other. If the polymer structure of the binder resin and that of the polymer chain of the charge control agent differ from each other to a considerable extent, dispersion of the charge control agent into the binder resin tends to be insufficient.

The charge control agent of the present invention is internally added to the resin binder in a mass ratio of usually from 0.1 to 50 mass %, preferably from 0.3 to 30 mass %, more preferably from 0.5 to 20 mass % based on the binder resin. If the mass ratio of the internally added charge control agent is less than 0.1 mass %, the charge quantity of the toner is small, while if it exceeds 50 mass %, the charging stability of the toner is deteriorated.

Colorant

As for the colorant that constitutes the electrostatic charge image developing toner of the present invention, any colorant that is generally used in producing toners may be used and is not particularly limited. For example, carbon black, titanium white, any other pigments and/or dyes may be used.

For example, when the electrostatic charge image developing toner of the present invention is used as a magnetic color toner, the colorant that can be used includes, for example, C.I. Direct Red 1, C.I. Direct Red. 4, C.I. Acid Red 1, C.I. Basic Red 1, C.I. Mordant Red 30, C.I. Direct Blue 1, C.I. Direct Blue 2, C.I. Acid Blue 9, C.I. Acid Blue 15, C.I. Basic Blue 3, C.I. Basic Blue 5, C.I. Mordant Blue 7, C.I. Direct Green 6, C.I. Basic Green 4, C.I. Basic Green 6, etc.

As the pigment, there may be used chrome yellow, cadmium yellow, mineral fast yellow, navel yellow, naphthol yellow S, Hansa yellow G, permanent yellow NCG, tartrazine lake, chrome orange, molybdenum orange, permanent orange GTR, pyrazolone orange, benzidine orange G, cadmium red, permanent red 4R, watching red calcium salt, eosin lake, brilliant carmine 3B, manganese violet, fast violet B, methyl violet lake, Prussian blue (iron blue), cobalt blue, alkali blue lake, victoria blue lake, phthalocyanine blue, fast sky blue, indanthrene blue BC, chrome green, chromium oxide, pigment green B, malachite green lake, final yellow green G and the like.

Further, when the electrostatic charge image developing toner of the present invention is used as a toner for two-component full color toner, the following may be used as a colorant. Examples of the coloring pigment for magenta color toner include C.I. Pigment Red 1, 2, 3, 4, 5, 6, 7, 8, 9, 10, 11, 12, 13, 14, 15, 16, 17, 18, 19, 21, 22, 23, 30, 31, 32, 37, 38, 39, 40, 41, 48, 49, 50, 51, 52, 53, 54, 55, 57, 58, 60, 63, 64, 68, 81, 83, 87, 88, 89, 90, 112, 114, 122, 123, 163, 202, 206, 207, and 209, C.I. Pigment Violet 19, C.I. Vat Red 1, 2, 10, 13, 15, 23, 29, and 35, etc.

In the present invention, the above-cited pigments may be used singly. However, it is more preferred that a dye and a pigment are used in combination to increase sharpness of the pigment in consideration of the image quality of full color images. Examples of the dye for magenta used in this case include oil-soluble dyes, such as C.I. Solvent Red 1, 3, 8, 23, 24, 25, 27, 30, 49, 81, 82, 83, 84, 100, 109, and 121, C.I. Disperse Red 9, C.I. Solvent Violet 8, 13, 14, 21, and 27, C.I. Disperse Violet 1, etc.; basic dyes, such as C.I. Basic Red 1, 2, 9, 12, 13, 14, 15, 17, 18, 22, 23, 24, 27, 29, 32, 34, 35, 36, 37, 38, 39, 40, C.I. Basic Violet 1, 3, 7, 10, 14, 15, 21, 25, 26, 27, and 28; etc.

Other coloring pigments include cyan coloring pigments, such as C.I. Pigment Blue 2, 3, 15, 16, and 17, C.I. Vat Blue 6, C.I. Acid Blue 45 and copper phthalocyanine pigments having a phthalocyanine skeleton substituted with 1 to 5 phthalimidomethyl groups, etc.

Examples of the coloring pigment for yellow include C.I. Pigment Yellow 1, 2, 3, 4, 5, 6, 7, 10, 11, 12, 13, 14, 15, 16, 17, 23, 65, 73, and 83, C.I. Vat Yellow 1, 3, and 20, etc.

The dyes and pigments as described above may be used singly or as optional mixtures in order to obtain a desired color tone of the toner. Taking into consideration environmental protection or safety for the human body, various kinds of edible coloring matter may be suitably used. The content of the above-mentioned colorants in the toner may be varied widely depending on a desired coloring effect or other factors. Usually, to obtain the best toner characteristics, that is, taking into consideration coloring power of printing, shape stability of toner, flying of toner and so forth, the colorants are used in a proportion of usually from 0.1 to 60 mass parts, preferably from 0.5 to 20 mass parts per 100 mass parts of the binder resin.

Other Components of Toner

The electrostatic charge image developing toner of the present invention may contain, besides the above-mentioned binder resin and colorant components, the compounds described below within the range in which they do not give adverse influence on the effects of the present invention (in a proportion smaller than the contents of the binder resin component). Examples of such compounds include aliphatic or alicyclic hydrocarbon resins and aromatic petroleum resins, such as silicone resin, polyester, polyurethane, polyamide, epoxy resin, polyvinyl butyral, rosin, modified rosin, terpene resin, phenol resin, low molecular weight polyethylene, and low molecular weight polyproplene, and chlorinated paraffin, paraffin wax, and so forth. Preferably usable waxes among these specifically include low molecular weight polypropylene and side products thereof, low molecular weight polyesters and ester-based waxes, aliphatic derivatives thereof. Also, waxes prepared by fractionation of these waxes according to molecular weight by various methods may be preferably used in the present invention. Further, after the fractionation, oxidation, block copolymerization or graft modification may be performed.

In particular, the electrostatic charge image developing toner of the present invention exhibits excellent characteristics in the case where laminagraphic observation performed with a transmission electron microscope (TEM) shows that the wax component is dispersed in the binder resin in the form of substantially spherical and/or spindle-shaped islets Toner Production Process As a specific method for producing the electrostatic charge image developing toner of the present invention having the above constitution, any one of known methods may be used. The electrostatic charge image developing toner of the present invention can be produced by the so-called pulverization method in which a toner is obtained, for example, by the following processes.

That is, stated specifically, the electrostatic charge image developing toner of the present invention can be obtained as follows: The above-explained compound of the present invention, resins such as a binder resin, and a wax that is added as needed are sufficiently mixed in a mixer such as a Henschel mixer, a ball mill or the like and melt-kneaded by using a thermal kneader such as a heat roll, a kneader or an extruder to make the resins compatible with each other. Then, a pigment, dye or magnetic material as a colorant, and an additive that is added as needed, such as a metal compound, are dispersed or dissolved in the kneaded resin and cooled and solidified. The solid is then pulverized by a pulverizer such as a jet mill or a ball mill and classified to produce the electrostatic charge image developing toner of the present invention having a desired particle size. In the classification step, it is preferred to use a multisegment classifier to increase the production efficiency.

The electrostatic charge image developing toner of the present invention can be obtained also by the following method. That is, a binder resin and the compound of the present invention are mixed in the form of solutions by using a solvent or solvents (aromatic hydrocarbons such as toluene and xylene, halides such as chloroform and ethylene dichloride, ketones such as acetone and methyl ethyl ketone, amides such as dimethylformamide, and the like) and agitated. Thereafter, the mixed solution is poured into water to cause reprecipitation, and the solids are filtered, dried and pulverized by using a pulverizer such as a jet mill or a ball mill, followed by classification to obtain the electrostatic charge image developing toner of the present invention having a desired particle size. In the classification step, it is preferred to use a multisegment classifier to increase the production efficiency.

Further, the electrostatic charge image developing toner of the present invention can be obtained also by a so-called polymerization method as described below. In this case, the compound of the present invention and materials such as a polymerizable monomer, a pigment, dye or magnetic material as a colorant and optionally a crosslinking agent, a polymerization initiator, a wax, and other additives are mixed and dispersed and subjected to suspension polymerization in an aqueous dispersion medium in the presence of a surfactant and the like to synthesize polymerizable colored resin particles. Then, the obtained particles are subjected to solid-liquid separation, dried and classified as necessary to obtain the electrostatic charge image developing toner of the present invention.

Furthermore, colored fine particles containing no charge control agent can be prepared by the methods described above and then, the compound of the present invention, singly or together with an external additive such as colloidal silica, may be added and fixed to the surface of the particles by a mechanochemical method or the like.

Silica External Additive

In the present invention, it is preferred that silica fine powder is added externally to the toner prepared by the above-mentioned method in order to increase charge stability, developability, flowability and durability. On this occasion, use of silica fine powder that has a specific surface area in the range of 20 m$^2$/g or more, in particular 30 to 400 m$^2$/g, as measured by nitrogen absorption according to the BET method can give good results. In this case, it is preferred to use the silica fine powder in an amount of from about 0.01 to about 8 mass parts, preferably from about 0.1 to about 5 mass parts, per 100 mass parts of the toner particle. As for the silica fine powder to be used, it is preferred to use one that is treated with a treating agent such as silicone varnish, various kinds of modified silicone varnish, silicone oil, various kinds of modified silicone oil, silane coupling agents, silane coupling agents having a functional groups, and other organosilicon compounds as needed for the purpose of imparting to the toner hydrophobic nature or controlling the chargeability of the toner. These treating agents may be used as mixtures.

Inorganic Powder

To increase the developability and durability of the toner, it is preferred to add inorganic powders, for example, powders of oxides of metals such as magnesium, zinc, aluminum, cerium, cobalt, iron, zirconium, chromium, manganese, strontium, tin, and antimony; composite metal oxides such as calcium titanate, magnesium titanate, and strontium titanate; metal salts such as calcium carbonate, magnesium carbonate and aluminum carbonate; clay minerals such as kaolin; phosphate compounds such as apatite; silicon compounds such as silicon carbide and silicon nitride; and carbon powders such as carbon black and graphite. Among those, fine powders of zinc oxide, aluminum oxide, cobalt oxide, manganese dioxide, strontium titanate, and magnesium titanate are preferably used.

Lubricant

Further, lubricant powder as described below may be added to the toner. Examples of the lubricant powder includes fluororesins such as Teflon, polyvinylidene fluoride; fluoro compounds such as carbon fluoride; fatty acid metal salts such as zinc stearate; fatty acid, fatty acid derivatives such as fatty acid esters; molybdenum sulfide and the like.

Carrier

The electrostatic charge image developing toner of the present invention having the above-described structure and properties may be applied to various kinds of known toners; for example, it may be used as a nonmagnetic toner that is used singly as a nonmagnetic one-component developer or as a magnetic two-component developer together with a magnetic carrier, or as a magnetic toner used singly as a magnetic one-component developer. Any conventionally known carrier may be used as a carrier in the two-component developing method. Specifically, surface-oxidized or -nonoxidized particles having an average particle size of from 20 to 300 μm formed from metals such as iron, nickel, cobalt, manganese, chromium, and rare earth elements, alloys thereof or oxides may be used as carrier particles. It is preferred that the carrier used in the present invention comprise the carrier particles described above, the surface of which are coated with a substance such as a styrene-based resin, acrylic-based resin, a silicone-based resin, a fluoro-based resin, a polyester resin or the like or has such a substance adhered thereto.

Magnetic Toner

The electrostatic charge image developing toner of the present invention may contain a magnetic material in the toner particles to form a magnetic toner. In this case, the magnetic material may also serve as a colorant. The magnetic material that can be used on this occasion includes iron oxides such as magnetite, hematite and ferrite; and metals such as iron, cobalt and nickel or alloys and mixtures of these metals with other metals such as aluminum, cobalt, copper, lead, magnesium, tin, zinc, antimony beryllium, bismuth, cadmium, calcium, manganese, selenium, titanium, tungsten, and vanadium. Preferably, the magnetic materials that can be used in the present invention have an average particle size of 2 μm or less, more preferably from about 0.1 to about 0.5 μm. It is preferred that they are contained in the toner in an amount of from 20 to 200 mass parts per 100 mass parts of the binder resin, particularly preferably from 40 to 150 mass parts per 100 mass parts of the binder resin.

Further, to accomplish high image quality, it is necessary to make it possible to faithfully develop finer latent image dots. For this purpose, for example, it is preferable to control the electrostatic charge image developing toner particles of the present invention so as to have a weight average particle size in the range of from 4 to 9 μm. That is, the toner particles having a weight average particle size less than 4 μm are undesirable, since with such a toner the image transfer efficiency tends to decrease and much untransferred toner is liable to remain on the photosensitive member after the transfer, which tends to cause unevenness of image due to fogging/transfer failure. If the weight average particle size of the toner particle exceeds 9 μm, scattering of characters or line images tends to occur.

In the present invention, the average particle size and particle size distribution of the toner are determined by using Coulter Counter TA-II (available from Coulter Electronics, Inc.) or Coulter Multisizer (available from Coulter Electronics Inc.), connected to an interface (Nikkaki Co., Ltd.) for outputting number distribution and volume distribution, and a personal computer PC 9801 (available from NEC K.K.). As the electrolyte to be used in the measurement is a 1% NaCl aqueous solution prepared with first class grade sodium chloride. The 1% NaCl aqueous solution is also commercially available; for example, ISOTON R-II (produced by Coulter Scientific Japan Co.). Specifically, for measurement, 0.1 to 5 mL of a surfactant (preferably an alkylbenzenesulfonic acid salt) as a dispersant and further 2 to 20 mg of a measurement sample are added to 100 to 150 mL of the electrolytic solution to form a sample for measurement. In the measurement, the resultant suspension of the measurement sample in the electrolytic solution is subjected to a dispersion treatment by an ultrasonic disperser for about 1 to 3 minutes and then subjected to measurement of particle size distribution by using the above-mentioned Coulter Counter TA-II equipped with a 100 $\mu$m-aperture as an aperture to obtain the volume and number of toner particles equal to or greater than 2 $\mu$m. From these a volume-basis particle size distribution and a number-basis particle size distribution were calculated. Then, the volume-basis weight average particle size (D4) and number-basis length-average particle size (D1) related to the present invention are derived from the volume-basis and number-basis distributions, respectively.

Charge Amount

It is preferred that the electrostatic charge image developing toner of the present invention has a charge quantity (two component method) per unit mass of +10 to +80 $\mu$C/g, more preferably +15 to +70 $\mu$C/g in order to increase transfer efficiency in a transfer method using a voltage applied transfer member.

Figure 13:
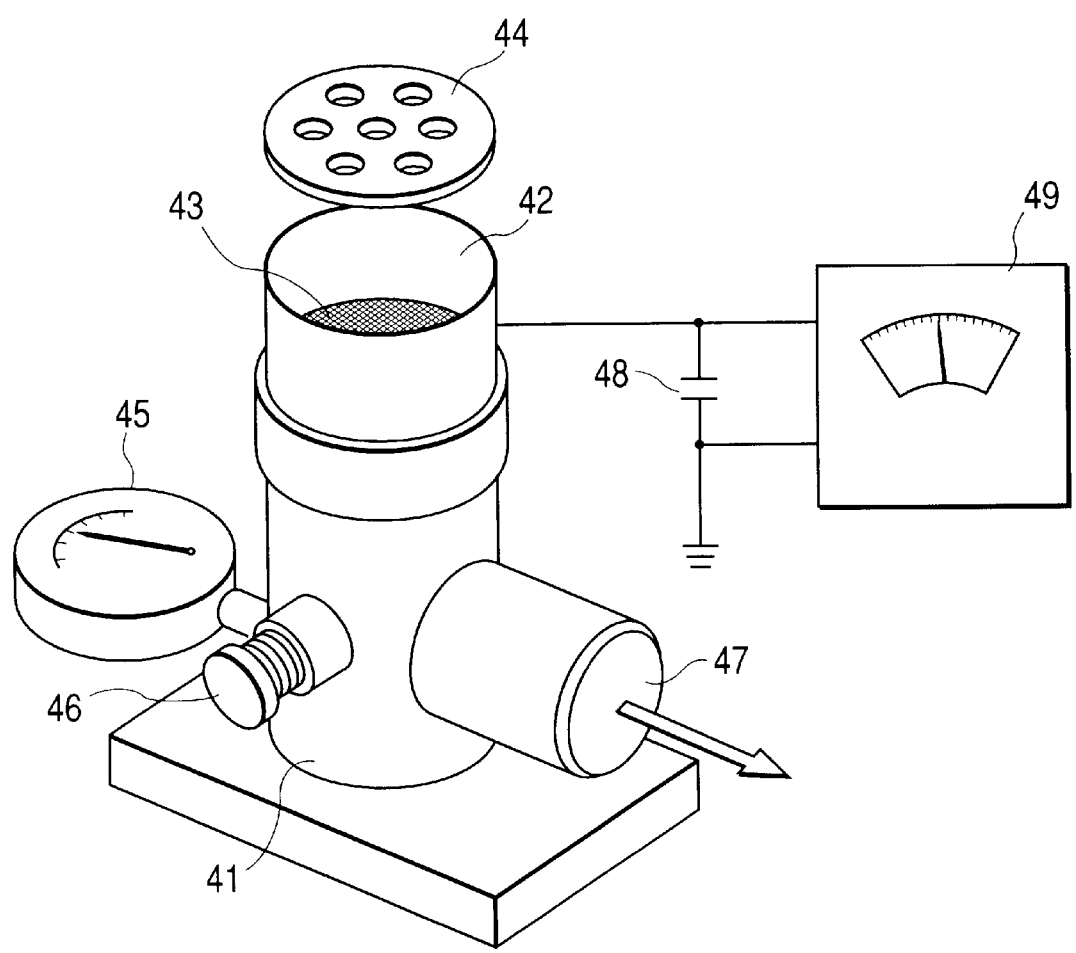
FIG. 13 is a schematic diagram showing a blow-off charging amount measuring apparatus that measures the charging amount of a toner.

The method for measuring a charge quantity (two component triboelectric charge amount) by a two component method used in the present invention is as indicated below. For measurement, a charge amount measuring apparatus as shown in FIG. 13 is used. First, under a certain environment, a mixture of 9.5 g of EFV 200/300 (tradename, produced by Powdertech Co., Ltd.) as a carrier and 0.5 g of toner to be measured is added into a 50 to 100 mL capacity polyethylene bottle, which is then placed in a shaker set under shaking conditions of a fixed shaking width of 100 mm and a shaking speed of 100 strokes per minute and shaken for a predetermined period of time. Then, 1.0 to 1.2 g of the shaken mixture is charged in a measurement container 42 (made of metal) provided with a 500-mesh screen 43 at the bottom which is equipped in the charge amount measuring apparatus shown in FIG. 13 and covered with a metal lid 44. The total mass of the measurement container 42 is weighed and denoted by W1 (g). Then, an aspirator (not shown), in which at least the part contacting with the measurement container 42 is composed of an insulator, is operated to effect suction through a suction port 47 while pressure is so regulated as to be 2450 Pa (250 mmAq) with a vacuum gauge 45 by adjusting an airflow control valve 46. In this state, suction is continued for 1 minute to remove the toner. The reading at this time of a potential meter 49 is denoted by V (volts). Here, 48 designates a capacitor having a capacitance C ($\mu$F). The total mass of the measuring apparatus after the suction is measured and denoted by W2 (g). Then, the triboelectric charge amount ($\mu$C/g) of the toner is calculated by the following equation:

Triboelectric charge amount ($\mu$C/g)=C×V/(W1−W2).

Molecular Weight Distribution of Binder Resin

It is preferred that the binder resin used as a constituent material of the electrostatic charge image developing toner of the present invention shows a low molecular weight region peak in the range from 3,000 to 15,000 in the molecular weight distribution by gel permeation chromatography (GPC), in particular, when it is prepared by a pulverization method. That is, if the GPC peak in the low molecular weight region exceeds 15,000, improvement in transfer efficiency may in some cases become insufficient. On the other hand, the use of a binder resin having a GPC peak in the low molecular weight region of less than 3,000 is not desirable since fusion tends to occur at the time of surface treatment.

In the present invention, the molecular weight of the binder resin is measured by gel permeation chromatography (GPC). A specific method for the measurement by GPC may include the following method: the toner is beforehand extracted with THF (tetrahydrofuran) solvent for 20 hours by means of a Soxhlet extractor, and the sample thus obtained is used for measurement of molecular weight by using columns of Shodex A-801, 802, 803, 804, 805, 806 and 807, (trade names, made by Showa Denko K.K.) connected in series, and using a calibration curve of reference polystyrene resin. In the present invention, it is preferred to use a binder resin having a ratio (Mw/Mn), which is a ratio of the weight average molecular weight (Mw) and number average molecular weight (Mn) thus measured, in the range of from 2 to 100.

Glass Transition Point of Toner

It is preferred that the toner of the present invention is so prepared as to have a glass transition point Tg of 40 to 75° C., more preferably 52 to 70° C., by using appropriate materials in consideration of fixing property and shelf life. In this case, the glass transition point Tg of the toner is measured using a high-precision differential scanning calorimeter in internal heat, input compensation type, for example, DSC-7, manufactured by Perkin Elmer Co., according to ASTM D3418-82. In the present invention, when measuring the glass transition point Tg, the temperature of a sample to be measured is once elevated to record all the thermal hysteresis and then quickly cooled. Again, the temperature of the sample is elevated at a temperature rise rate of 10° C./minute within the temperature range of 0 to 200° C. A DSC curve obtained based on the results of measurements under these conditions may be suitably used.

Image Forming Method

The electrostatic charge image developing toner of the present invention described above is particularly preferably applied to an image forming method comprising at least a charging step of charging an electrostatic latent image bearing member by applying a voltage to a charging member from the outside, a step of forming an electrostatic charge image on the charged electrostatic latent image bearing member, a developing step of developing the electrostatic charge image by using a toner to form a toner image on the electrostatic latent image bearing member, a transfer step of transferring the toner image on the electrostatic latent image bearing member to a recording medium, and a heat-fixing step of thermally fixing the toner image on the recording medium thereto. Alternatively, the toner of the present invention may be particularly preferably applied to the above-described method in which the transfer step comprises a first transfer step of transferring the toner image on the electrostatic latent image bearing member to an intermediate transfer member and a second transfer step of transferring the toner image on the intermediate transfer member to the recording medium.

EXAMPLES

Hereinafter, the present invention will be illustrated in more detail by referring to examples. Although these examples are each one example of the best mode for carrying out the present invention, the present invention should not be construed as being limited thereto.

First, Examples 1 to 9 below show production examples for the production of PHAs containing at least one of a 3-hydroxy-5-(phenylsulfinyl)valerate unit and a 3-hydroxy-5-(phenylsulfonyl)valerate unit in the polymer molecule, or PHAs containing a 3-hydroxy-5-(phenylsulfanyl)valerate unit in addition to the above-mentioned two kinds of units, by cultivating a PHA producing microorganism in a medium containing 5-(phenylsulfanyl)valeric acid as a raw material to produce a desired PHA and then subjecting the PHA produced by the PHA producing microorganism to oxidation treatment with a peroxide compound.

Example 1

In a 500 mL shake flask, 200 mL of M9 medium containing 0.5% of commercially available polypeptone (available from Wako Pure Chemical Industries, Ltd.) and 0.1% of 5-(phenylsulfanyl)valeric acid were placed and a colony of strain YN2 obtained by culturing seed cells selected on an agar plate was inoculated and cultured at 30° C. for 24 hours. After the culture, the microbial cells were harvested by centrifugation. To remove the residual medium components, the harvested microbial cells were suspended in 40 mL of deionized water and again centrifuged to recover the washed microbial cells.

The recovered microbial cells were resuspended in 50 mL of commercially available hydrogen peroxide solution (containing 31% hydrogen peroxide, produced by Mitsubishi Gas Chemical Company, Inc., a standard preparation according to JIS K-8230). The microbial cell suspension was transferred to a 200 mL eggplant-shaped flask, which was placed on an oil bath at 100° C. for 1 hour for reaction. After completion of the reaction, the reaction mixture was cooled down to room temperature and solid component PHA was separated by centrifugation. The separated PHA was resuspended in distilled water and again centrifuged to wash off the residual hydrogen peroxide solution. Further, this washing operation was repeated twice. Thereafter, the washed PHA polymer was dried under reduced pressure and the dry weight (recovered amount) was weighed.

The average molecular weight of the obtained PHA sample was measured by gel permeation chromatography (GPC). The conditions of GPC were as follows:

Apparatus: Tosoh, HLC-8020;

Column: Polymer Laboratory, PLgel, MIXED-C (5 μm)× 2;

Mobile Phase Solvent: 0.1 mass % LiBr containing DMF; molecular weight converted on the polystyrene basis.

Further, the structure of PHA contained in the sample was analyzed by proton-nuclear magnetic resonance apparatus ($^1$H-NMR) under the following conditions:

Apparatus: Bruker DPX400 FT-NMR;

$^1$H Resonance frequency: 400 MHz;

Nuclide to be analyzed: $^1$H;

Solvent used: $CDCl_3$;

Reference: $TMS/CDCl_3$ sealed in a capillary;

Temperature for measurement: room temperature.

Example 2

Cultured cells of strain YN2 obtained by the same culture method as in Example 1 were washed with water in the same manner as in Example 1 to recover the microbial cells. The washed cells were suspended in 25 mL of deionized water and 25 mL of hydrogen peroxide solution of the same specification as used in Example 1 was added to the cell suspension. The mixture was transferred to a 200 mL capacity eggplant-shaped flask, which was placed on an oil bath at 100° C. 1 hour for reaction. After completion of the reaction, the reaction mixture was cooled down to room temperature and the solid component PHA was separated by centrifugation. The separated PHA was resuspended in distilled water and again centrifuged to wash off the residual hydrogen peroxide solution. Further, this washing operation was repeated twice. Thereafter, the washed PHA polymer was dried under reduced pressure and the dry weight (recovered amount) was weighed. The average molecular weight and structure of the PHA sample obtained under the conditions of this treatment with hydrogen peroxide solution were analyzed by GPC and $^1$H-NMR, respectively, under the conditions described in Example 1.

Example 3

Cultured cells of strain YN2 obtained by the same culture method as in Example 1 were washed with water in the same manner as in Example 1 to recover the microbial cells. The washed microbial cells were suspended in 30 mL of deionized water and 10 mL of hydrogen peroxide solution of the same specification as used in Example 1 was added to the microbial cell suspension. The mixture was transferred to a 200 mL capacity eggplant-shaped flask, which was placed on an oil bath at 100° C. for 1 hour for reaction. After completion of the reaction, the reaction mixture was cooled down to room temperature and the solid component PHA was separated by centrifugation. The separated PHA was resuspended in distilled water and again centrifuged to wash off the residual hydrogen peroxide solution. Further, this washing operation was repeated twice. Thereafter, the washed PHA polymer was dried under reduced pressure and the dry weight (recovered amount) was weighed. The average molecular weight and structure of the PHA sample obtained under the conditions of this treatment with hydrogen peroxide solution were analyzed by GPC and $^1$H-NMR, respectively, under the conditions described in Example 1.

Example 4

Cultured cells of strain YN2 obtained by the same culture method as in Example 1 were washed with water in the same manner as in Example 1 to recover the microbial cells. The washed microbial cells were suspended in 45 mL of deionized water and 5 mL of hydrogen peroxide solution of the same specification as used in Example 1 was added to the cell suspension. The mixture was transferred to a 200 mL capacity eggplant-shaped flask, which was placed on an oil bath at 100° C. for 1 hour for reaction. After completion of the reaction, the reaction mixture was cooled down to room temperature and the solid component PHA was separated by centrifugation. The separated PHA was resuspended in distilled water and again centrifuged to wash off the residual hydrogen peroxide solution. Further, this washing operation was repeated twice. Thereafter, the washed PHA polymer was dried under reduced pressure and the dry weight (recovered amount) was weighed. The average molecular weight and structure of the PHA sample obtained under the conditions of this treatment with hydrogen peroxide solution were analyzed by GPC and $^1$H-NMR, respectively, under the conditions described in Example 1.

Example 5

Cultured microbial cells of strain YN2 obtained by the same culture method as in Example 1 were washed with water in the same manner as in Example 1 to recover the microbial cells. The washed microbial cells were suspended in 50 mL of hydrogen peroxide solution of the same specification as used in Example 1. The mixture was transferred to a 200 mL capacity eggplant-shaped flask, which was placed on an oil bath at 100° C. for 1 hour for reaction. After completion of the reaction, the reaction mixture was cooled down to room temperature and the solid component PHA was separated by centrifugation. The separated PHA was resuspended in distilled water and again centrifuged to wash off the residual hydrogen peroxide solution. Further, this washing operation was repeated twice. Thereafter, the washed PHA polymer was dried under reduced pressure and the dry weight (recovered amount) was weighed. The average molecular weight and structure of the PHA sample obtained under the conditions of this treatment with hydrogen peroxide solution were analyzed by GPC and $^1$H-NMR, respectively, under the conditions described in Example 1.

Example 6

Cultured cells of strain YN2 obtained by the same culture method as in Example 1 were washed with water in the same manner as in Example 1 to recover the microbial cells. The washed cells were suspended in 40 mL of methanol to remove any water remained in the cells and the cells were recovered by centrifugation. Thereafter, the cells were dried under reduced pressure at room temperature.

To extract and separate PHA accumulated in the cells, the obtained dry cells were suspended in 30 mL of chloroform and agitated at 50° C. for 20 hours. After completion of the agitation, the component insoluble in chloroform was removed by filtration and the filtrate having the extracted PHA dissolved therein was recovered. The chloroform solution of PHA was concentrated by using a rotary evaporator. The concentrated chloroform solution was dripped into ice-cooled methanol to separate PHA as precipitate, which was recovered. In the same procedure, PHA was recovered from the cultured cells in 400 mL of the medium. These PHA polymers were combined and subjected to the following oxidation treatment with metachloroperbenzoic acid (MCPBA).

205 mg of the extracted and separated PHA was dissolved in 10 mL of chloroform and the solution was ice-cooled. Under ice-cooling, to this solution MCPBA (available from Kishida Chemical Co., Ltd.) dissolved in 20 mL of chloroform was added and subsequently the mixture was agitated on the ice-bath for 75 minutes. After completion of the reaction, sodium hydrogen carbonate aqueous solution was added to neutralize the reaction mixture. Then, further 50 mL of chloroform was added to separate an organic phase. The separated organic phase was dehydrated over anhydrous magnesium sulfate, and then after evaporation of the solvent dried under vacuum. The recovered PHA was weighed to obtain the dry weight (recovered amount). The average molecular weight and structure of the PHA sample obtained under the conditions of this treatment with MCPBA were analyzed by GPC and $^1$H-NMR, respectively, under the conditions described in Example 1.

Example 7

In a 500 mL shake flask, 200 mL of M9 medium containing 0.5% of commercially available yeast extract (available from Difco Laboratories Inc.) and 0.1% 5-(phenylsulfanyl)valeric acid were placed and a colony of strain H45 obtained by inoculating and culturing seed cells on an agar plate was cultured at 30° C. for 30 hours. After the culture, the microbial cells were harvested by centrifugation. To remove the residual medium components, the harvested microbial cells were suspended in 40 mL of deionized water and again centrifuged to recover the washed microbial cells.

The recovered cells were resuspended in 50 mL of commercially available hydrogen peroxide solution (containing 31% hydrogen peroxide, produced by Mitsubishi Gas Chemical Company, Inc., a standard preparation according to JIS K-8230). The cell suspension was transferred to a 200 mL eggplant-shaped flask, which was placed on an oil bath at 100° C. for 1 hour for reaction. After completion of the reaction, the reaction mixture was cooled down to room temperature and solid component PHA was separated by centrifugation. The separated PHA was resuspended in distilled water and again centrifuged to wash off the residual hydrogen peroxide solution. Further, this washing operation was repeated twice. Thereafter, the washed PHA polymer was dried under reduced pressure and the dry weight (recovered amount) was weighed. The average molecular weight and structure of the PHA sample obtained under the conditions of this treatment with hydrogen peroxide solution were analyzed by GPC and $^1$H-NMR, respectively, under the conditions described in Example 1.

Example 8

In a 500 mL shake flask, 200 mL of M9 medium containing 0.5% of commercially available D-glucose (available from Kishida Chemical Co., Ltd.) and 0.1% 5-(phenylsulfanyl)valeric acid were placed and a colony of strain H45 obtained by inoculating and culturing seed cells on an agar plate was cultured at 30° C. for 30 hours. After the culture, the microbial cells were harvested by centrifugation. Then, a 500 mL shake flask was charged with 200 mL of M9 medium containing 0.5% of commercially available glucose (available from Kishida Chemical Co., Ltd.) and 0.1% 5-(phenylsulfanyl)valeric acid but not containing $NH_4Cl$ as an inorganic nitrogen source and the harvested cells were resuspended in this medium and cultured at 30° C. for 30 hours. After the culture, the microbial cells were again harvested by centrifugation. To remove the residual medium components, the harvested cells were suspended in 40 mL of deionized water and again centrifuged to recover the washed microbial cells.

The recovered microbial cells were resuspended in 50 mL of commercially available hydrogen peroxide solution (containing 31% hydrogen peroxide, produced by Mitsubishi Gas Chemical Company, Inc., a standard preparation according to JIS K-8230). The cell suspension was transferred to a 200 mL eggplant-shaped flask, which was placed on an oil bath at 100° C. for 1 hour for reaction. After completion of the reaction, the reaction mixture was cooled down to room temperature and the solid component PHA was separated by centrifugation. The separated PHA was resuspended in distilled water and again centrifuged to wash off the residual hydrogen peroxide solution. Further, this washing operation was repeated twice. Thereafter, the washed PHA polymer was dried under reduced pressure and the dry weight (recovered amount) was weighed. The average molecular weight and structure of the PHA sample obtained under the conditions of this treatment with hydrogen peroxide solution were analyzed by GPC and $^1$H-NMR, respectively, under the conditions described in Example 1.

Example 9

In a 500 mL shake flask, 200 mL of M9 medium containing 0.5% of commercially available glycerol (available from Kishida Chemical Co., Ltd.) and 0.1% 5-(phenylsulfanyl)valeric acid were placed and a colony of strain H45 obtained by inoculating and culturing seed cells on an agar plate was cultured at 30° C. for 30 hours. After the culture, the microbial cells were harvested by centrifugation. Then, in a 500 mL shake flask, 200 mL of M9 medium containing 0.5% of commercially available glycerol (available from Kishida Chemical Co., Ltd.) and 0.1% 5-(phenylsulfanyl)valeric acid but not containing $NH_4Cl$ as an inorganic nitrogen source was placed and the harvested cells were resuspended in this medium and cultured at 30° C. for 30 hours. After the culture the cells were again harvested by centrifugation. To remove the residual medium components, the harvested cells were suspended in 40 mL of deionized water and again centrifuged to recover the washed cells.

The recovered cells were resuspended in 50 mL of commercially available hydrogen peroxide solution (containing 31% hydrogen peroxide, produced by Mitsubishi Gas Chemical Company, Inc., a standard preparation according to JIS K-8230). The cell suspension was transferred to a 200 mL eggplant-shaped flask, which was placed on an oil bath at 100° C. for 1 hour for reaction. After completion of the reaction, the reaction mixture was cooled down to room temperature and the solid component PHA was separated by centrifugation. The separated PHA was resuspended in distilled water and again centrifuged to wash off the residual hydrogen peroxide solution. Further, this washing operation was repeated twice. Thereafter, the washed PHA polymer was dried under reduced pressure and the dry weight (recovered amount) was weighed. The average molecular weight and structure of the PHA sample obtained under the conditions of this treatment with hydrogen peroxide solution were analyzed by GPC and $^1$H-NMR, respectively, under the conditions described in Example 1

Table 1 shows the recovery amount (dry weight) and molecular weight of the PHA samples prepared in Examples 1 to 9 above.

TABLE 1

| Examples | Recovery amount (mg) | Mn × 10⁴ | Mw × 10⁴ |
|---|---|---|---|
| 1 | 70 | 3.6 | 7.2 |
| 2 | 76 | 3.7 | 7.2 |
| 3 | 79 | 3.9 | 7.1 |
| 4 | 79 | 4.0 | 7.1 |
| 5 | 81 | 4.0 | 7.0 |
| 6 | 144 | 5.7 | 8.9 |
| 7 | 66 | 3.3 | 6.3 |
| 8 | 84 | 3.9 | 6.9 |
| 9 | 79 | 3.7 | 6.6 |

Mn: Number average molecular weight
Mw: Weight average molecular weight

Table 2 shows content ratios of units of the following chemical formulae (6), (7) and (8), calculated from the results of $^1$H-NMR analyses of the PHA samples prepared in Examples 1 to 9 above.

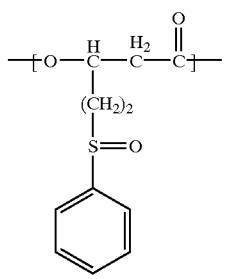

(6)

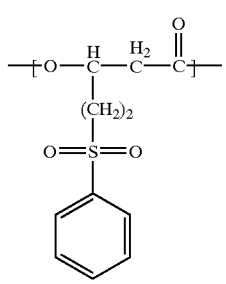

(7)

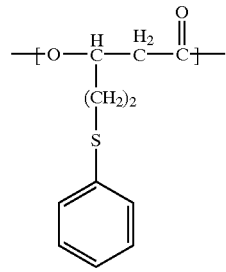

(8)

TABLE 2

| Examples | Unit (6) (mol %) | Unit (7) (mol %) | Unit (8) (mol %) |
|---|---|---|---|
| 1 | 46 | 54 | 0 |
| 2 | 79 | 21 | 0 |
| 3 | 72 | 2 | 26 |
| 4 | 13 | 0 | 87 |
| 5 | 23 | 0 | 77 |
| 6 | 100 | 0 | 0 |
| 7 | 44 | 56 | 0 |
| 8 | 48 | 52 | 0 |
| 9 | 44 | 56 | 0 |

The content ratio of each unit is expressed in percentage of the content (mole) of each unit where the total (mole) of units having an aromatic ring in the side chain is regarded as 100%.

Figure 2:
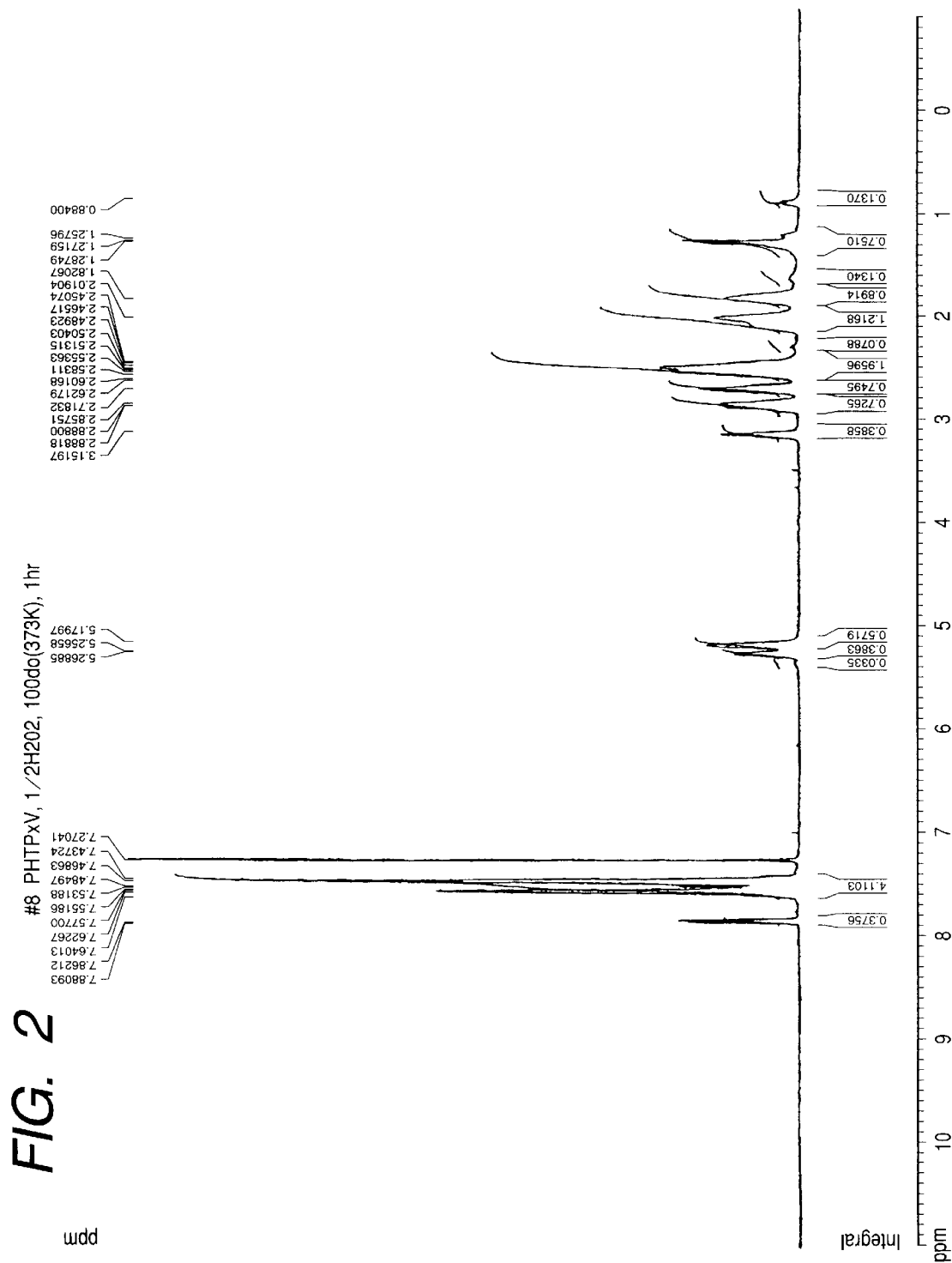
FIG. 2 is a $^1$H-NMR spectrum chart of a PHA containing a unit of the chemical formula (6) and a unit of the chemical formula (7) prepared in Example 2.
Figure 3:
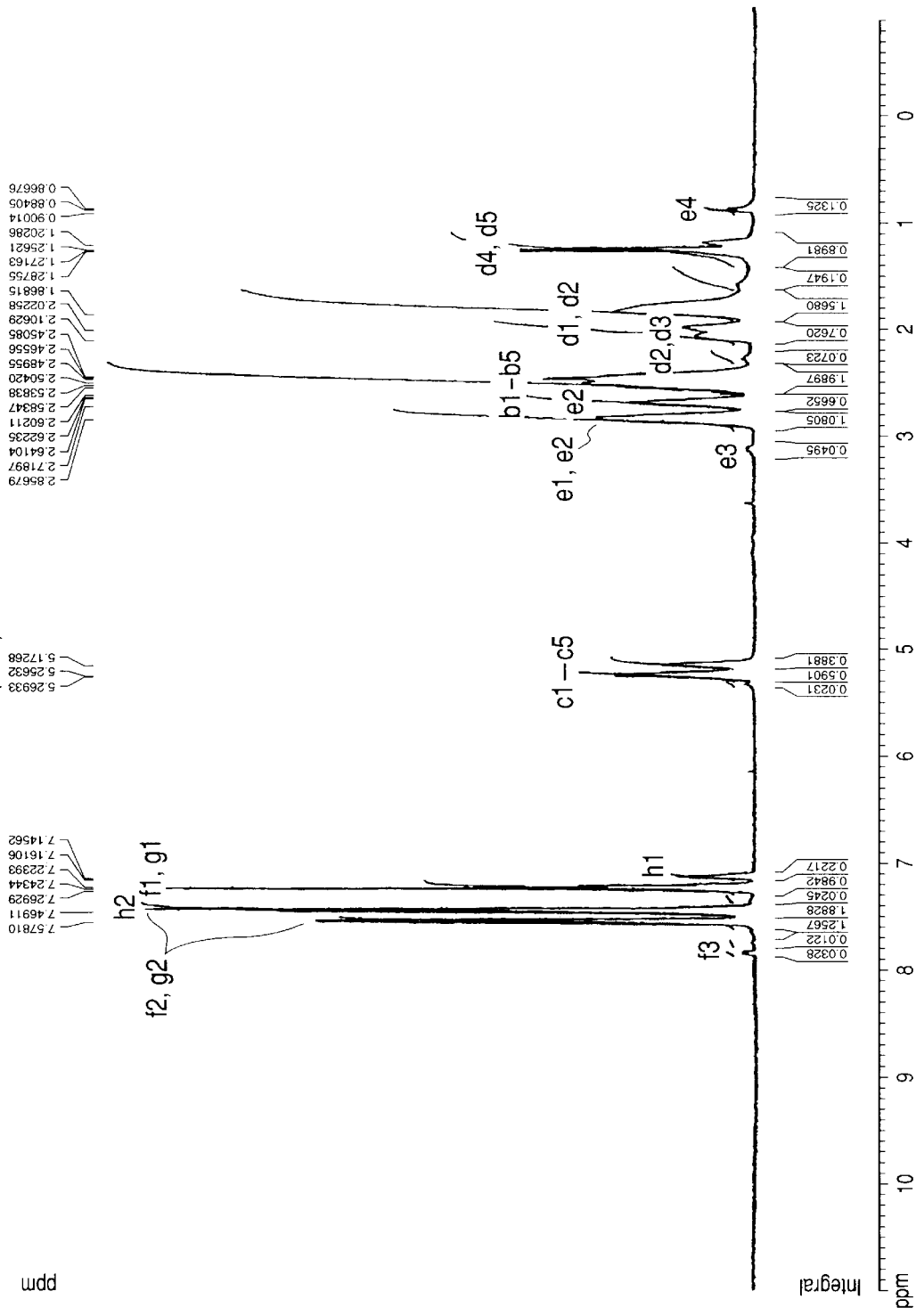
FIG. 3 is a $^1$H-NMR spectrum chart of a PHA containing a unit of the chemical formula (7) and a unit of the chemical formula (8) prepared in Example 3.
Figure 4:
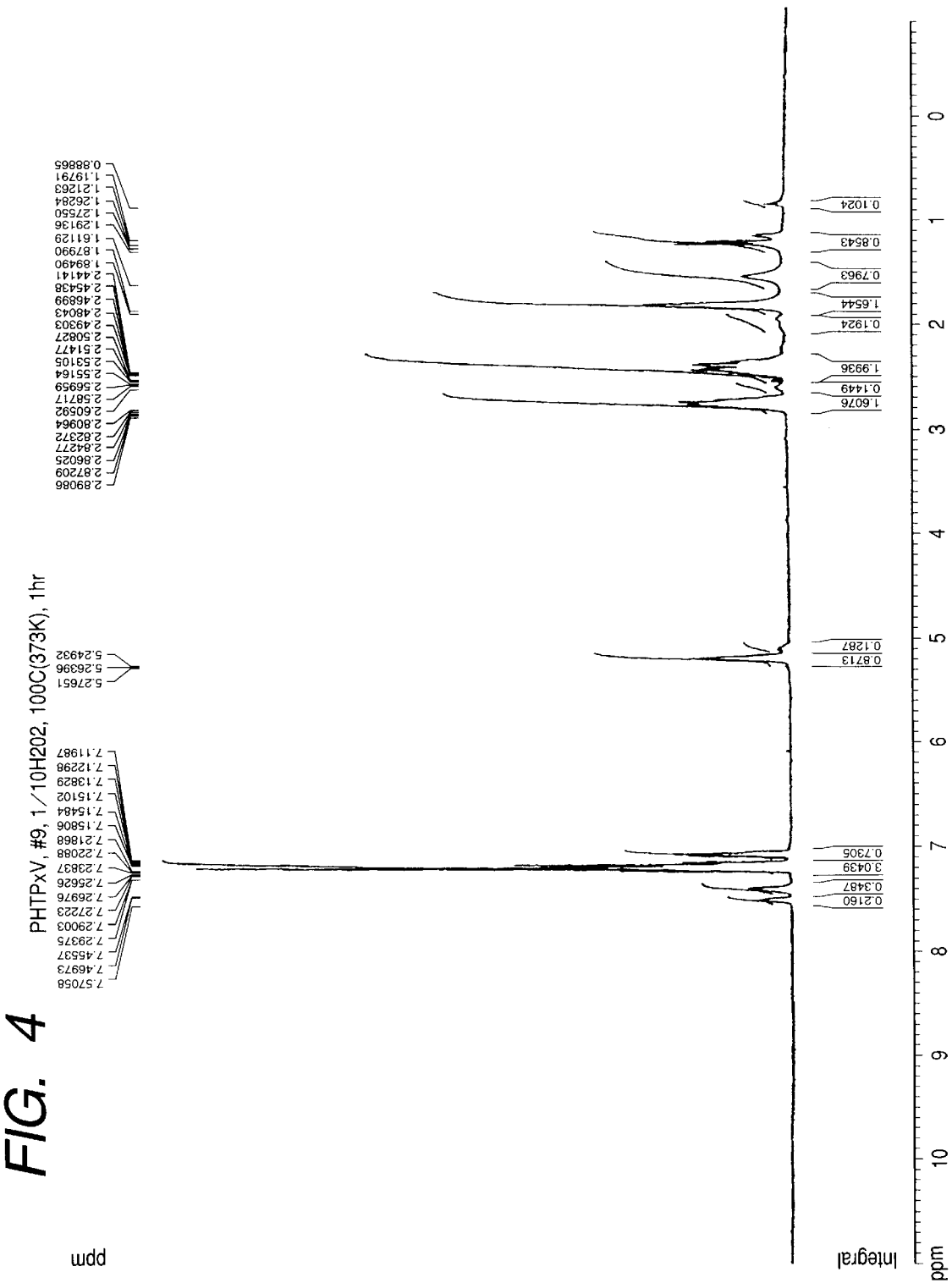
FIG. 4 is a $^1$H-NMR spectrum chart of a PHA containing a unit of the chemical formula (6) and a unit of the chemical formula (8) prepared in Example 4.
Figure 5:
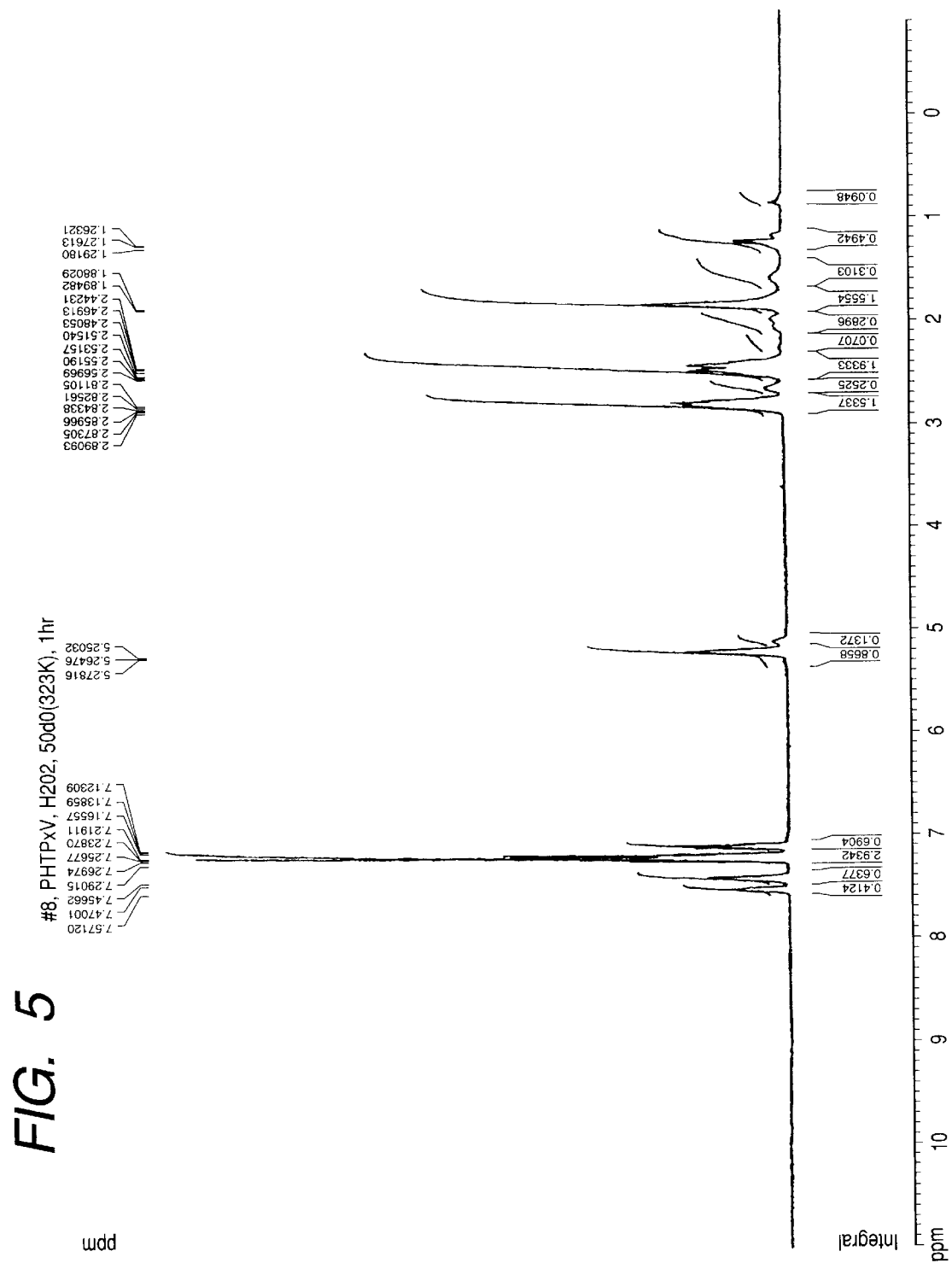
FIG. 5 is a $^1$H-NMR spectrum chart of a PHA containing a unit of the chemical formula (6) and a unit of the chemical formula (8) prepared in Example 5.
Figure 6:
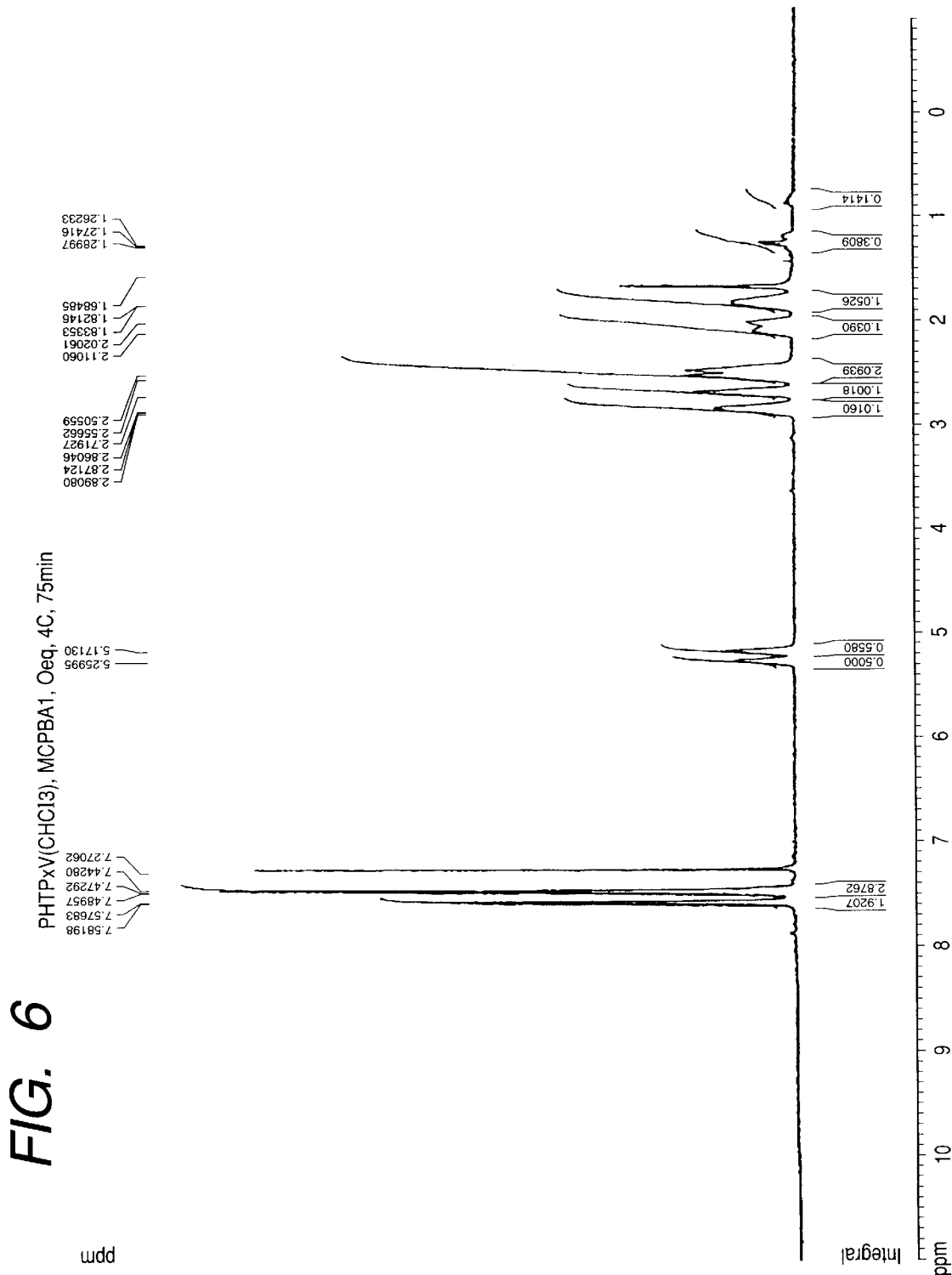
FIG. 6 is a $^1$H-NMR spectrum chart of a PHA containing a unit of the chemical formula (6) prepared in Example 6.

FIGS. 1 to 6 illustrate $^1$H-NMR spectrum of the PHA samples prepared in Examples 1 to 6, respectively, under different oxidation conditions using hydrogen peroxide (Example 1: FIG. 1, Example 2: FIG. 2, Example 3: FIG. 3, Example 4: FIG. 4, Example 5: FIG. 5, and Example 6: FIG. 6). In particular, as for the $^1$H-NMR spectrum of the PHA sample obtained in Example 3 that contains all the three units of the chemical formulae (6), (7) and (8), FIG. 3 also shows assignment of each spectral line corresponding to the position of carbon atoms described in the following chemical formula (24).

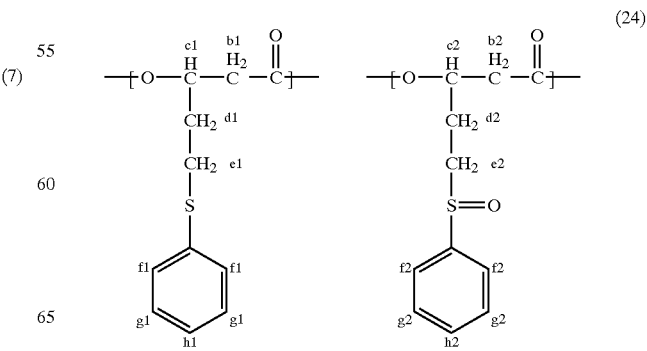

(24)

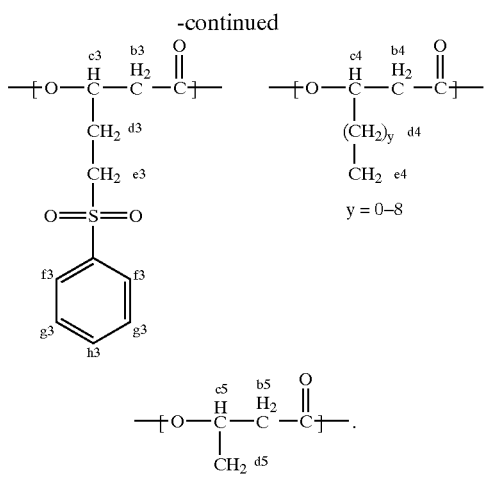

In addition, the PHA polymers obtained in Examples 1 to 9 contain, in addition to the units of the chemical formulae (6), (7) and (8) above, a linear 3-hydroxyalkanoate unit of the general formula (4) below and a linear 3-hydroxyalkenoate unit of the general formula (5) below and the proportion (mol %) of the total of the unit of the general formula (4) and the unit of the general formula (5) occupying all the units is 7 mol % in Example 1, 10 in mol % in Example 2, 12 mol % in Example 3, 13 mol % in Example 4, 7 mol % in Example 5, 9 mol % in Example 6, 6 mol % in Example 7, 8 mol % in Example 8, and 7 mol % in Example 9.

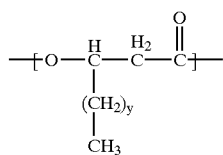

(wherein y is 0 or an integer selected from 1 to 8).

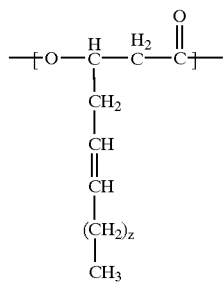

(wherein z is an integer selected from 3 and 5).

Next, Examples 10 to 14 hereinbelow show production examples for the production of PHAs containing at least one of a unit having a 3-hydroxy-4-(phenylsulfinyl)butyrate unit and a 3-hydroxy-4-(phenylsulfonyl)butyrate unit in the polymer molecule, or PHAs containing a 3-hydroxy-4-(phenylsulfanyl)butyrate unit in addition to the above-mentioned two kinds of units by cultivating a PHA producing microorganism in a medium containing 4-(phenylsulfanyl)butyric acid as a raw material to produce a desired PHA and then subjecting the PHA produced by the microorganism to oxidation treatment with a peroxide compound.

Example 10

A 500 mL shake flask was charged with 200 mL of M9 medium containing 0.5% of commercially available D-glucose (available from Kishida Chemical Co., Ltd.) and 0.1% 4-(phenylsulfanyl)butyric acid and a colony of strain YN2 obtained by inoculating and culturing seed cells on an agar plate was cultured at 30° C. for 48 hours. After the culture, the microbial cells were harvested by centrifugation. Then, a 500 mL shaking flask was charged with 200 mL of M9 medium containing 0.5% of commercially available D-glucose (available from Kishida Chemical Co., Ltd.) and 0.1% 5-(phenylsulfanyl)butyric acid but not containing NH4Cl as an inorganic nitrogen source and the harvested cells were resuspended in this medium and cultured at 30° C. for 48 hours. After the culture the cells were again harvested by centrifugation. To remove the residual medium components, the harvested cells were suspended in 40 mL of deionized water and again centrifuged to recover the washed cells.

The recovered cells were resuspended in 50 mL (containing 31% hydrogen peroxide, produced by Mitsubishi Gas Chemical Company, Inc., a standard preparation according to JIS K-8230). The cell suspension was transferred to a 200 mL eggplant-shaped flask, which was placed on an oil bath at 100° C. for 1 hour for reaction. After completion of the reaction, the reaction mixture was cooled down to room temperature and the solid component PHA was separated by centrifugation. The separated PHA was resuspended in distilled water and again centrifuged to wash off the residual hydrogen peroxide solution. Further, this washing operation was repeated twice. Thereafter, the washed PHA polymer was dried under reduced pressure and the dry weight (recovered amount) was weighed. The average molecular weight and structure of the PHA sample obtained under the conditions of this treatment with hydrogen peroxide solution were analyzed by GPC and $^1$H-NMR, respectively, under the conditions described in Example 1.

Example 11

A 500 mL shake flask was charged with 200 mL of M9 medium containing 0.5% of commercially available polypeptone (available from Wako Pure Chemicals Industries, Ltd.) and 0.1% 5-(phenylsulfanyl)butyric acid and a colony of strain YN2 obtained by inoculating and culturing seed cells on an agar plate was cultured at 30° C. for 48 hours. After the culture, the microbial cells were harvested by centrifugation. Then, a 500 mL shaking flask was charged with 200 mL of M9 medium containing 0.5% of commercially available sodium pyruvate (available from Kishida Chemical Co., Ltd.) and 0.1% 4-(phenylsulfanyl)butyric acid but not containing NH$_4$Cl as an inorganic nitrogen source was placed and the harvested cells were resuspended in this medium and cultured at 30° C. for 48 hours. After the culture the cells were again harvested by centrifugation. To remove the residual medium components, the harvested cells were suspended in 40 mL of deionized water and again centrifuged to recover the washed cells.

The recovered cells were resuspended in 50 mL of commercially available hydrogen peroxide solution (containing 31% hydrogen peroxide, produced by Mitsubishi Gas Chemical Company, Inc., a standard preparation according

Example 12

Cultured cells of strain YN2 obtained by the same culture method as in Example 10 were washed with water in the same manner as in Example 10 to recover the microbial cells. The washed microbial cells were suspended in 40 mL of deionized water and the microbial cells were disrupted by using a French press (French Press 5501, manufactured by Ohtake Seisakusho Co.). Disrupted microbial cells were centrifuged at 4° C. and 3000 G for 30 minutes to separate insoluble fractions. Thereafter, to wash off the residual soluble component, 40 mL of distilled water was added to the insoluble fraction and again centrifuged at 4° C. and 3000 G for 30 minutes to recover the washed PHA.

The obtained crude PHA sample was suspended in 45 mL of deionized water and 5 mL of the hydrogen peroxide solution described in Example 1 was added to the obtained suspension and the mixture was treated at 100° C. for 1 hour. After completion of the reaction, the reaction mixture was cooled down to room temperature and the solid PHA was centrifuged. After the separation, the PHA was resuspended in distilled water and again centrifuged to wash off the residual hydrogen peroxide solution. Further, this washing operation was repeated twice. Thereafter, the washed PHA polymer was dried under reduced pressure and the dry weight (recovered amount) was weighed. The average molecular weight and structure of the PHA sample obtained under the conditions of this treatment with hydrogen peroxide solution were analyzed by GPC and $^1$H-NMR, respectively, under the conditions described in Example 1.

Example 13

A 500 mL shaking flask was charged with 200 mL of M9 medium containing 0.1% of commercially available n-nonanoic acid (available from Kishida Chemical Co., Ltd.) and 0.1% 4-(phenylsulfanyl)butyric acid and a colony of strain YN2 obtained by inoculating and culturing seed cells on an agar plate was cultured at 30° C. for 48 hours. After the culture, the microbial cells were harvested by centrifugation. To remove the residual medium components, the harvested microbial cells were suspended in 40 mL of deionized water and again centrifuged to recover the washed microbial cells.

The recovered cells were resuspended in 50 mL of commercially available hydrogen peroxide solution (containing 31% hydrogen peroxide, produced by Mitsubishi Gas Chemical Company, Inc., a standard preparation according to JIS K-8230). The cell suspension was transferred to a 200 mL eggplant-shaped flask, which was placed on an oil bath at 100° C. for 1 hour for reaction. After completion of the reaction, the reaction mixture was cooled down to room temperature and the solid component PHA was separated by centrifugation. The separated PHA was resuspended in distilled water and again centrifuged to wash off the residual hydrogen peroxide solution. Further, this washing operation was repeated twice. Thereafter, the washed PHA polymer was dried under reduced pressure and the dry weight (recovered amount) was weighed. The average molecular weight and structure of the PHA sample obtained under the conditions of this treatment with hydrogen peroxide solution were analyzed by GPC and $^1$H-NMR, respectively, under the conditions described in Example 1.

Example 14

A 500 mL shaking flask was charged with 200 mL of M9 medium containing 0.5% of commercially available sodium glutamate and 0.1% 4-(phenylsulfanyl)butyric acid and a colony of strain YN2 obtained by inoculating and culturing seed cells on an agar plate was cultured at 30° C. for 48 hours. After the culture, the microbial cells were harvested by centrifugation. To remove the residual medium components, the harvested microbial cells were suspended in 40 mL of deionized water and again centrifuged to recover the washed microbial cells.

The recovered cells were resuspended in 50 mL of commercially available hydrogen peroxide solution (containing 31% hydrogen peroxide, produced by Mitsubishi Gas Chemical Company, Inc., a standard preparation according to JIS K-8230). The cell suspension was transferred to a 200 mL eggplant-shaped flask, which was placed on an oil bath at 100° C. for 1 hour for reaction. After completion of the reaction, the reaction mixture was cooled down to room temperature and the solid component PHA was separated by centrifugation. The separated PHA was resuspended in distilled water and again centrifuged to wash off the residual hydrogen peroxide solution. Further, this washing operation was repeated twice. Thereafter, the washed PHA polymer was dried under reduced pressure and the dry weight (recovered amount) was weighed. The average molecular weight and structure of the PHA sample obtained under the conditions of this treatment with hydrogen peroxide solution were analyzed by GPC and $^1$H-NMR, respectively, under the conditions described in Example 1.

Table 3 shows the recovery amount (dry weight) and molecular weight of the PHA samples prepared in Examples 10 to 14 above.

TABLE 3

| Examples | Recovery amount (mg) | Mn × $10^3$ | Mw × $10^3$ |
| --- | --- | --- | --- |
| 10 | 55 | 3.3 | 6.6 |
| 11 | 57 | 3.4 | 6.6 |
| 12 | 51 | 3.6 | 6.5 |
| 13 | 38 | 4.2 | 8.1 |
| 14 | 39 | 3.4 | 6.5 |

Mn: Number average molecular weight
Mw: Weight average molecular weight

Table 4 shows content ratios of units of the following chemical formulae (9), (10) and (11), calculated from the results of $^1$H-NMR analyses of the PHA samples prepared in Examples 10 to 14 above.

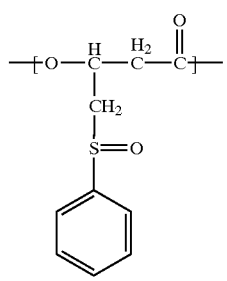
(9)

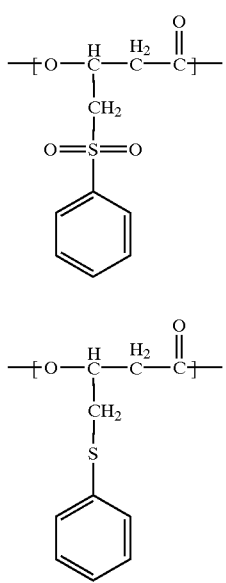
(10)

(11)

TABLE 4

| Examples | Unit (9) (mol %) | Unit (10) (mol %) | Unit (11) (mol %) |
| --- | --- | --- | --- |
| 10 | 42 | 58 | 0 |
| 11 | 44 | 56 | 0 |
| 12 | 21 | 0 | 79 |
| 13 | 61 | 39 | 0 |
| 14 | 40 | 60 | 0 |

Contents ratio of each unit is expressed in percentage of the content (mole) of each unit taking the total (mole) of units having an aromatic ring in the side chain as 100%.

In addition, the PHA polymers obtained in Examples 10 to 13 contain, in addition to the units of the chemical formulae (9), (10) and (11) above, a linear 3-hydroxyalkanoate unit of the general formula (4) below and a linear 3-hydroxyalkenoate unit of the general formula (5) below and the total proportion (mol %) of the unit of the general formula (4) and the unit of the general formula (5) occupying all the units is 14 mol % in Example 10, 7 mol % in Example 11, 8 mol % in Example 12, 92 mol % in Example 13, and 5 mol % in Example 14.

(4)

y = 0–8

(wherein y is 0 or an integer selected from 1 to 8).

(5)

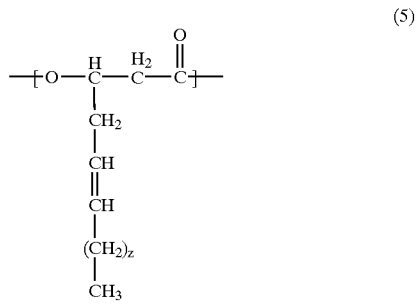

z = 3,5

(wherein z is an integer selected from 3 and 5).

Further, Examples 15 to 18 hereinbelow show production examples for the production of PHAs containing at least one of a unit having a 3-hydroxy-5-[(4-fluorophenyl)sulfinyl]valerate unit and a 3-hydroxy-5[(4-fluorophenyl)sulfonyl]valerate unit in the polymer molecule, or PHAs containing a 3-hydroxy-5-[(4-fluorophenyl)sulfanyl]valerate unit in addition to the above-mentioned two kinds of units, by cultivating a PHA producing microorganism in a medium containing 5-[(4-fluorophenyl)sulfanyl]valeric acid as a raw material to produce a desired PHA and then subjecting the PHA produced by the microorganism to oxidation treatment with a peroxide compound.

Example 15

A 500 mL shake flask was charged with 200 mL of M9 medium containing 0.5% of commercially available polypeptone (available from Wako Pure Chemical-Industries, Ltd.) and 0.1% 5-[(4-fluorophenyl)sulfanyl]valeric acid and a colony of strain YN2 obtained by inoculating and culturing seed cells on an agar plate was inoculated and cultured at 30° C. for 24 hours. After the culture, the microbial cells were harvested by centrifugation. To remove the residual medium components, the harvested cells were suspended in 40 mL of deionized water and again centrifuged to recover the washed cells.

The recovered cells were resuspended in 50 mL of commercially available hydrogen peroxide solution (containing 31% hydrogen peroxide, produced by Mitsubishi Gas Chemical Company, Inc., a standard preparation according to JIS K-8230). The cell suspension was transferred to a 200 mL eggplant-shaped flask, which was placed on an oil bath at 100° C. for 1 hour for reaction. After completion of the reaction, the reaction mixture was cooled down to room temperature and solid component PHA was separated by centrifugation. The separated PHA was resuspended in distilled water and again centrifuged to wash off the residual hydrogen peroxide solution. Further, this washing operation was repeated twice. Thereafter, the washed PHA polymer was dried under reduced pressure and the dry weight (recovered amount) was weighed. The average molecular weight and structure of the PHA sample obtained under the conditions of this treatment with hydrogen peroxide solution were analyzed by GPC and $^1$H-NMR, respectively, under the conditions described in Example 1.

Example 16

A 500 mL shake flask was charged with 200 mL of M9 medium containing 0.5% of commercially available polypeptone (available from Wako Pure Chemical Industries, Ltd.) and 0.1% 5-[(4-fluorophenyl)sulfanyl] valeric acid and a colony of strain H45 obtained by inoculating and culturing seed cells on an agar plate was cultured at 30° C. for 24 hours. After the culture, the microbial cells were harvested by centrifugation. To remove the residual medium components, the harvested cells were suspended in 40 mL of deionized water and again centrifuged to recover the washed cells.

The recovered cells were resuspended in 50 mL of commercially available hydrogen peroxide solution (containing 31% hydrogen peroxide, produced by Mitsubishi Gas Chemical Company, Inc., a standard preparation according to JIS K-8230). The cell suspension was transferred to a 200 mL eggplant-shaped flask, which was placed on an oil bath at 100° C. for 1 hour for reaction. After completion of the reaction, the reaction mixture was cooled down to room temperature and solid component PHA was separated by centrifugation. The separated PHA was resuspended in distilled water and again centrifuged to wash off the residual hydrogen peroxide solution. Further, this washing operation was repeated twice. Thereafter, the washed PHA polymer was dried under reduced pressure and the dry weight (recovered amount) was weighed. The average molecular weight and structure of the PHA sample obtained under the conditions of this treatment with hydrogen peroxide solution were analyzed by GPC and $^1$H-NMR, respectively, under the conditions described in Example 1.

Example 17

A 500 mL shake flask was charged with 200 mL of M9 medium containing 0.5% of commercially available polypeptone (available from Wako Pure Chemical Industries, Ltd.) and 0.1% 5-[(4-fluorophenyl)sulfanyl] valeric acid and a colony of strain YN2 obtained by culturing seed cells on an agar plate was inoculated and cultured at 30° C. for 24 harvested by centrifugation. To remove the residual medium components, the harvested cells were suspended in 40 mL of deionized water and again centrifuged to recover the washed cells.

The recovered cells were resuspended in 50 mL of commercially available hydrogen peroxide solution (containing 31% hydrogen peroxide, produced by Mitsubishi Gas Chemical Company, Inc., a standard preparation according to JIS K-8230). The cell suspension was transferred to a 200 mL eggplant-shaped flask, which was placed on an oil bath at 100° C. for 1 hour for reaction. After completion of the reaction, the reaction mixture was cooled down to room temperature and the solid component PHA was separated by centrifugation. The separated PHA was resuspended in distilled water and again centrifuged to wash off the residual hydrogen peroxide solution. Further, this washing operation was repeated twice. Thereafter, the washed PHA polymer was dried under reduced pressure and dry weight (recovered amount) was weighed. The average molecular weight and structure of the PHA sample obtained under the conditions of this treatment with hydrogen peroxide solution were analyzed by GPC and $^1$H-NMR, respectively, under the conditions described in Example 1.

Example 18

Cultured cells of strain YN2 obtained by the same culture method as in Example 15 were washed with water in the same manner as above to recover the microbial cells. The cells washed with water were suspended in 40 mL of deionized water and the cells were disrupted by using a French press (French Press 5501, manufactured by Ohtake Seisakusho Co.). Disrupted cells were centrifuged at 4° C. and 3000 G for 30 minutes to separate insoluble fractions. Thereafter, to wash off the residual soluble component, 40 mL of distilled water was added to the insoluble fraction and again centrifuged at 4° C. and 3000 G for 30 minutes to recover the washed PHA.

The obtained crude PHA sample was suspended in 30 mL of deionized water and 10 mL of the hydrogen peroxide solution described in Example 1 was added to the obtained suspension and the mixture was treated at 100° C. for 1 hour. After completion of the reaction, the reaction mixture was cooled down to room temperature and the solid component PHA was centrifuged. After the separation, the PHA was resuspended in distilled water and again centrifuged to wash off the residual hydrogen peroxide solution. Further, this washing operation was repeated twice. Thereafter, the washed PHA polymer was dried under reduced pressure and the dry weight (recovered amount) was weighed. The average molecular weight and structure of the PHA sample obtained under the conditions of this treatment with hydrogen peroxide solution were analyzed by GPC and $^1$H-NMR measurements, respectively, under the conditions described in Example 1.

Table 5 shows the recovery amount (dry weight) and molecular weight of the PHA samples prepared in Examples 15 to 18 above.

TABLE 5

| Examples | Recovery amount (mg) | Mn × 10$^4$ | Mw × 10$^4$ |
|---|---|---|---|
| 15 | 77 | 3.4 | 7.0 |
| 16 | 45 | 3.6 | 6.9 |
| 17 | 48 | 3.7 | 7.2 |
| 18 | 70 | 3.6 | 7.1 |

Mn: Number average molecular weight
Mw: Weight average molecular weight

Table 6 shows content ratios of units of the following chemical formulae (12), (13) and (14), calculated from the results of 1H-NMR analyses of the PHA samples prepared in Examples 15 to 18 above.

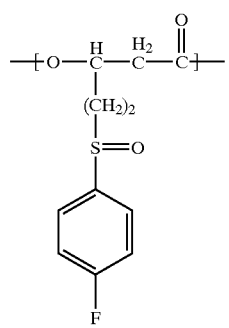

(12)

-continued

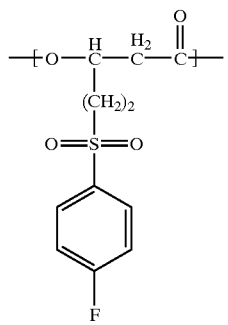
(13)

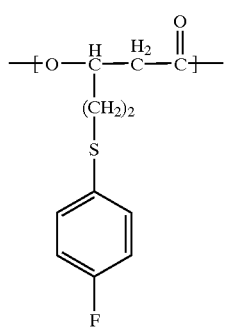
(14)

TABLE 6

| Examples | Unit (12) (mol %) | Unit (13) (mol %) | Unit (14) (mol %) |
| --- | --- | --- | --- |
| 15 | 46 | 54 | 0 |
| 16 | 47 | 53 | 0 |
| 17 | 44 | 56 | 0 |
| 18 | 75 | 4 | 21 |

The content ratio of each unit is expressed in percentage of the content (mole) of each unit taking the total (mole) of units having an aromatic ring in the side chain as 100%.

In addition, the PHA polymers obtained in Examples 15 to 18 contain, in addition to the units of the chemical formulae (12), (13) and (14) above, a linear 3-hydroxyalkanoate unit of the general formula (4) below and a linear 3-hydroxyalkenoate unit of the general formula (5) below and the total proportion (mol %) of the unit of the general formula (4) and the unit of the general formula (5) occupying all the units is 10 mol % in Example 15, 6 mol % in Example 16, 9 mol % in Example 17 and 9 mol % in Example 18.

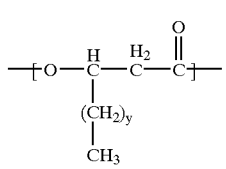
(4)

$y = 0–8$ (wherein y is 0 or an integer selected from 1 to 8).

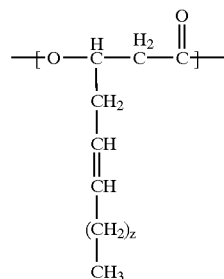
(5)

$z = 3, 5$ (wherein z is an integer selected from 3 and 5).

Example 19

A 500 mL shake flask was charged with 200 mL of M9 medium containing 0.5% of commercially available polypeptone (available from Wako Pure Chemical Industries, Ltd.) and 0.1% 5-[(3-fluorophenyl)sulfanyl] valeric acid and a colony of strain YN2 obtained by inoculating and culturing seed cells on an agar plate was cultured at 30° C. for 24 hours. After the culture, the microbial cells were harvested by centrifugation. After the culture, the microbial cells were again harvested by centrifugation. To remove the residual medium components, the harvested microbial cells were suspended in 40 mL of deionized water and again centrifuged to recover the washed microbial cells.

The recovered microbial cells were resuspended in 50 mL of commercially available hydrogen peroxide solution (containing 31% hydrogen peroxide, produced by Mitsubishi Gas Chemical Company, Inc., a standardized product of JIS K-8230). The cell suspension was transferred to a 200 mL eggplant-shaped flask, which was placed on an oil bath at 100° C. for 1 hour for reaction. After completion of the reaction, the reaction mixture was cooled down to room temperature and solid component PHA was separated by centrifugation. Thereafter, the separated PHA was resuspended in distilled water and again centrifuged to wash off the residual hydrogen peroxide solution. Further, this washing operation was repeated twice. Thereafter, the washed PHA polymer was dried under reduced pressure and its dry weight (recovered amount) was weighed. The average molecular weight and structure of the PHA sample obtained under the conditions of this treatment with the hydrogen peroxide solution were analyzed by GPC and $^1$H-NMR, respectively, under the conditions described in Example 1.

Table 7 shows the recovery amount (dry weight) and molecular weight of the PHA sample prepared in Example 19 above.

TABLE 7

| Example | Recovery amount (mg) | Mn × $10^4$ | Mw × $10^4$ |
| --- | --- | --- | --- |
| 19 | 43 | 3.0 | 6.1 |

Mn: Number average molecular weight
Mw: Weight average molecular weight

Table 8 shows contents ratios of units of the following chemical formulae (15), (16) and (17), calculated from the results of $^1$H-NMR analysis of the PHA sample prepared in Example 19 above.

(15)

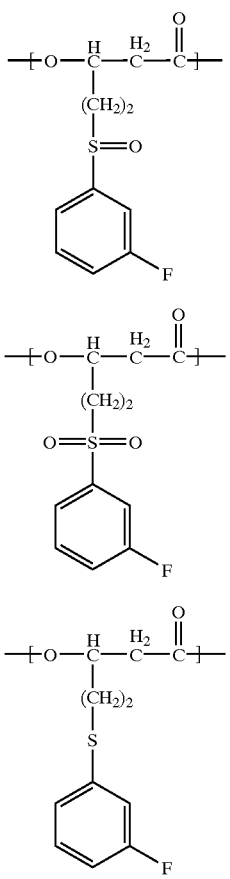

(16)

(17)

(wherein y is 0 or an integer selected from 1 to 8).

(5)

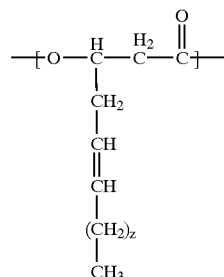

z = 3,5

(wherein z is an integer selected from 3 and 5).

Example 20

A 500 mL shake flask was charged with 200 mL of M9 medium containing 0.5% of commercially available yeast extract (available from DTFCO, Inc.) and a colony of *Pseudomonas cichorii* strain YN2 (FERM BP-7375) was inoculated and cultured at 30° C. for 8 hours. All the culture medium of the cultured strain YN2 was added to a 50 liter capacity jar fermenter having 25 liters of M9 medium containing 0.5% of commercially available polypeptone (available from Wako Pure Chemical Industries, Ltd.) and 0.1% 5-thiophenoxy valeric acid (5-(phenylsulfanyl)valeric acid) placed therein and cultured with aeration and agitation under conditions of 70 rpm and aeration amount of 9.4 liters/minute. After 48 hours, the microbial cells were recovered by centrifugation. The recovered wet microbial cells were resuspended in 1 liter of deionized water and divided into five groups with 200 mL per group, which were each centrifuged to obtain five samples. The microbial cells of the five samples were subjected to the following treatments.

[1] The cells were resuspended in 300 mL of hydrogen peroxide solution (produced by Mitsubishi Gas Chemical Company, Inc., containing 31% hydrogen peroxide, JIS K-8230) and allowed to react on an oil bath at 100° C. for 1 hour.

[2] The microbial cells were suspended in 150 mL of deionized water and 150 mL of hydrogen peroxide solution was added thereto. The mixture was allowed to react on an oil bath at 100° C. for 1 hour.

[3] The microbial cells were suspended in 225 mL of deionized water and 75 mL of hydrogen peroxide solution was added thereto. The mixture was allowed to react on an oil bath at 100° C. for 1 hour.

[4] The cells were suspended in 270 mL of deionized water and 30 mL of hydrogen peroxide solution was added thereto. The mixture was allowed to react on an oil bath at 100° C. for 1 hour.

[5] The cells were suspended in 300 mL of deionized water and disrupted by using a French press (French Press 5501, manufactured by Ohtake Seisakusho Co.). Then, the disrupted cells were centrifuged at 4° C. and 29400 m/s$^2$ (=3000 G) for 30 minutes. Thereafter, 300 mL of distilled water was further added and the mixture was centrifuged at 4° C. and 29400 m/s$^2$ (=3000 G) for 30 minutes to wash the cell fragments. The obtained precipitate was suspended in 300 mL of hydrogen peroxide solution and the suspension was allowed to react on an oil bath at 50° C. for 1 hour.

After completion of the reaction, each sample was ice-cooled and centrifuged at 4° C. and 29400 m/s$^2$ (=3000 G) for 30 minutes. Then, 300 mL of distilled water was further

TABLE 8

| Example | Unit (20) (mol %) | Unit (21) (mol %) | Unit (22) (mol %) |
|---|---|---|---|
| 19 | 48 | 52 | 0 |

The content ratio of each unit is expressed in percentage of the content (mole) of each unit taking the total (mole) of units having an aromatic ring in the side chain as 100%.

In addition, the PHA polymer obtained in Example 19 above contains, in addition to the units of the chemical formulae (15), (16) and (17) above, a linear 3-hydroxyalkanoate unit of the general formula (4) below and a linear 3-hydroxyalkenoate unit of the general formula (5) below and the total proportion (mol %) of the unit of the general formula (4) and the unit of the general formula (5) occupying all the units is 25 mol %.

(4)

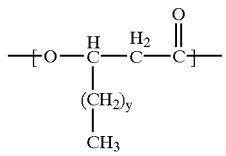

y = 0–8 added to the sample and the mixture was centrifuged at 4° C. and 29400 m/s² (=3000 G) for 30 minutes for washing. Further, this washing operation was repeated twice. The samples were each resuspended in 50 mL of deionized water and freeze-dried. The molecular weight of the samples thus obtained was measured by gel permeation chromatography (GPC) under the following GPC conditions:

Apparatus: Tosoh, HLC-8020;
Column: Polymer Laboratory, PLgel, MIXED-C (5 μm)× 2; and
Mobile Phase Solvent: 0.1 mass % LiBr containing DMF; converted on the polystyrene basis. Further, the structure of the sample was analyzed by proton-nuclear magnetic resonance apparatus (1H-NMR) under the following conditions:
Apparatus: Bruker DPX400 FT-NMR;
$^1$H Resonance frequency: 400 MHz;
Nuclide to be analyzed: $^1$H;
Solvent used: $CDCl_3$;
Reference: $TMS/CDCl_3$ sealed in a capillary; and
Temperature for measurement: room temperature.

Example 21

Each of two 500 mL capacity shake flasks was charged with 200 mL of M9 medium containing 0.5% of commercially available yeast extract and strain YN2 (FERM BP-7375) was inoculated in each flask and cultured at 30° C. for 8 hours. 2 mL each of the culture medium of the cultured strain YN2 was added to five 2 liter shake flasks having 1 liter of M9 medium containing 0.5% of commercially available polypeptone and 0.1% 5-thiophenoxy valeric acid (5-(phenylsulfanyl)valeric acid) placed therein and cultured at 125 strokes/minute at 30° C. After 48 hours, microbial cells corresponding to 5 liters of the culture medium were recovered by centrifugation. The obtained microbial cells of strain YN2, after washing with water, were resuspended in 1 liter of methanol and recovered by centrifugation followed by drying at room temperature under reduced pressure. The obtained microbial cells were suspended in 750 mL of chloroform and agitated at 50° C. for 20 hours. After completion of the agitation, the component insoluble in chloroform was removed by filtration and the chloroform solution was concentrated by using a rotary evaporator. The concentrated chloroform solution was dripped into ice-cooled methanol to obtain a PHA sample as precipitate.

The obtained sample (1.7 g) was dissolved in 80 mL of chloroform and ice-cooled. Into this, 2.0 g of MCPBA (Kishida Chemical Co., Ltd.) dissolved in 160 mL of chloroform was dripped and the mixture was agitated for 75 minutes on an ice bath.

After completion of the reaction, sodium hydrogen carbonate solution was added to neutralize the reaction mixture, to which 400 mL of chloroform was added for separation to extract an organic phase. This was dehydrated over anhydrous magnesium sulfate. After evaporation of the solvent, the solid was dried under vacuum. The obtained sample was named sample [6].

Example 22

Two 500 mL capacity shaking flasks each having 200 mL of M9 medium containing 0.5% of commercially available yeast extract placed therein were inoculated with *Pseudomonas cichorii* strain H45 (FERM BP-7374) and *Pseudomonas jessenii* strain P161 (FERM BP-7376), respectively, and the resultant was cultured at 30° C. for 8 hours. Ten 2-liter capacity shake flasks each having 1 liter of M9 medium containing 0.5% of commercially available polypeptone and 0.1% 5-thiophenoxy valeric acid (5-(phenylsulfanyl)valeric acid) placed therein were prepared. The culture media of the cultured strain H45 and the cultured strain P161 were added to five of the ten flasks, respectively, in an amount of 2 mL per flask. They were cultured at 125 strokes/minute at 30° C. After 48 hours, the microbial cells of strain H45 and strain P161, each corresponding to 5 liters of the culture medium, were recovered by centrifugation. The microbial cells of each strain were treated under the same conditions as in Example 20 [1] above to obtain a sample. The sample derived from strain H45 was named sample [7] and the sample derived from strain P161 was named sample [8]. Samples [7] and [8] were subjected to GPC and $^1$H-NMR measurement in the same manner as in Example 1.

Table 9 shows the yield and molecular weight of each sample in Examples 20 to 22.

TABLE 9

| Samples | Recovery amount (g) | Mn × 10⁴ | Mw × 10⁴ |
|---|---|---|---|
| [1] | 1.7 | 3.7 | 7.2 |
| [2] | 1.8 | 3.7 | 7.1 |
| [3] | 1.9 | 3.8 | 7.0 |
| [4] | 1.9 | 4.1 | 7.2 |
| [5] | 1.9 | 4.2 | 7.2 |
| [6] | 1.2 | 5.6 | 8.7 |
| [7] | 1.4 | 3.9 | 7.0 |
| [8] | 1.6 | 3.7 | 7.3 |

Mn: Number average molecular weight
Mw: Weight average molecular weight

Table 10 shows ratios of units of the chemical formulae (6), (7) and (8) calculated from $^1$H-NMR data on each sample.

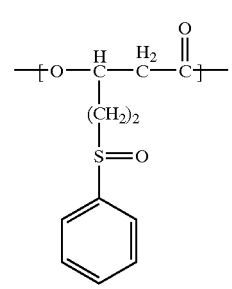

(6)

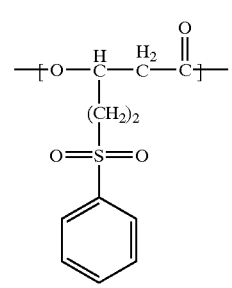

(7)

(8)

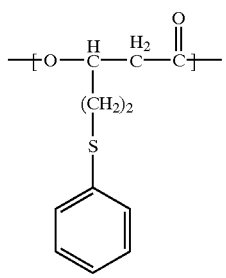

TABLE 10

| Samples | Unit (8) (mol %) | Unit (9) (mol %) | Unit (10) (mol %) |
|---|---|---|---|
| [1] | 46 | 54 | 0 |
| [2] | 79 | 21 | 0 |
| [3] | 72 | 2 | 26 |
| [4] | 13 | 0 | 87 |
| [5] | 23 | 0 | 77 |
| [6] | 100 | 0 | 0 |
| [7] | 45 | 55 | 0 |
| [8] | 46 | 54 | 0 |

Each unit ratio indicates percentage of a unit having an aromatic ring in the side chain taking the total units as 100%.

In samples [1] to [8], the ratios of linear 3-hydroxyalkanoate and 3-hydroxyalkenoate units other than the units represented by the chemical formulae (6), (7) and (8) were [1]: 7%, [2]: 10%, [3]: 12%, [4]: 13%, [5]: 7%, [6]: 9%, [7]: 6%, and [8]: 8%.

Figure 7:
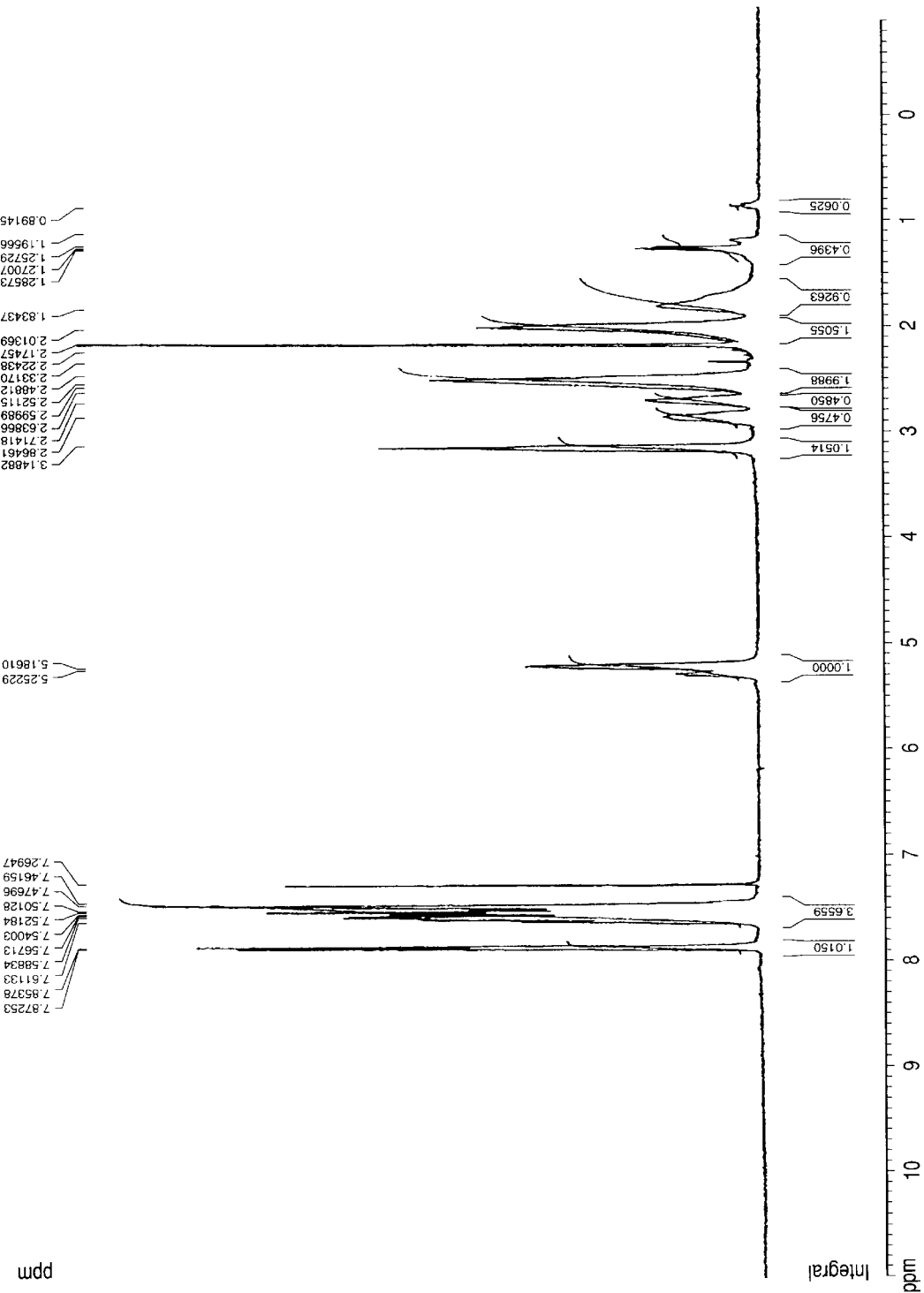
FIG. 7 is a $^1$H-NMR spectrum chart of the PHA of sample [1] in Examples 20 and 22.
Figure 8:
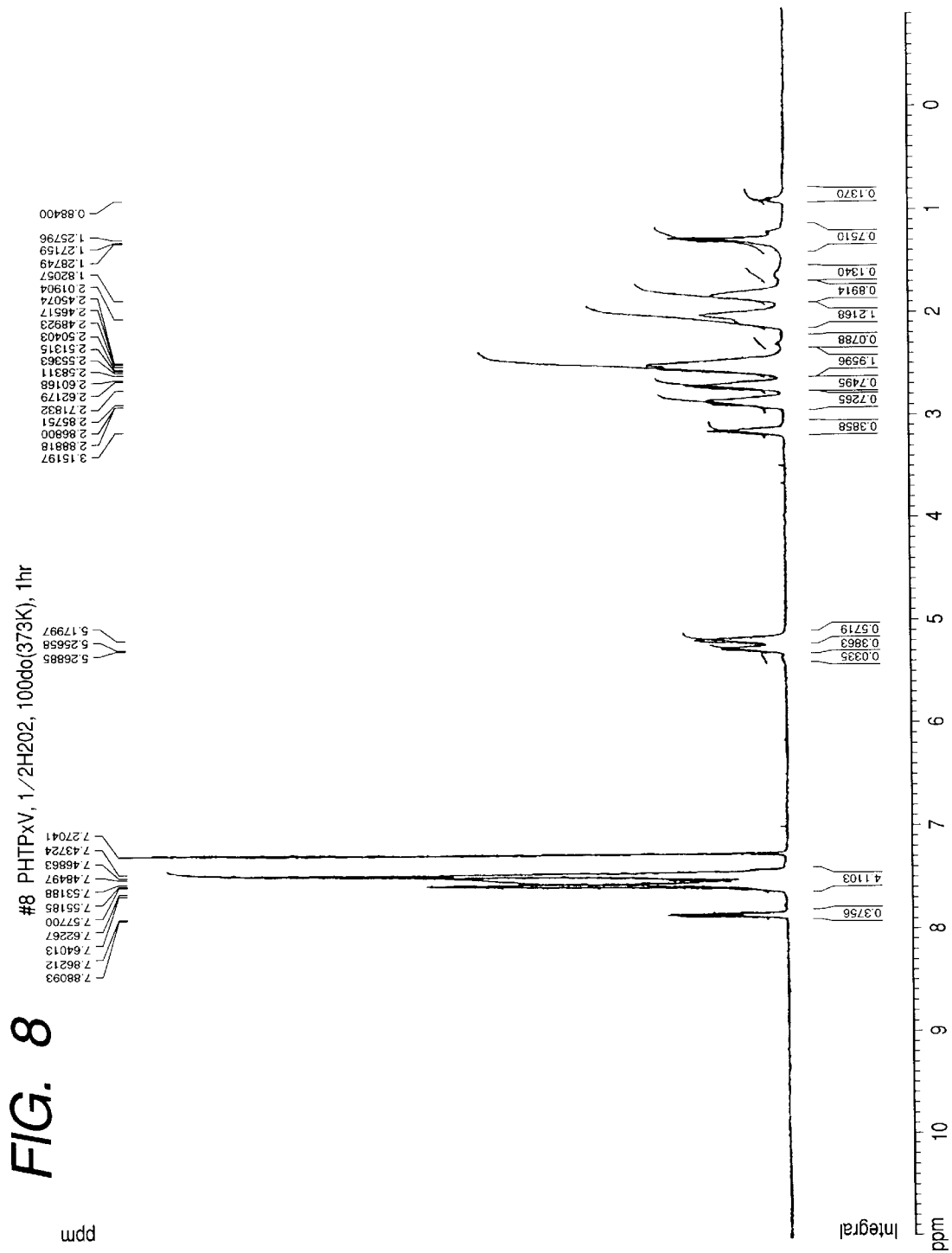
FIG. 8 is a $^1$H-NMR spectrum chart of the PHA of sample [2] in Examples 20 and 22.
Figure 9:
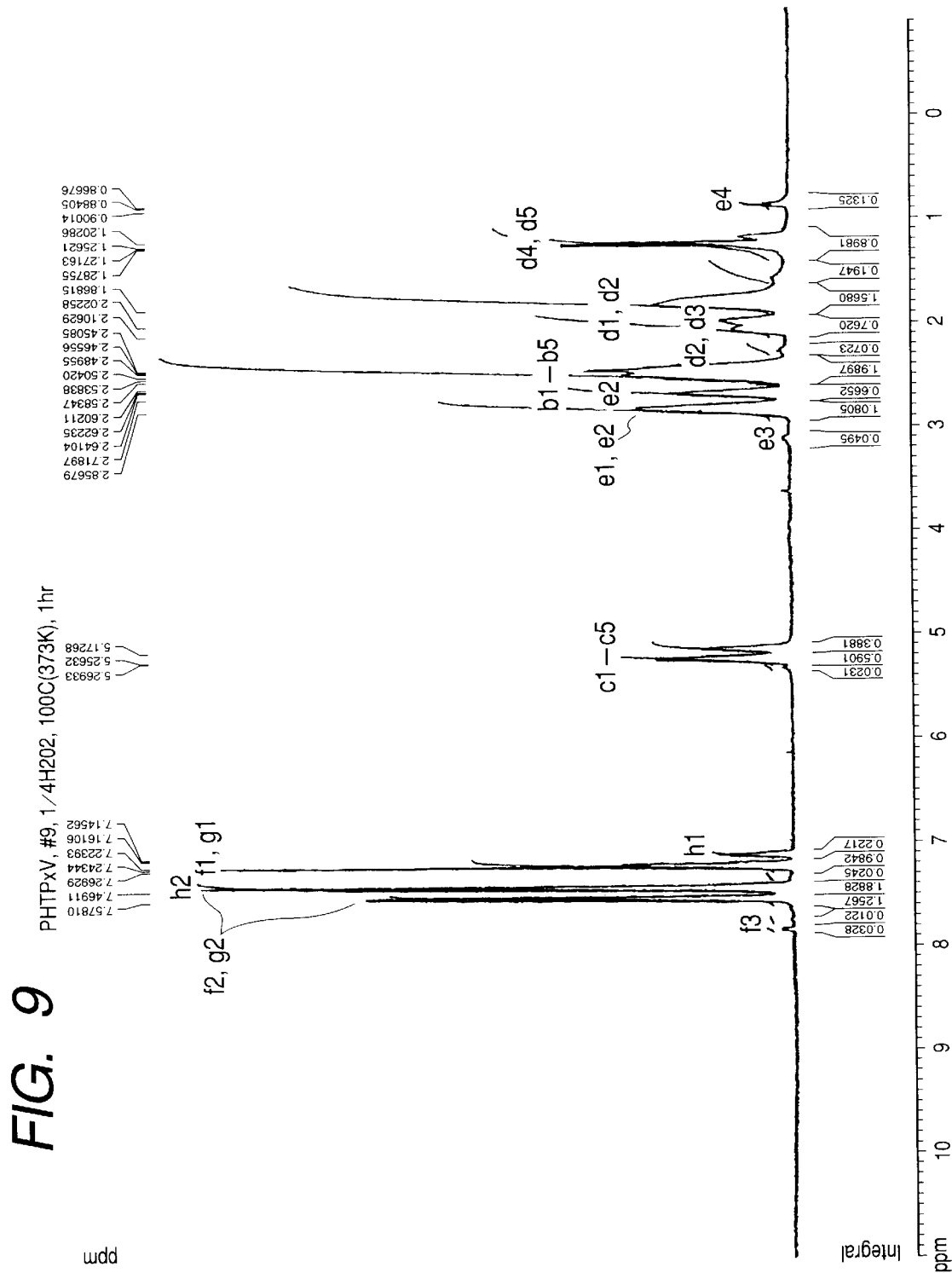
FIG. 9 is a $^1$H-NMR spectrum chart of the PHA of sample [3] in Examples 20 and 22.
Figure 10:
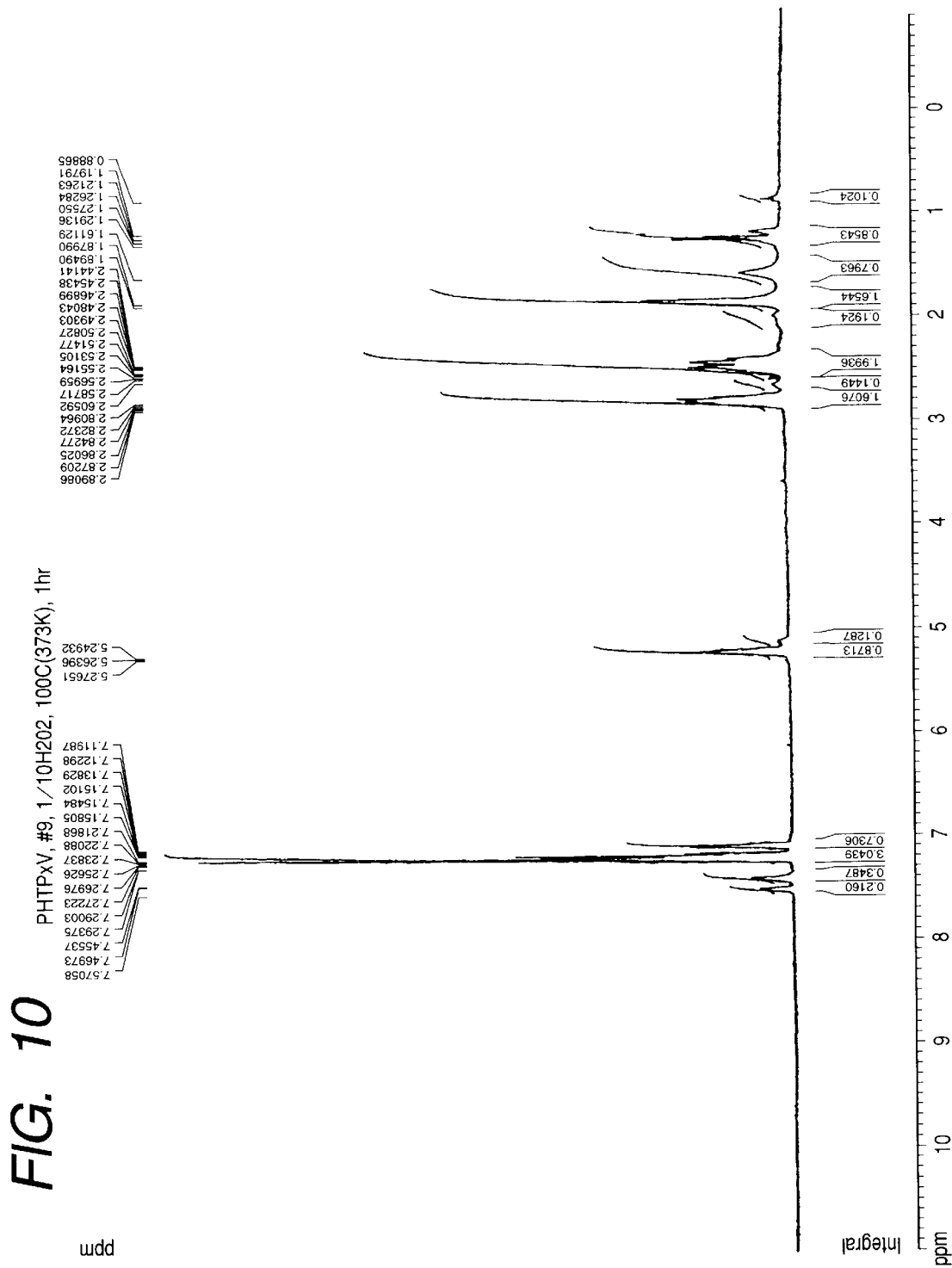
FIG. 10 is a $^1$H-NMR spectrum chart of the PHA of sample [4] in Examples 20 and 22.
Figure 11:
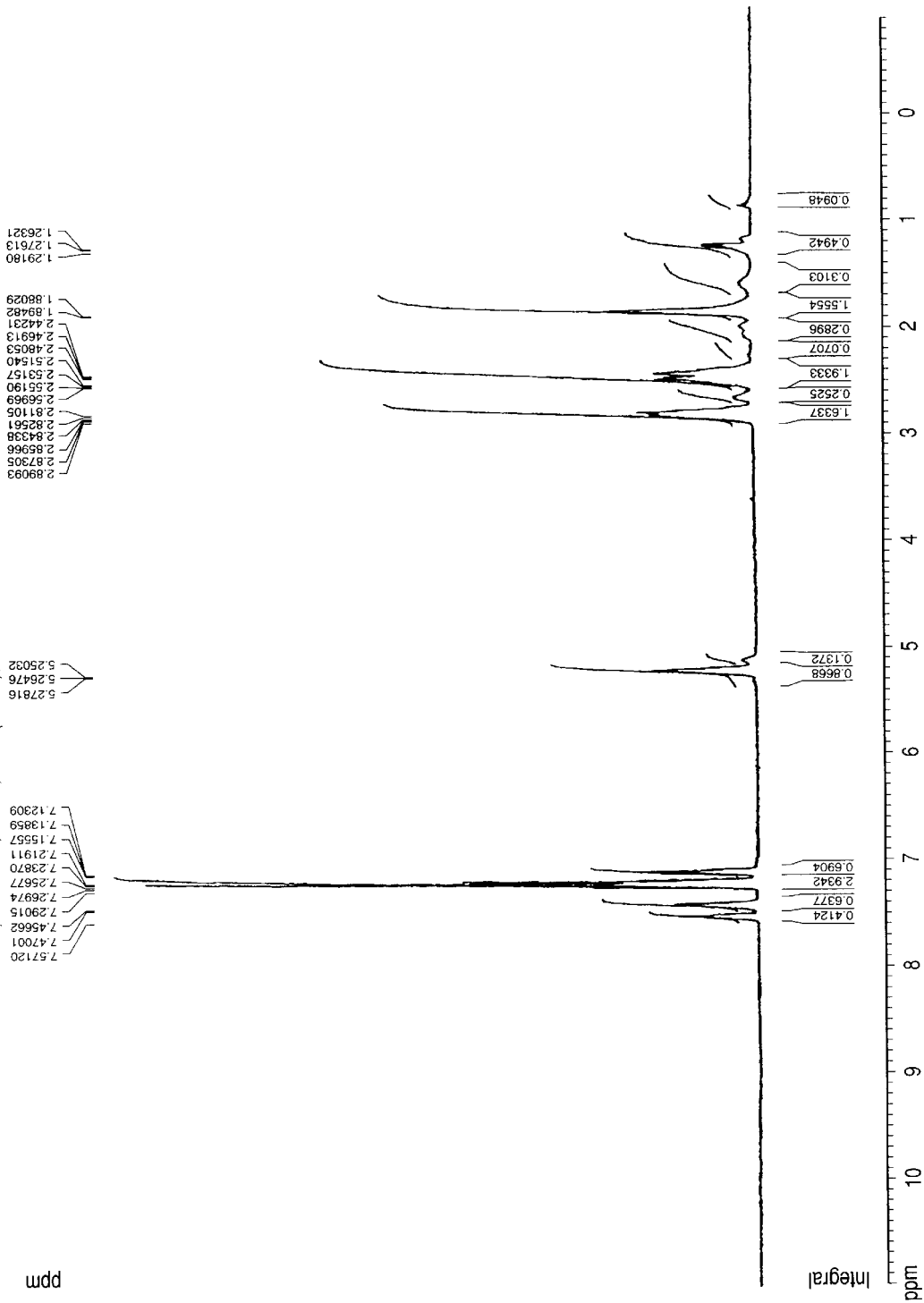
FIG. 11 is a $^1$H-NMR spectrum chart of the PHA of sample [5] in Examples 20 and 22.
Figure 12:
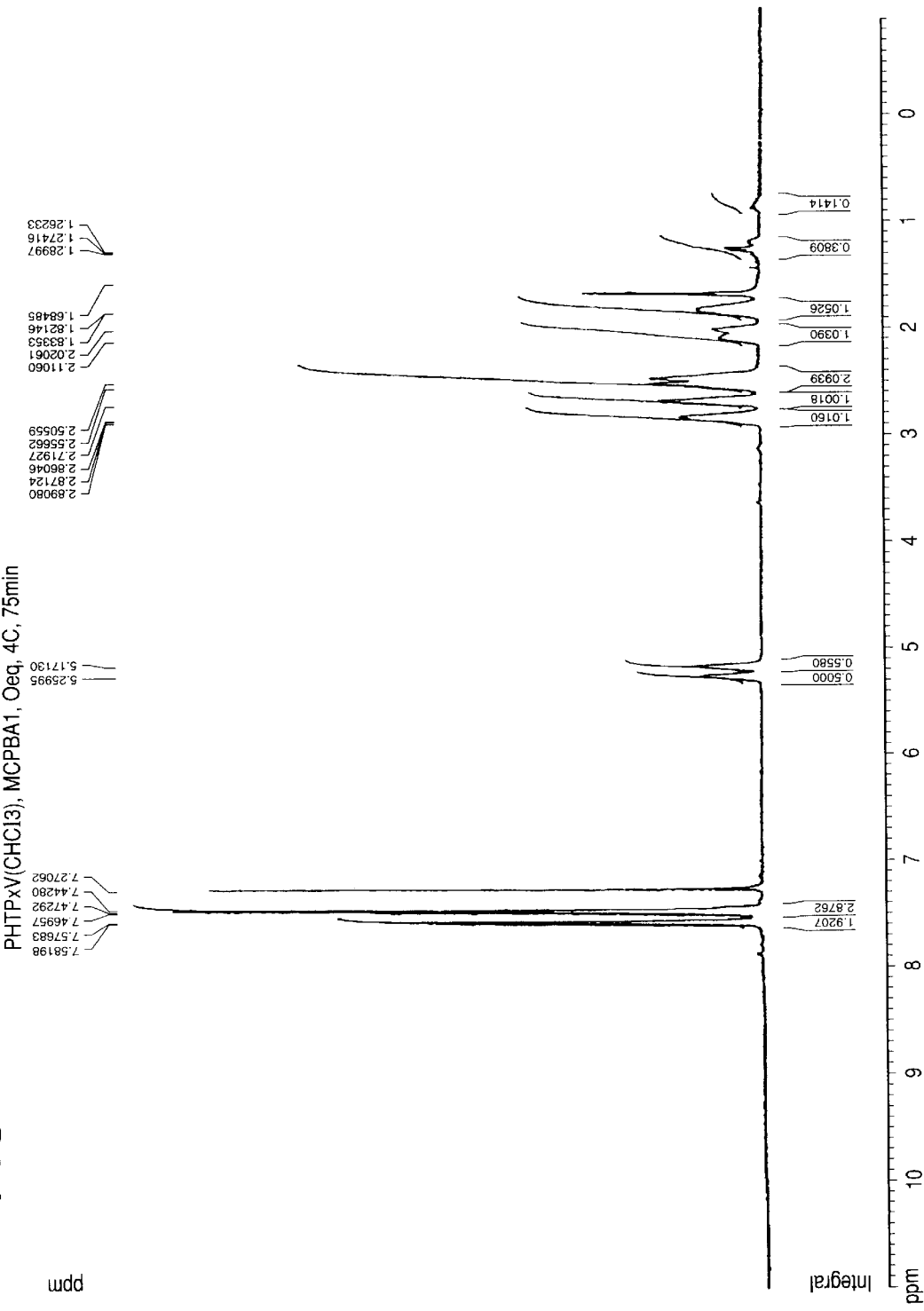
FIG. 12 is a $^1$H-NMR spectrum chart of the PHA of sample [6] in Examples 21 and 22.

FIGS. 7 to 12 show $^1$H-NMR spectrum of samples [1] to [6] out of the above-mentioned samples ([1]: FIG. 7, [2]: FIG. 8, [3]: FIG. 9, [4]: FIG. 10, [5]: FIG. 11, and [6]: FIG. 12). Among them, for the spectrum of sample [3] obtained in Example 20 containing all of the three units of the chemical formulae (6), (7) and (8) above, the attributes corresponding to the following structural formula are also shown.

(24)

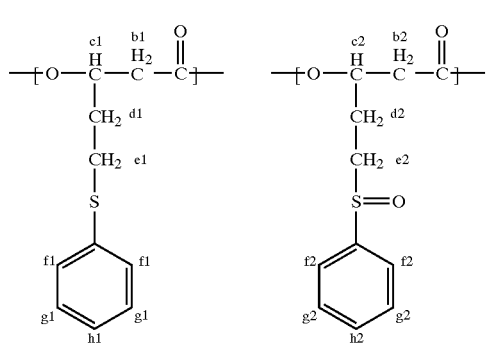

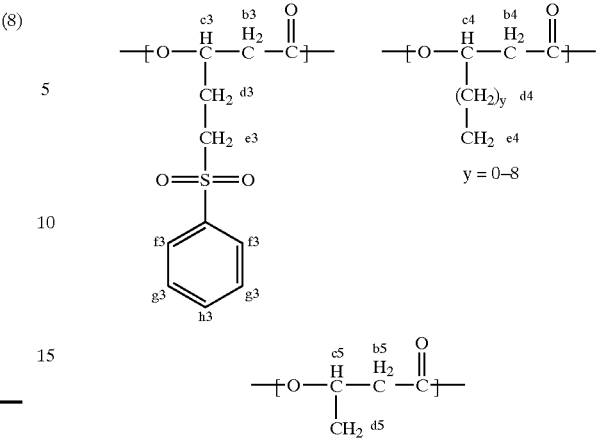

Using the compounds ([1] to [8]) thus obtained as exemplary compounds (1) to (8), various toners were prepared and evaluated in Example 25 and subsequent Examples.

Example 23

Three 500 mL capacity shake flasks each having 200 mL of M9 medium containing 0.5% of commercially available yeast extract were inoculated with strain YN2, strain H45 and strain P161, respectively, which were cultured at 30° C. for 8 hours. Fifteen 2-liter capacity shake flasks each having 1 liter of M9 medium containing 0.5% of D-glucose (produced by Kishida Chemical Co., Ltd.) and 0.1% of 4-thiophenoxy butyric acid (4-(phenylsulfanyl)butyric acid) were prepared. The culture medium of each of the three cultured strains was added to five out of the fifteen flasks in an amount of 2 mL per flask and cultured at 125 strokes/minute at 30° C. After completion of the culture for 48 hours, cells were recovered by centrifugation. The microbial cells of each strain were resuspended in five flasks charged with 1 liter of M9 medium containing 0.5% of D-glucose and 0.1% of 4-thiophenoxy butyric acid (4-(phenylsulfanyl) butyric acid), and containing no NH$_4$Cl, followed by culturing at 30° C. for 48 hours. After culturing, cells corresponding to 5 liters of the culture medium were recovered by centrifugation for each of the three strains. The microbial cells of each strain were treated under the same conditions as in Example 20 [1] above to obtain a sample. The sample derived from strain YN2 was named sample [9], the sample derived from strain H45 was named sample [10] and the sample derived from strain P161 was named sample [11]. Samples [9] to [11] were subjected to GPC and $^1$H-NMR measurements in the same manner as in Example 20. Tale 11 shows the yield and molecular weight of each of the samples.

TABLE 11

| Samples | Recovery amount (mg) | Mn × 10$^3$ | Mw × 10$^3$ |
|---|---|---|---|
| [9] | 1.3 | 3.4 | 6.9 |
| [10] | 1.1 | 3.3 | 6.3 |
| [11] | 1.2 | 3.5 | 6.5 |

Mn: Number average molecular weight
Mw: Weight average molecular weight

Table 12 shows ratios of units of the chemical formulae (9), (10) and (11) calculated from $^1$H-NMR data on each sample.

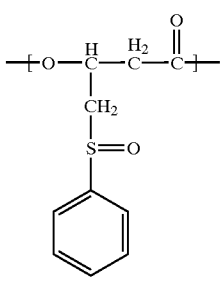

(9)

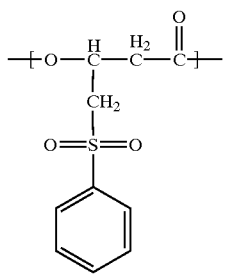

(10)

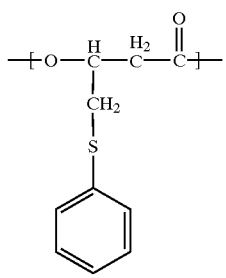

(11)

TABLE 12

| Samples | Unit (12) (mol %) | Unit (13) (mol %) | Unit (14) (mol %) |
|---|---|---|---|
| [9] | 47 | 53 | 0 |
| [10] | 46 | 54 | 0 |
| [11] | 46 | 54 | 0 |

Each unit ratio indicates a percentage of a unit having an aromatic ring in the side chain taking the total units as 100%.

In samples [9] to [11], the ratios of linear 3-hydroxyalkanoate and 3-hydroxyalkenoate units other than the units represented by the chemical formulae (9), (10) and (11) were [9]: 14%, [10]: 9%, and [11]: 11% .

Using the compounds ([9] to [11]) thus obtained as exemplary compounds (9) to (11), various toners were prepared and evaluated in Example 25 and subsequent examples.

Example 24

Three 500 mL capacity shake flasks each having 200 mL of M9 medium containing 0.5% of commercially available yeast extract were inoculated with strain YN2, strain H45 and strain P161, respectively, which were cultured at 30° C. for 8 hours. Fifteen 2-liter capacity shake flasks each having 1 liter of M9 medium containing 0.5% of polypeptone and 0.1% of 5-(4-fluorothiophenoxy)valeric acid (5-[(4-fluorophenyl)sulfanyl]valeric acid) were prepared. The culture medium of each of the three cultured strains was added to five out of the fifteen flasks in an amount of 2 mL per flask and cultured at 125 strokes/minute at 30° C. After culturing for 48 hours, microbial cells corresponding to 5 liters of the culture medium were recovered by centrifugation for each of the three strains. The microbial cells of each strain were treated under the same conditions as in Example 20 [1] above to obtain a sample. The sample derived from strain YN2 was named sample [12], the sample derived from strain H45 was named sample [13] and the sample derived from strain P161 was named sample [14]. The three samples were subjected to GPC and $^1$H-NMR measurements in the same manner as in Example 20.

Table 13 shows the yield and molecular weight of each of the samples.

TABLE 13

| Samples | Recovery amount (mg) | Mn × $10^4$ | Mw × $10^4$ |
|---|---|---|---|
| [12] | 1.8 | 3.4 | 7.2 |
| [13] | 1.1 | 3.4 | 6.9 |
| [14] | 1.1 | 3.5 | 7.1 |

Mn: Number average molecular weight
Mw: Weight average molecular weight

Table 14 shows ratios of units of the chemical formulae (12), (13) and (14) calculated from $^1$H-NMR data on each sample.

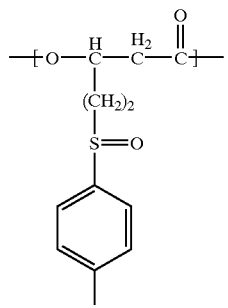

(12)

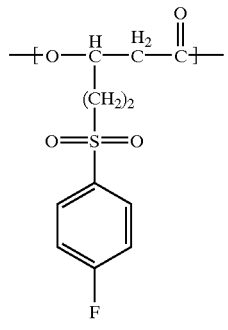

(13)

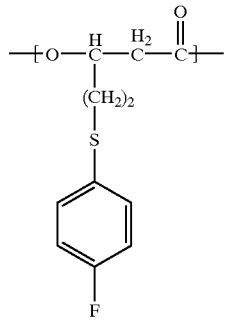

(14)

TABLE 14

| Samples | Unit (16) (mol %) | Unit (17) (mol %) | Unit (18) (mol %) |
|---|---|---|---|
| [12] | 47 | 53 | 0 |
| [13] | 48 | 52 | 0 |
| [14] | 46 | 54 | 0 |

Each unit ratio indicates a percentage of a unit having an aromatic ring in the side chain taking the total units as 100%.

In samples [12] to [14], the ratios of linear 3-hydroxyalkanoate and 3-hydroxyalkenoate units other than the units represented by the chemical formulae (12), (13) and (14) above were [12]: 10%, [13]: 8%, and [14]: 9%.

Using the compounds ([12] to [14]) thus obtained as exemplary compounds (12) to (14), various toners were prepared and evaluated in Example 25 and subsequent Examples.

Next, various kinds of toners were produced by using the charge control agents produced in the same manner as in Examples 20 to 24 in the methods selected from the methods of the present invention and evaluated (Examples 25 to 99).

Example 25

First, 0.1 M $Na_3PO_4$ aqueous solution and 1 M $CaCl_2$ aqueous solution were prepared. A 20-liter reaction vessel of a TK type homomixer (manufactured by Tokushu Kika Kogyo Co., Ltd.) were charged with 451 parts of the 0.1 M $Na_3PO_4$ aqueous solution and 709 parts of deionized water and was agitated at 10,000 rpm. 68 parts of the 1 M $CaCl_2$ aqueous solution were slowly added to the above-mentioned flask heated to 60° C. with agitation by the homomixer to obtain a dispersion medium containing $Ca_3(PO_4)_2$.

| | |
|---|---|
| Styrene | 180 parts |
| 2-Ethylhexyl acrylate | 20 parts |
| Paraffin wax (m.p. 75° C.) | 60 parts |
| C.I. Pigment Blue 15:3 | 10 parts |
| Styrene-dimethylaminoethyl Methacrylate copolymer (Mw = 40,000, Mw / Mn = 3.2, amine value = 55) | 10 parts |
| Exemplary compound (1) | 4 parts |

In the above formulation, only C.I. Pigment Blue 15:3 and styrene were preliminarily mixed. Then, all the above formulation was heated to 60° C. to melt and dispersed to form a monomer mixture. Further, while keeping the mixture at 60° C., 10 parts of 2,2'-azobis(2,4-dimethylvaleronitrile) as a polymerization initiator were added thereto to prepare a monomer composition.

The monomer composition was added to the dispersion medium prepared in the 20-liter reaction vessel of the homomixer. The resulting mixture was agitated at 10,000 rpm for 20 minutes by using the homomixer at 60° C. under a nitrogen atmosphere to granulate the monomer composition. Thereafter, polymerization was performed at 60° C. for 10 hours while agitating the granules by using a paddle-type agitating vane.

After completion of the polymerization reaction, the reaction product was cooled, added hydrochloric acid to dissolve $Ca_3(PO_4)_2$, filtered, washed with water and dried to produce blue polymer particles (1).

Measurement of the particle size of the obtained blue polymer particle (1) by using Coulter Counter Multisizer (available from Coulter K.K.) revealed that they had a weight average particle size of 8.5 μm with a sharp particle size distribution. Also, it showed that they had a fine powder amount (the proportion of particles having 3.17 μm or less in number distribution) of 4.9 number %.

0.6 parts of silane coupling agent-treated silica having an amino group whose BET surface area is 170 m2/g was externally added to 100 parts of the obtained blue polymer particles (1) to produce blue toner (1) of the present invention.

7 parts of the toner were mixed with 93 parts of fluoroacrylic resin-coated ferrite carrier to form a two-component blue developer (1) for magnetic brush development.

Examples 26 to 38

Blue toners (2) to (14) in Examples 26 to 38 were obtained in the same manner as in Example 25 except that instead of Exemplary compound (1), 2.0 parts by weight of Exemplary compounds (2) to (14) were used. The characteristics of these toners were measured in the same manner as in Example 6 and the results obtained are shown in Table 7. Using the toners, two-component blue developers (2) to (14) were obtained in the same manner as in Example 6.

Comparative Example 1

Comparative blue toner 15 of Comparative Example 1 was obtained in the same manner as in Example 25 except that no exemplary compound was used. The characteristics of the toner were measured in the same manner as in Example 25 and the results obtained are shown in Table 15. Using the toner, a two-component blue developer 15 of Comparative Example 1 was obtained in the same manner as in Example 25.

Evaluation

For the two-component blue developers (1) to (14) obtained in Examples 25 to 38 and a two-component blue developer 15 obtained in Comparative Example 1, toner charge amounts after 10 seconds or 300 seconds agitation were measured according to the measurement method for charge amount as described above under a normal temperature and normal humidity environment (25°, 60% RH) and a high temperature and high humidity environment (30° C., 80% RH). The measured values of a two-component blow-off charge amount were rounded off to the first decimal place and evaluated according to the following standards. Table 15 shows the results obtained.

Chargeability

A: Very good (+30.0 to +40.0 μC/g)
B: Good (+20.0 to +29.9 μC/g)
C: Practically usable (+10.0 to +19.9 μC/g)
D: Practically unusable (+9.9 μC/g or less)

TABLE 15

Charging characteristics of blue toners (1) to (14)

| | | | Particle size distribution | | Chargeability | | | |
| | | | | | Normal temperature and normal humidity (Q/M) | | High temperature and high humidity (Q/M) | |
| Examples | Indicated compound No. | Toner No.: blue | Weight average particle size (μm) | Fine powder amount (number %) | 10 seconds agitation | 300 seconds agitation | 10 seconds agitation | 300 seconds agitation |
|---|---|---|---|---|---|---|---|---|
| 6 | 1 | 1 | 8.5 | 4.9 | A | A | A | A |
| 7 | 2 | 2 | 8.6 | 5.2 | B | A | B | A |
| 8 | 3 | 3 | 8.3 | 5.5 | B | B | C | B |
| 9 | 4 | 4 | 8.5 | 6.3 | C | B | C | C |
| 10 | 5 | 5 | 8.4 | 6.0 | C | B | C | C |
| 11 | 6 | 6 | 8.3 | 5.1 | B | B | B | B |
| 12 | 7 | 7 | 8.2 | 5.1 | A | A | A | A |
| 13 | 8 | 8 | 8.2 | 4.9 | A | A | A | A |
| 14 | 9 | 9 | 8.5 | 6.0 | B | A | B | A |
| 15 | 10 | 10 | 8.6 | 6.1 | B | A | B | A |
| 16 | 11 | 11 | 8.6 | 5.9 | B | A | B | B |
| 17 | 12 | 12 | 8.2 | 5.5 | A | A | A | A |
| 18 | 13 | 13 | 8.2 | 5.7 | A | A | A | A |
| 19 | 14 | 14 | 8.1 | 5.8 | A | A | B | A |
| Comparative Example 1 | — | 15 | 8.3 | 5.3 | D | D | D | D |

Examples 39 to 52

Yellow toners (1) to (14) in examples 39 to 52 were prepared in the same manner as in Example 25 except that 4 parts by weight of Exemplary compounds (1) to (14) were used and that 7 parts by weight of a yellow colorant (C.I. Pigment Yellow 17) in place of the cyan colorant.

The characteristics of the toners were measured in the same manner as in Example 25 and the results obtained are shown in Table 16. Using the toners, two-component yellow developers (1) to (14) were obtained in the same manner as in Example 25.

Comparative Example 2

Comparative yellow toner 15 of Comparative Example 2 was obtained in the same manner as in Example 25 except that no exemplary compound was used and 7 parts by weight of a yellow colorant (C.I. Pigment Yellow 17) was used in place of the cyan colorant. The characteristics of the toner were measured in the same manner as in Example 25 and the results obtained are shown in Table 16. Using the toner, a two-component yellow developer 15 of Comparative Example 2 was obtained in the same manner as in Example 25.

Evaluation

For the two-component yellow developers (1) to (14) obtained in Examples 39 to 52 and the two-component yellow developer 15 obtained in Comparative Example 2. toner charge amounts after 10 seconds or 300 seconds agitation were measured according to the measurement method for charge amount as described above under a normal temperature and normal humidity environment (25° C., 60% RH) and a high temperature and high humidity environment (30° C., 80% RH). The measured values of a two-component blow-off charge amount were rounded off to the first decimal place and evaluated according to the following standards. Table 16 shows the results obtained.

Chargeability

A: Very good (+30.0 to +40.0 μC/g)
B: Good (+20.0 to +29.9 μC/g)
C: Practically usable (+10.0 to +19.9 μC/g)
D: Practically unusable (+9.9 μC/g or less)

TABLE 16

Charging characteristics of yellow toners (1) to (14)

| | | | Particle size distribution | | Chargeability | | | |
| | | | | | Normal temperature and normal humidity Q/M | | High temperature and high humidity (Q/M) | |
| Examples | Indicated compound No. | Toner No.: yellow | Weight average particle size (μm) | Fine powder amount (number %) | 10 seconds agitation | 300 seconds agitation | 10 seconds agitation | 300 seconds agitation |
|---|---|---|---|---|---|---|---|---|
| 20 | 1 | 1 | 8.2 | 5.0 | A | A | A | A |
| 21 | 2 | 2 | 8.4 | 5.2 | A | A | B | A |

TABLE 16-continued

Charging characteristics of yellow toners (1) to (14)

| | | | Particle size distribution | | Chargeability | | | |
|---|---|---|---|---|---|---|---|---|
| | | | | | Normal temperature and normal humidity (Q/M) | | High temperature and high humidity (Q/M) | |
| Examples | Indicated compound No. | Toner No.: yellow | Weight average particle size (μm) | Fine powder amount (number %) | 10 seconds agitation | 300 seconds agitation | 10 seconds agitation | 300 seconds agitation |
| 22 | 3 | 3 | 8.3 | 5.8 | C | B | C | B |
| 23 | 4 | 4 | 8.3 | 6.3 | C | B | C | C |
| 24 | 5 | 5 | 8.1 | 6.3 | C | B | C | C |
| 25 | 6 | 6 | 8.2 | 5.5 | B | A | B | B |
| 26 | 7 | 7 | 7.8 | 5.5 | A | A | A | A |
| 27 | 8 | 8 | 8.2 | 5.5 | A | A | A | A |
| 28 | 9 | 9 | 7.9 | 5.9 | B | A | B | A |
| 29 | 10 | 10 | 7.9 | 5.9 | B | A | B | B |
| 30 | 11 | 11 | 7.9 | 5.3 | B | A | B | B |
| 31 | 12 | 12 | 7.8 | 6.0 | A | A | A | A |
| 32 | 13 | 13 | 8.0 | 5.8 | A | A | A | A |
| 33 | 14 | 14 | 8.0 | 5.9 | A | A | B | A |
| Comparative Example 2 | — | 15 | 7.2 | 4.9 | D | D | D | D |

Examples 53 to 66

Black toners (1) to (14) of examples 53 to 66 were prepared in the same manner as in Example 25 except that 4 parts by weight of Exemplary compounds (1) to (14) were used and a carbon black was used in place of the cyan colorant.

The characteristics of the toners were measured in the same manner as in Example 25 and the results obtained are shown in Table 17. Using the toners, two-component black developers (1) to (14) were obtained in the same manner as in Example 25.

Comparative Example 3

A black toner 15 in Comparative Example 3 was obtained in the same manner as in Example 25 except that no exemplary compound was used and 10 parts by weight of a carbon black was used in place of the cyan colorant. The characteristics of the toner were measured in the same manner as in Example 25 and the results obtained are shown in Table 17. Using the toner, a two-component black developer 15 of Comparative Example 3 was obtained in the same manner as in Example 25.

Evaluation

For the two-component black developers (1) to (14) obtained in Examples 53 to 66 and the two-component yellow developer 15 obtained in Comparative Example 3 toner charge amounts after 10 seconds or 300 seconds agitation were measured according to the measurement method for charge amount as described above under a normal temperature and normal humidity environment (25° C., 60% RH) and a high temperature and high humidity environment (30° C., 80% RH). The measured values of a two-component blow-off charge amount were rounded off to the first decimal place and evaluated according to the following standards. Table 17 shows the results obtained.

Chargeability

A: Very good (+30.0 to +40.0 μC/g)
B: Good (+20.0 to +29.9 μC/g)
C: Practically usable (+10.0 to +19.9 μC/g)
D: Practically unusable (+9.9 μC/g or less)

TABLE 17

Charging characteristics of black toners (1) to (14)

| | | | Particle size Distribution | | Chargeability | | | |
|---|---|---|---|---|---|---|---|---|
| | | | | | Normal temperature and normal humidity (Q/M) | | High temperature and high humidity (Q/M) | |
| Examples | Indicated compound No. | Toner No.: black | Weight average particle size (μm) | Fine powder amount (number %) | 10 seconds agitation | 300 seconds agitation | 10 seconds agitation | 300 seconds agitation |
| 34 | 1 | 1 | 8.0 | 5.5 | A | A | A | A |
| 35 | 2 | 2 | 8.0 | 5.2 | A | A | B | A |
| 36 | 3 | 3 | 8.4 | 5.4 | B | B | C | B |

TABLE 17-continued

Charging characteristics of black toners (1) to (14)

| | | | Particle size Distribution | | Chargeability | | | |
|---|---|---|---|---|---|---|---|---|
| | | | | | Normal temperature and normal humidity (Q/M) | | High temperature and high humidity (Q/M) | |
| Examples | Indicated compound No. | Toner No.: black | Weight average particle size (μm) | Fine powder amount (number %) | 10 seconds agitation | 300 seconds agitation | 10 seconds agitation | 300 seconds agitation |
| 37 | 4 | 4 | 8.3 | 6.0 | C | B | C | C |
| 38 | 5 | 5 | 8.1 | 5.8 | C | B | C | C |
| 39 | 6 | 6 | 8.8 | 5.3 | B | A | B | B |
| 40 | 7 | 7 | 8.0 | 5.3 | A | A | A | A |
| 41 | 8 | 8 | 7.9 | 5.5 | A | A | A | A |
| 42 | 9 | 9 | 8.2 | 5.4 | A | A | B | A |
| 43 | 10 | 10 | 8.1 | 5.5 | A | A | B | A |
| 44 | 11 | 11 | 7.9 | 5.9 | B | A | B | B |
| 45 | 12 | 12 | 8.1 | 6.3 | A | A | A | A |
| 46 | 13 | 13 | 7.8 | 5.8 | A | A | B | A |
| 47 | 14 | 14 | 8.0 | 5.8 | A | A | B | A |
| Comparative Example 3 | — | 15 | 7.9 | 5.3 | D | C | D | C |

Examples 67 to 80

Magenta toners (1) to (14) of examples 67 to 80 were prepared in the same manner as in Example 25 except that 4 parts by weight of Exemplary compounds (1) to (14) was used and 12 parts by weight of a magenta colorant (C.I. Pigment Red 122) was used in place of the cyan colorant.

The characteristics of the toners were measured in the same manner as in Example 25 and the results obtained are shown in Table 18. Using the toners, two-component magenta developers (1) to (14) were obtained in the same manner as in Example 25.

Comparative Example 4

Magenta toner 15 of Comparative Example 4 was obtained in the same manner as in Example 25 except that no exemplary compound was used and 12 parts by weight of a magenta colorant (C.I. Pigment Red 122) was used in place of the cyan colorant. The characteristics of the toner were measured in the same manner as in Example 25 and the results obtained are shown in Table 18. Using the toner, a two-component magenta developer 15 of Comparative Example 4 was obtained in the same manner as in Example 25.

Evaluation

For the two-component magenta developers (1) to (14) obtained in Examples 67 to 80 and the two-component yellow developer 15 obtained in Comparative Example 4 of toner charge amounts after 10 seconds or 300 seconds agitation were measured according to the measurement method for charge amount as described above under of a normal temperature and normal humidity environment (25° C., 60% RH) and a high temperature and high humidity environment (30° C., 80% RH). The measured values of a two-component blow-off charge amount were rounded off to one decimal place and evaluated according to the following standards. Table 18 shows the results obtained.

Chargeability

A: Very good (+30.0 to +40.0 μC/g)
B: Good (+20.0 to +29.9 μC/g)
C: Practically usable (+10.0 to +19.9 μC/g)
D: Practically unusable (+9.9 μC/g or less)

TABLE 18

Charging characteristics of magenta toners (1) to (14)

| | | | Particle size distribution | | Changeability | | | |
|---|---|---|---|---|---|---|---|---|
| | | | | | Normal temperature and normal humidity (Q/M) | | High temperature and high humidity (Q/M) | |
| Examples | Indicated compound No. | Toner No.: red | Weight average particle size (μm) | Fine powder amount (number %) | 10 seconds agitation | 300 seconds agitation | 10 seconds agitation | 300 seconds agitation |
| 48 | 1 | 1 | 8.6 | 5.1 | A | A | A | A |
| 49 | 2 | 2 | 8.4 | 5.1 | A | A | B | A |
| 50 | 3 | 3 | 8.7 | 5.4 | B | B | C | B |
| 51 | 4 | 4 | 8.7 | 6.0 | C | B | C | C |

TABLE 18-continued

Charging characteristics of magenta toners (1) to (14)

| | | | Particle size distribution | | Changeability | | | |
| | | | | | Normal temperature and normal humidity (Q/M) | | High temperature and high humidity (Q/M) | |
| Examples | Indicated compound No. | Toner No.: red | Weight average particle size (μm) | Fine powder amount (number %) | 10 seconds agitation | 300 seconds agitation | 10 seconds agitation | 300 seconds agitation |
|---|---|---|---|---|---|---|---|---|
| 52 | 5 | 5 | 8.6 | 6.0 | C | B | C | B |
| 53 | 6 | 6 | 8.7 | 5.5 | B | B | B | B |
| 54 | 7 | 7 | 8.5 | 5.4 | A | A | A | A |
| 55 | 8 | 8 | 8.4 | 5.5 | A | A | B | A |
| 56 | 9 | 9 | 8.4 | 5.6 | A | A | B | A |
| 57 | 10 | 10 | 8.3 | 5.1 | A | A | A | A |
| 58 | 11 | 11 | 8.4 | 5.1 | B | A | B | A |
| 59 | 12 | 12 | 8.6 | 5.6 | A | A | B | A |
| 60 | 13 | 13 | 8.7 | 5.5 | A | A | B | A |
| 61 | 14 | 14 | 8.8 | 5.8 | A | A | A | A |
| Comparative Example 4 | — | 15 | 8.6 | 5.1 | D | C | D | C |

Examples 81 to 92 and
Comparative Examples 5 to 8

Developers prepared in Examples 25, 33, 36, 39, 47, 50, 53, 61, 64, 67, 75 and 78 and Comparative Examples 1 to 4 as Examples 81 to 92 and Comparative Examples 5 to 8 were subjected to copying tests using a modified version of a commercially available color electrophotographic copier CLC-500 (manufactured by Canon Inc.) in which the OPC photosensitive drum was replaced by an amorphous silicon drum. The tests were preformed in an environment of 23° C./60%, and image density, fog, and transferability after copying 300 or 5,000 sheets were evaluated as described below. Table 19 shows the results obtained.

Evaluation of Printed-out Image

<1> Image Density

An image was printed out on a predetermined number of sheets of usual plain paper for copiers (75 g/m²). An image density was evaluated based on the degree of maintenance of the image density of an image at the time of completion of printing with respect to the initial image. The image density was measured by using a Macbeth reflective densitometer (manufactured by Macbeth Co.) relative to a printed-out image of a white ground portion having an original density of 0.00 according to the following standard:

A: Excellent (having an image density of 1.40 or more at the time of completion of printing)
B: Good (having an image density of 1.35 or more and less than 1.40 at the time of completion of printing)
C: Fair (having an image density of 1.00 or more and less than 1.35 at the time of completion of printing)
D: Unacceptable (having an image density of less than 1.00 at the time of completion of printing)

<2> Fog

A solid image was printed out on a predetermined number of sheets of usual paper for copiers (75 g/m²) and the printed-out image at the time of completion of printing test was evaluated with respect to a blank copy area (or white solid image). Specifically, evaluation was made in the following manner. The blank copy area of a printed-out image was measured with respect to a reflection density using a reflective densitometer (REFLECTOMETER ODEL TC-6DS manufactured by Tokyo Denshoku Co., Ltd.) and the worst value thereof was named "Ds". The average value of reflection density of a sheet of copy paper before printing was named "Dr". From these values a value of (Ds–Dr) was obtained, which was defined as a fog amount and evaluated according to the following standards.

A: Very good (having a fog of 0% or more and less than 1.5%)
B: Good (having a fog of 1.5% or more and less than 3.0%)
C: Practically usable (having a fog of 3.0% or more and less than 5.0%)
D: Practically unusable (having a fog of less than 5.0%)

<3> Transferability

A black solid image was printed out on a predetermined number of sheets of usual plain paper for copiers (75 g/m²) and a dropout amount of the image at the time of completion of printing was detected by visual observation and evaluated according to the following standards.

A: Very good (almost no dropout)
B: Good (Slight dropout)
C: Practically usable
D: Practically unusable.

TABLE 19

Results of evaluation of printed-out image

| | | After 300 sheets | | | After 500 sheets | | |
|---|---|---|---|---|---|---|---|
| Examples | Toner No. | Image density | Image fog | Transferability | Image density | Image fog | Transferability |
| 62 | Blue 1 | A | A | A | A | A | A |
| 63 | Blue 9 | A | A | A | A | A | B |
| 64 | Blue 12 | A | A | A | A | A | A |
| 65 | Yellow 1 | A | A | A | A | A | A |
| 66 | Yellow 9 | A | A | A | B | A | A |
| 67 | Yellow 12 | A | A | A | A | A | A |
| 68 | Black 1 | A | A | A | A | A | A |
| 69 | Black 9 | A | A | A | B | A | A |
| 70 | Black 12 | A | A | A | A | A | A |
| 71 | Red 1 | A | A | A | A | A | A |
| 72 | Red 9 | A | A | A | A | A | B |
| 73 | Red 12 | A | A | A | A | A | A |
| Comparative Example 5 | Blue 15 | C | D | D | D | D | D |
| 6 | Yellow 15 | C | D | C | D | D | D |
| 7 | Black 15 | C | D | D | D | D | D |
| 8 | Red 15 | C | D | C | D | D | D |

Example 93

A polymer toner having a weight average particle size of 8.6 μm was obtained by using Exemplary compound (1) in the same manner as in Example 25 except that the formulation of monomer mixture was changed to the one described below. The fine powder amount of the toner was 5.1 number %.

| | |
|---|---|
| Styrene | 180 parts |
| 2-Ethylhexyl acrylate | 20 parts |
| Paraffin wax (m.p. 75° C.) | 20 parts |
| Magnetic material (titanium coupling agent-treated preparation) | 160 parts |
| Styrene/dimethylaminoethyl methacrylate copolymer | 10 parts |
| (Mw = 30,000, Mw / Mn = 3.0, amine value = 50) | |
| Exemplary compound (1) | 6 parts |

This toner mixed with the same silica as used in Example 25 in the same proportion as in Example 25 was applied to a commercially available copier (trade name: NP-4835, manufactured by Canon Inc.) and copying tests were performed under an environment of 23° C./60%. As a result, a clear image having an image density of 1.44 without fog and coarsening and the resolution of 6.2 lines/mm was obtained. In addition, continuous 20,000-sheet copying was performed to examine the durability. As a result, a good image was obtained, which has an image density of 1.39 and the resolution of 6.2 lines/mm, which bore comparison with the initial image.

Measurement of triboelectric charge amount of the toner on the developing sleeve gave an amount of +8.0 μC/g at the initial stage and an amount of +7.6 μC/g after copying 20,000 sheets with substantially no contamination of the sleeve. Then, copying tests performed under an environment of 15° C./10% similarly gave high density, good quality images. Continuous 20,000-sheet copying tests also gave good results. The same copying tests and continuous copying tests performed under the same conditions as described above but under an environment of 35° C./85% provided good results. Furthermore, the same copying tests and continuous copying tests as described above performed under the same conditions as described above under the latter environment but after standing the toner for 1 month gave satisfactory results without causing any problem.

Comparative Example 9

A fine powder having a weight average particle size of 8.5 μm was obtained in the same manner as in Example 93 except that the formulation contained no Exemplary compound (1) and the fine powder was mixed with the same silica in the same proportion as in Example 93, producing a toner. Observation of the toner surface revealed that more emulsified fine powders than in Example 93 were attached.

Copying tests performed by applying this toner to a commercially available electrophotographic copier (trade name: NP-4835, manufactured by Canon Inc.) under an environment of 15° C./10% provided an image density of 1.29. However, examination of durability by performing continuous copying tests resulted in a decrease of image density as low as 1.16 after printing 2,000 sheets.

Example 94

| | |
|---|---|
| Styrene/butyl acrylate resin | 100 parts |
| Magnetic iron oxide | 80 parts |
| Low molecular weight polypropylene wax | 4 parts |
| C.I. Pigment Blue-15:3 | 2 parts |
| Exemplary compound (1) | 4 parts |

After well pre-mixing it in a Henschel mixer, the above material was melt-kneaded in a two-screw kneading extruder set at 140° C. The obtained kneaded composition was cooled and roughly divided by using a cutter mill and then comminuted in a pulverizer using a jet stream. The obtained finely pulverized powder was classified by using an air classifier to obtain blue-colored particle (16) having a weight average particle size of 8.4 μm.

To 100 parts by weight of the obtained blue-colored particle (16), 0.6 parts by weight of silica fine powders (BET specific surface area of 130 m²/g) treated with amino-modified silicone oil to be hydrophobic was added and mixed by using a Henschel mixer to prepare blue-colored toner (16) having silica fine powders on the surface thereof.

The obtained blue-colored toner (16) was mixed with an iron powder carrier EFV 200/300 (tradename, produced by Powdertech Co., Ltd.) in a ratio of 0.5/9.5 by using a tumbler mixer to form a two-component blue developer (16).

Examples 95 and 96

Blue toners (17) and (18) in Examples 95 and 96 were obtained in the same manner as in Example 94 except that 4 parts by weight of Exemplary compounds (9) and (12) were used instead of Exemplary compound (1). The obtained toners had a weight average particle size of 8.3 μm and 8.4 μm, respectively. Using the blue toners (17) and (18), two-component blue developers (17) and (18) were obtained in the same manner as in Example 94.

Comparative Example 10

Blue toner 19 in Comparative Example 10 was obtained in the same manner as in Example 94 except that no exemplary compound was used. The obtained toner had a weight average particle size of 8.6 μm. Using the blue toner 19, a two-component blue developer 19 in Comparative Example 10 was obtained in the same manner as in Example 94.

Evaluation

For the two-component blue developers (16) to (18) obtained in Examples 94 to 96 and a two-component blue developer 19 obtained in Comparative Example 10, toner charge amounts after 10 seconds or 300 seconds agitation were measured according to the measurement method for charge as described above, under a normal temperature and normal humidity environment (25° C., 60% RH) and a high temperature and high humidity environment (30° C., 80% RH). The measured values of two-component blow-off charge were rounded off to the first decimal place and evaluated according to the following standards. Table 20 shows the results obtained.

Chargeability

A: Very good (+30.0 to +40.0 μC/g)
B: Good (+20.0 to +29.9 μC/g)
C: Practically usable (+10.0 to +19.9 μC/g)
D: Practically unusable (.+9.9 μC/g or less)

printing with respect to the initial image. The image density was measured by using Macbeth reflective densitometer (manufactured by Macbeth Co.) relative to a printed-out image of a white ground portion having an original density of 0.00 according to the following standard:

A: Excellent (having an image density of 1.40 or more at the time of completion of printing)
B: Good (having an image density of 1.35 or more and less than 1.40 at the time of completion of printing)
C: Fair (having an image density of 1.00 or more and less than 1.35 at the time of completion of printing)
D: Unacceptable (having an image density of less than 1.00 at the time of completion of printing)

<2> Fog

A solid image was printed out on a predetermined number of sheets of usual paper for copiers (75 g/m$^2$) and the printed-out image at the time of completion of a printing test was evaluated with respect to the blank copy area (or a white solid image. Specifically, evaluation was made in the following manner. The blank copy area of a printed-out image was measured with respect to a reflection density using a reflective densitometer (REFLECTOMETER ODEL TC-6DS manufactured by Tokyo Denshoku Co., Ltd.) and the worst value thereof was named "Ds". The average value of reflection density of a sheet of copy paper before printing was named "Dr". From these values a value of (Ds–Dr) was obtained, which was defined as a fog amount and evaluated according to the following standards.

A: Very good (having a fog of 0% or more and less than 1.5%)
B: Good (having a fog of 1.5% or more and less than 3.0%)
C: Practically usable (having a fog of 3.0% or more and less than 5.0%)

TABLE 20

Charging characteristics of blue toners (16) to (18)

| | | | Changeability | | | |
|---|---|---|---|---|---|---|
| | | | Normal temperature and normal humidity (Q/M) | | High temperature and high humidity (Q/M) | |
| Examples | Indicated compound No. | Toner No.: blue | 10 seconds agitation | 300 seconds agitation | 10 seconds agitation | 300 seconds agitation |
| 75 | 1 | 16 | A | A | A | A |
| 76 | 9 | 17 | A | A | B | A |
| 77 | 12 | 18 | A | A | A | A |
| Comparative Example 10 | — | 19 | D | C | D | D |

Examples 97 to 99 and Comparative Example 11

In Examples 97 to 99 and Comparative Example 11, the blue-colored toners (16) to (18) and 19 obtained in Examples 94 to 96 and Comparative Example 10 were applied to a copier (trade name: NP-4835, manufactured by Canon Inc.) and copying tests were performed under an environment of 23° C./60%, and image density, fog, and transferability after copying 300 or 5,000 sheets were evaluated as described below. Table 21 shows the results obtained.

Evaluation of Printed-out Image

<1>Image Density

An image was printed out on a predetermined number of sheets of usual plain paper for copiers (75 g/m$^2$). An image density was evaluated based on the degree of maintenance of the image density of an image at the time of completion of D: Practically unusable (having a fog of less than <3> Transferability A black solid image was printed out on a predetermined number of sheets of usual plain paper and a dropout amount of the image at the time of completion of printing was detected by visual observation and evaluated according to the following standards.

A: Very good (almost no dropout)
B: Good (Slight dropout)
C: Practically usable
D: Practically unusable.

TABLE 21

Results of evaluation of printed-out image

| | | After 300 sheets | | | After 500 sheets | | |
|---|---|---|---|---|---|---|---|
| Examples | Toner No. | Image density | Image fog | Transfer-ability | Image density | Image fog | Transferability |
| 78 | Blue 16 | A | A | A | A | A | A |
| 79 | Blue 17 | A | A | A | A | A | B |
| 80 | Blue 18 | A | A | A | A | A | A |
| Comparative Example 11 | Blue 19 | C | D | D | D | D | D |

The present invention has been described in detail with respect to the preferred embodiments and can be changed, and modifications may be made without departing from its broader aspects, and it is intended that the appended claims cover all such changes and modifications as fall within the true spirit of the invention.

What is claimed is:

1. A polyhydroxyalkanoate comprising in a polymer molecule thereof at least one of a 3-hydroxy-(substituted phenylsulfinyl)alkanoate unit of a general formula (1) below:

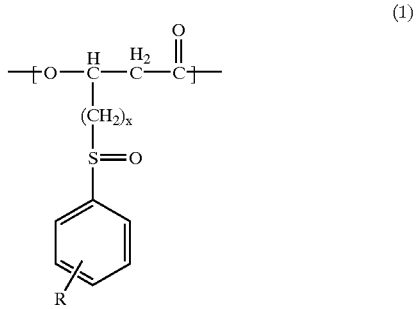

$x = 1-7$ (wherein R is H, halogen, CN, $NO_2$, COOR', or $SO_2R''$ (where R' is H, Na, K, $CH_3$ or $C_2H_5$ and R" is OH, ONa, OK, halogen, $OCH_3$ or $OC_2H_5$) and x is an integer selected from 1 to 7, provided that x may take one or more values in the polymer), and a 3-hydroxy-(substituted phenylsulfonyl)alkanoate unit of a general formula (2) below:

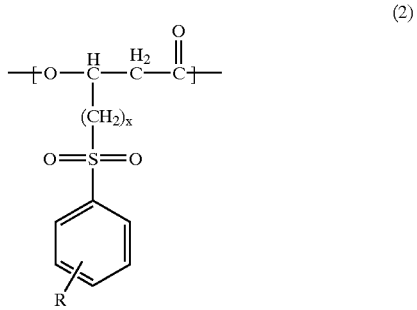

$x = 1-7$ (wherein R is H, halogen, CN, $NO_2$, COOR', or $SO_2R''$ (where R' is H, Na, K, $CH_3$ or $C_2H_5$ and R" is OH, ONa, OK, halogen, $OCH_3$ or $OC_2H_5$) and x is an integer selected from 1 to 7, provided that x may take one or more values in the polymer).

2. A polyhydroxyalkanoate according to claim 1, further comprising in the polymer molecule thereof a 3-hydroxy-(substituted phenylsulfanyl)alkanoate unit of a general formula (3) below:

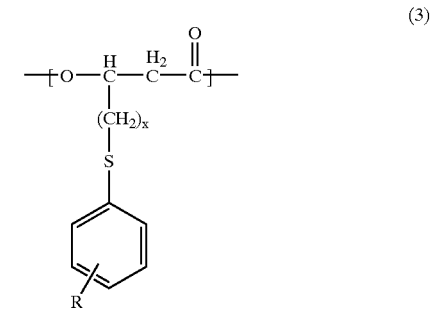

$x = 1-7$ (wherein R is H, halogen, CN, $NO_2$, COOR', or $SO_2R''$ (where R' is H, Na, K, $CH_3$ or $C_2H_5$ and R" is OH, ONa, OK, halogen, $OCH_3$ or $OC_2H_5$) and x is an integer selected from 1 to 7, provided that x may take one or more values in the polymer).

3. A polyhydroxyalkanoate according to claim 1, further comprising in the polymer molecule thereof, in addition to at least one of the units of the general formulas (1) and (2) and the unit of formula (3), at least one of a 3-hydroxyalkanoate unit of the general formula (4) below:

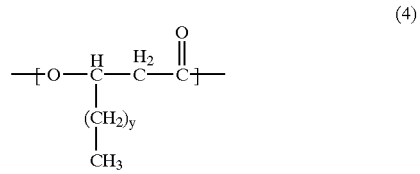

$y = 0-8$ (wherein y is an integer selected from 0 to 8, provided that y may take one or more values in the polymer), and a 3-hydroxyalk-5-enoate unit of a general formula (5) below:

(5)

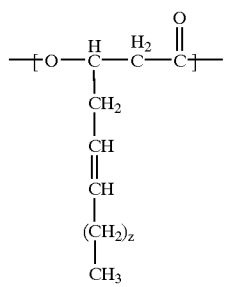

z = 3,5

(wherein z is an integer selected from 3 and 5, provided that z may take one or more values in the polymer).

4. A polyhydroxyalkanoate according to claim 1, wherein the polymer molecule has a number average molecular weight in the range of from 1,000 to 500,000.

5. A production method for producing a polyhydroxyalkanoate, comprising:

(Step 1) culturing a microorganism in a medium containing at least one ω-(substituted phenylsulfanyl)alkanoic acid of a general formula (18) below:

(18)

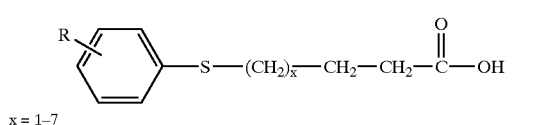

x = 1–7

(wherein R is H, halogen, CN, $NO_2$, COOR', or $SO_2R''$ (where R' is H, Na, K, $CH_3$ or $C_2H_5$ and R" is OH, ONa, OK, halogen, $OCH_3$ or $OC_2H_5$), and x is an integer selected from 1 to 7; and (Step 2) treating a polyhydroxyalkanoate produced by the microorganism cultured in Step 1 with a peroxide compound.

6. A production method according to claim 5, wherein the peroxide compound used in Step 2 is at least one peroxide compound selected from the group consisting of hydrogen peroxide, sodium percarbonate, metachloroperbenzoic acid, performic acid, and peracetic acid.

7. A production method according to claim 5, wherein the medium used in Step 1 contains polypeptone.

8. A production method according to claim 5, wherein the medium used in Step 1 contains yeast extract.

9. A production method according to claim 5, wherein the medium used in Step 1 contains a saccharide.

10. A production method according to claim 9, wherein the saccharide contained in the medium is at least one compound selected from the group consisting of glyceraldehyde, erythrose, arabinose, xylose, glucose, galactose, mannose, fructose, glycerol, erythritol, xylitol, glucuronic acid, galacturonic acid, maltose, sucrose and lactose.

11. A production method according to claim 5, wherein the medium used in Step 1 contains an organic acid or its salt.

12. A production method according to claim 11, wherein the organic acid or its salt contained in the medium is at least one compound selected from the group consisting of pyruvic acid, malic acid, lactic acid, citric acid, succinic acid, and salts thereof.

13. A production method according to claim 5, wherein the medium used in Step 1 contains an amino acid or its salt.

14. A production method according to claim 13, wherein the amino acid or its salt contained in the medium comprises at least one compound selected from the group consisting of glutamic acid, aspartic acid and salts thereof.

15. A production method according to claim 5, wherein the medium used in Step 1 contains a linear alkanoic acid having 4 to 12 carbon atoms or its salt.

16. A production method according to claim 5, wherein the culture of the microorganism in Step 1 is performed by a culture method having at least two stages comprising:

(Step 1-1) culturing the microorganism in a medium containing at least one o)-(substituted phenylsulfanyl) alkanoic acid of the general formula (18) above and polypeptone; and subsequently (Step 1-2) further culturing the microorganism cultured in Step 1-1 above in a medium containing at least one ω-(substituted phenylsulfanyl)alkanoic acid of the general formula (18) above and an organic acid or salt thereof.

17. A production method according to claim 5, wherein the culture of the microorganism in Step 1 is performed by a culture method having at least two stages comprising:

(Step 1-3) culturing the microorganism in a medium containing at least one ω-(substituted phenylsulfanyl) alkanoic acid of the general formula (18) above and a saccharide; and subsequently (Step 1-4) further culturing the microorganism cultured in Step 1-3 above in a medium containing at least one ω-(substituted phenylsulfanyl)alkanoic acid of the general formula (18) above and a saccharide.

18. A production method according to claim 5, wherein the microorganism that produces a polyhydroxyalkanoate in Step 1 is a microorganism belonging to genus *Pseudomonas*.

19. A production method according to claim 18, wherein the microorganism belonging to genus *Pseudomonas* is one selected from the group consisting of *Pseudomonas cichorii* strain YN2 (FERM BP-7375), *Pseudomonas cichorii* strain H45 (FERM BP-7374), and *Pseudomonas jessenii* strain P161 (FERM BP-7376).

20. In a charge control agent for controlling a charge of powder or granules, wherein the charge control agent comprises at least one unit selected from the group consisting of monomer units of general formulae (1) and (2) below:

(1)

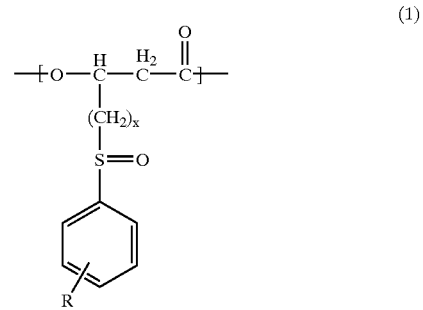

x = 1–7

-continued (2)

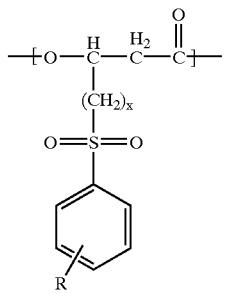

x = 1–7

(wherein R is H, halogen, CN, $NO_2$, COOR', or $SO_2R''$ (where R' is H, Na, K, $CH_3$ or $C_2H_5$ and R" is OH, ONa, OK, halogen, $OCH_3$ or $OC_2H_5$) and x is an integer and may take one or more optional values within a range indicated in the chemical formula).

21. A charge control agent according to claim 20, further comprising in addition to the unit of the chemical formula (1) or (2), a unit of the chemical formula (3) below:

(3)

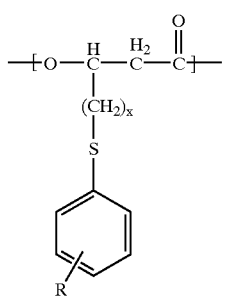

x = 1–7

(wherein R is H, halogen, CN, $NO_2$, COOR', or $SO_2R''$ (where R' is H, Na, K, $CH_3$ or $C_2H_5$ and R" is OH, ONa, OK, halogen, $OCH_3$ or $OC_2H_5$) and x is an integer and may take one or more optional values within a range indicated in the chemical formula).

22. A charge control agent according to claim 20, further comprising, in addition to at least one of the units of chemical formulae (1) and (2) and the unit of formula (3), at least one of a 3-hydroxyalkanoate unit of the chemical formula (4) below:

(4)

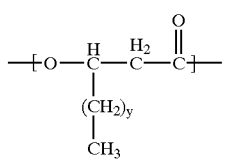

y = 0–8

(wherein y and z are each an integer and may take one or more optional values within a range indicated in the chemical formula independently of the units of the formulae (1), (2) and (3)), and a 3-hydroxyalk-5-enoate unit of a general formula (5) below:

(5)

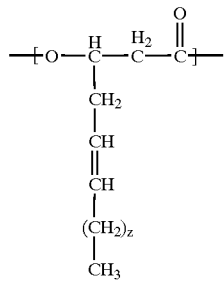

z = 3,5

(wherein z is an integer selected from 3 and 5, provided that z may take one or more values in the polymer).

23. A charge control agent according to claim 20, wherein the powder or granules comprises a toner for developing an electrostatic charge image.

24. A charge control agent according to claim 20, wherein the polyhydroxyalkanoate has a number average molecular weight in the range of from 1,000 to 500,000.

25. In a toner binder for use in a toner for developing an electrostatic charge image, wherein the toner binder contains the charge control agent as claimed in claim 20.

26. In a toner binder for use in a toner for developing an electrostatic charge image, wherein the toner binder contains at least a binder resin, a colorant and the charge control agent as claimed in claim 20.

27. An image forming method comprising at least the steps of: externally applying a voltage to a charging member to charge an electrostatic latent image bearing member; forming an electrostatic charge image on the charged electrostatic latent image bearing member; developing the electrostatic charge image by using an electrostatic charge image developing toner to form a toner image on the electrostatic latent image bearing member; transferring the toner image on the electrostatic latent image bearing member to a recording medium; and thermally fixing the toner image on the recording medium,
wherein there is used the electrostatic charge image developing toner containing at least a binder resin, a colorant and the charge control agent as claimed in claim 20.

28. An image forming method according to claim 27, comprising at least the steps of: externally applying a voltage to a charging member to charge an electrostatic latent image bearing member; forming an electrostatic charge image on the charged electrostatic latent image bearing member; developing the electrostatic charge image by using an electrostatic charge image developing toner to form a toner image on the electrostatic latent image bearing member; transferring the toner image on the electrostatic latent image bearing member to an intermediate transfer member in a first stage; transferring the toner image on the intermediate transfer member to a recording medium in a second stage; and thermally fixing the toner image on the recording medium,
wherein there is used the electrostatic charge image developing toner containing at least a binder resin, a colorant and the charge control agent as claimed in claim 20.

29. An image forming apparatus comprising at least: a means for externally applying a voltage to a charging member to charge an electrostatic latent image bearing member; a means for forming an electrostatic charge image on the charged electrostatic latent image bearing member; a developing means for developing the electrostatic charge image by using an electrostatic charge image developing toner to form a toner image on the electrostatic latent image bearing member; a transfer means for transferring the toner image on the electrostatic latent image bearing member to a recording medium; and a fixing means for thermally fixing the toner image on the recording medium, wherein there is used the electrostatic charge image developing toner containing at least a binder resin, a colorant and the charge control agent as claimed in claim 20.

30. An image forming apparatus according to claim 29, having at least: a means for externally applying a voltage to a charging member to charge an electrostatic latent image bearing member; a means for forming an electrostatic charge image on the charged electrostatic latent image bearing member; a developing means for developing the electrostatic charge image by using an electrostatic charge image developing toner to form a toner image on the electrostatic latent image bearing member; a first transfer means for transferring the toner image on the electrostatic latent image bearing member to an intermediate transfer member; a second transfer means for transferring the toner image on the intermediate transfer member to a recording medium; and a fixing means for thermally fixing the toner image on the recording medium thereto, wherein there is used the electrostatic image developing toner containing at least a binder resin, a colorant and the charge control agent as claimed in claim 20.

* * * * *

UNITED STATES PATENT AND TRADEMARK OFFICE
CERTIFICATE OF CORRECTION

| | | |
|---|---|---|
| PATENT NO. | : 6,808,854 B2 | |
| APPLICATION NO. | : 10/133671 | |
| DATED | : October 26, 2004 | |
| INVENTOR(S) | : Takeshi Imamura et al. | |

It is certified that error appears in the above-identified patent and that said Letters Patent is hereby corrected as shown below:

COLUMN 3
Line 43, "reactivity," should read --reactivity, Macromolecules, 32, 8315-8318 (1999) reports that--.

COLUMN 4
Line 24, "of as" should read --of these as--; and
Line 56, "may" should read --may have--.

COLUMN 5
Line 21, "noxius" should read --noxious--.

COLUMN 6
Line 16, "close" should read --closes--; and
Line 24, "toner binder" should read --toner characterized by containing a lactic-acid resin as a binder--.

COLUMN 7
Line 63, "a intermediate" should read --an intermediate--.

COLUMN 12
Line 19, "containing" should read --containing in--.

COLUMN 20
Line 23, "(1)and" should read --(1) and--; and
Line 52, "formula):" should read --formula).--.

COLUMN 24
Line 15, "mane" should read --name--.

COLUMN 25
Line 57, "Mobility:" should read --Motility:--.

COLUMN 27
Line 59, "may" should read --may be--.

COLUMN 32
Formula (1), the portion of the formula reading "HN" should be deleted.

COLUMN 35
Line 8, "requires" should read --require--; and
Line 26, "unit," should read --units,--.

UNITED STATES PATENT AND TRADEMARK OFFICE
CERTIFICATE OF CORRECTION

PATENT NO. : 6,808,854 B2
APPLICATION NO. : 10/133671
DATED : October 26, 2004
INVENTOR(S) : Takeshi Imamura et al.

It is certified that error appears in the above-identified patent and that said Letters Patent is hereby corrected as shown below:

COLUMN 37
Line 5, "has" should read --have--; and
Line 54, "domains." should read --domain.--.

COLUMN 39
Line 9, "p-n-octylstyrene p-n-" should read --p-n-octylstyrene, p-n- --.

COLUMN 41
Line 7, "Red. 4," should read --Red 4,--.

COLUMN 42
Line 29, "islets" should read --islets.--.

COLUMN 43
Line 41, "groups," should read --group,--.

COLUMN 44
Line 31, "antimony" should read --antimony,--.

COLUMN 47
Line 64, "1 hour" should read --for 1 hour--.

COLUMN 49
Line 14, "any water" should read --any water that--.

COLUMN 51
Line 19, "in" should read --in Example 1.--; and
Line 21, "Example 1" should be deleted.

COLUMN 53
Line 66, "units" should read --units,--.

COLUMN 54
Line 18, "NH4Cl" should read --$NH_4Cl$--; and
Line 25, "50 mL" should read --50 mL of commercially available hydrogen peroxide solution--.

COLUMN 58
Line 45, "Chemical-" should read --Chemical--.

UNITED STATES PATENT AND TRADEMARK OFFICE
CERTIFICATE OF CORRECTION

PATENT NO. : 6,808,854 B2
APPLICATION NO. : 10/133671
DATED : October 26, 2004
INVENTOR(S) : Takeshi Imamura et al.

It is certified that error appears in the above-identified patent and that said Letters Patent is hereby corrected as shown below:

COLUMN 59
Line 46, "24" should read --24 hours. After the culture, the microbial cells were--.

COLUMN 60
Line 51, "1H-NMR" should read --$^1$H-NMR--.

COLUMN 64
Line 22, "DTFCO," should read --DIFCO,--.

COLUMN 65
Line 14, "(1H-NMR)" should read --($^1$H-NMR)--.

COLUMN 68
Line 51, "Tale 11" should read --Table 11--.

COLUMN 71
Line 42, "4 parts" should be deleted; and
Line 43, "Exemplary compound (1)" should read --Exemplary compound (1)     4 parts--.

COLUMN 74
Line 35, "Example 2." should read --Example 2,--.

COLUMN 78
Line 36, "under of" should read --under--; and
Table 18, "Changeability" should read --Chargeability--.

COLUMN 79
Table 18 (cont.), "Changeability" should read --Chargeability--; and
Line 36, "preformed" should read --performed--.

COLUMN 81
Line 39, "6 parts" should be deleted; and
Line 40, "Exemplary compound (1)" should read --Exemplary compound (1)     6 parts--.

COLUMN 82
Line 47, "well pre-mixing it" should read --pre-mixing it well--.

COLUMN 83
Line 33, "(.+9.9" should read --(+9.9--; and
Table 20, "Changeability" should read --Chargeability--.

UNITED STATES PATENT AND TRADEMARK OFFICE
CERTIFICATE OF CORRECTION

PATENT NO.         : 6,808,854 B2
APPLICATION NO. : 10/133671
DATED              : October 26, 2004
INVENTOR(S)     : Takeshi Imamura et al.

It is certified that error appears in the above-identified patent and that said Letters Patent is hereby corrected as shown below:

COLUMN 84
Line 19, "solid image." should read --solid image.)--; and
Line 53, "than" should read --than 5.0%)--.

COLUMN 86
Line 45 (Claim 3, Line 1), "claim 1" should read --claim 2--.

COLUMN 88
Line 16 (Claim 16, Line 5), "o)-(substituted" should read --ω-(substituted--.

COLUMN 89
Line 47 (Claim 22, Line 1), "claim 20" should read --claim 21--; and
Line 63, "and z are each" should read --is--.

Signed and Sealed this

First Day of August, 2006

JON W. DUDAS
*Director of the United States Patent and Trademark Office*